United States Patent
Pagano et al.

(10) Patent No.: US 8,076,309 B2
(45) Date of Patent: Dec. 13, 2011

(54) USP47 INHIBTORS AND METHODS TO INDUCE APOPTOSIS

(75) Inventors: Michele Pagano, New York, NY (US); Jeffrey R. Skaar, New York, NY (US); Angelo Peschiaroli, Rome (IT); N. Valerio Dorrello, Caivano (IT)

(73) Assignee: New York University, New York, NY (US)

(*) Notice: Subject to any disclaimer, the term of this patent is extended or adjusted under 35 U.S.C. 154(b) by 0 days.

(21) Appl. No.: 12/431,336

(22) Filed: Apr. 28, 2009

(65) Prior Publication Data

US 2009/0275639 A1 Nov. 5, 2009

Related U.S. Application Data

(60) Provisional application No. 61/049,264, filed on Apr. 30, 2008.

(51) Int. Cl.
C12N 15/11 (2006.01)
C07H 21/02 (2006.01)
C07H 21/04 (2006.01)

(52) U.S. Cl. ..... 514/44; 536/23.1; 536/24.3; 536/24.33; 536/24.5

(58) Field of Classification Search ..... 514/44; 435/6, 91.1; 436/325, 375

See application file for complete search history.

(56) References Cited

U.S. PATENT DOCUMENTS 6,242,590 B1 * 6/2001 Cowsert ..... 536/24.5

OTHER PUBLICATIONS

Wang et al. (Journal of Cell Biology, 2004 vol. 164, No. 7:973-978).*
Hammond et al. (Nature Reviews Genetics 2001, vol. 2:110-119).*
Bai et al., "SKP1 connects cell cycle regulators to the ubiquitin proteolysis machinery through a novel motif, the F-box," *Cell*, 1996, 86:263-274.
Brown and Pagano, "p53 stability," *Biochim. Biophys. Acta*, 1997, 1332:1.
Carrano et al., "Skp2 is required for the ubiquitin-mediated degradation of the Cdk-inhibitor p27," *Nat Cell Biol.*, 1999, 1:193-199.
Cenciarelli et al., "Identification of a family of human F-box proteins," *Current Biol.*, 1999, 9:1177-1179.
Ciechanover, "The ubiquitin-proteasome pathway: on protein death and cell life," *EMBO J.*, 1998, 17:7151-7160.
Davis et al., "Pseudosubstrate regulation of the SCFβ-TrCP ubiquitin ligase by hnRNP-U," *Genes Dev.*, 2002, 16:439-451.
Fong and Sun, "Genetic evidence for the essential role of beta-transducin repeat-containing protein in the inducible processing of NF-kappa B2/p100," *J. Biol. Chem.*, 2002, 277:22111-22114.
Fuchs et al., "HOS, a human homolog of Slimb, forms an SCF complex with Skp1 and Cullin1 and targets the phosphorylation-dependent degradation of IkappaB and beta-catenin," *Oncogene*, 1999, 18:2039-2046.
Fukuchi et al., "Ligand-dependent Degradation of Smad3 by a Ubiquitin Ligase Complex of ROC1 and Associated Proteins," *Mol. Biol. Cell*, 2001, 12-1431-1443.

(Continued)

*Primary Examiner* — Terra Cotta Gibbs
(74) *Attorney, Agent, or Firm* — Fish & Richardson P.C.

(57) ABSTRACT

The present invention relates to USP47 (ubiquitin specific protease 47) inhibitors and methods for inducing apoptosis or cell death in a target cell. In certain embodiments, the invention relates to methods and kits to screen for related agents that induce apoptosis. Additionally, the invention relates to assays for screening compounds capable of acting as USP47 inhibitors.

12 Claims, 3 Drawing Sheets

OTHER PUBLICATIONS

Gonen et al., "Identification of the Ubiquitin Carrier Proteins, E2s, Involved in Signal-induced Conjugation and Subsequent Degradation of IkBa," *J. Biol. Chem.*, 1999, 274:14823-14830.

Guardavaccaro et al., "Control of Meiotic and Mitotic Progression by the F Box Protein Trcp1 In Vivo," *Developmental Cell*, 2003, 4:799-812.

Hart et al., "The F-box protein b-TrCP associates with phosphorylated b-catenin and regulates its activity in the cell," *Curr. Biol.*, 1999, 9:207-210.

Hatakeyama et al., "Ubiquitin-dependent degradation of IkBa is mediated by a ubiquitin ligase Skp1yCul 1yF-box protein FWD1," *Proc. Natl. Acad. Sci. USA*, 1999, 96:3859-3863.

Hattori et al., "Molecular Dissection of the Interactions among IkBa, FWD1, and Skp1 Required for Ubiquitin-mediated Proteolysis of IkBa," *J. Biol. Chem.*, 1999, 274:29641-29647.

Jiang and Struhl, "Regulation of the Hedgehog and Wingless signaling pathways by the F-box/WD40-repeat protein Slimb," 1998, *Nature*, 391:493-496.

Kipreos and Pagano, "The F-box protein family," *Genome Biology*, 2000, 1(5):reviews 3002.1-3002.7.

Kitagawa et al., "An F-box protein, FWD1, mediates ubiquitin-dependent proteolysis of b-catenin," *EMBO J.*, 1999, 18:2401-2410.

Koike et al., "Molecular Cloning and Genomic Structure of the bTRCP2 Gene on Chromosome 5q35.1," *Biochem. Biophys. Res. Commun.*, 2000, 269:103-109.

Kroll et al., "Inducible Degradation of IkBa by the Proteasome Requires Interaction with the F-box Protein h-bTrCP," *J. Biol. Chem.*, 1999, 274:7941-7946.

Lassot et al., "ATF4 Degradation Relies on a Phosphorylation-Dependent Interaction with the SCFbTrCP Ubiquitin Ligase," *Mol. Cell. Biol.*, 2001, 21:2192-2202.

Latres et al., "The human F box protein b-Trcp associates with the Cul1/Skp1 complex and regulates the stability of b-catenin," *Oncogene*, 1999, 18:849-854.

Lloyd, "p27kip1: A Multifunctional Cyclin-Dependent Kinase Inhibitor with Prognostic Significance in Human Cancers," *Am. J. Pathol.*, 1999, 154: 313-323.

Margottin et al., "A Novel HumanWD Protein, h-bTrCP, that Interacts with HIV-1 Vpu Connects CD4 to the ER Degradation Pathway through an F-Box Motif," *Mol. Cell.*, 1998, 1:565-574.

Marikawa and Elinson, "b-TrCP is a negative regulator of the Wnt/b-catenin signaling pathway and dorsal axis formation in Xenopus embryos," *Mech. Dev.*, 1998, 77:75-80.

Ohta et al., "ROC1, a Homolog of APC11, Represents a Family of Cullin Partners with an Associated Ubiquitin Ligase Activity," *Mol. Cell.*, 1999, 3:535-541.

Orian et al., "SCF$^{\beta\text{-}TrCP}$ ubiquitin ligase-mediated processing of NF-kB p 105 requires phosphorylation of its C-terminus by IkB kinase," *Embo J.*, 2000, 19:2580-2591.

Pagano, "Cell cycle regulation by the ubiquitin highway," *FASEB J.*, 1997, 11:1067-1075.

Peifer, "b-Catenin as Oncogene—The Smoking Gun," *Science*, 1997, 275:1752.

Shirane et al., "Common Pathway for the Ubiquitination of IkBa, IkBb, and IkBe Mediated by the F-Box Protein FWD1," *J. Biol. Chem.*, 1999, 274:28169-28174.

Soldatenkov et al., "Inhibition of Homologue of Slimb (HOS) Function Sensitizes Human Melanoma Cells for Apoptosis," *Cancer Res.*, 1999, 59:5085-5088.

Spataro, "The ubiquitin-proteasome pathway in cancer," *Br. J. Cancer*, 1998, 77:448-455.

Spencer et al., "Signal-induced ubiquitination of IkBa by the F-box protein Slimb/b-TrCP," *Genes Dev.*, 1999, 13:284-294.

Suzuki et al., "IkBa Ubiquitination Is Catalyzed by an SCF-like Complex Containing Skp1, Cullin-1, and Two F-Box/WD40 Repeat Proteins, bTrCP1 and bTrCP2," *Biochem. Biophys. Res.Commun.*, 1999, 256:127-132.

Tan et al., "Recruitment of a ROC1—CUL1 Ubiquitin Ligase by Skp1 and HOS to Catalyze the Ubiquitination of IkBa," *Mol. Cell.* 1999, 3:527-533.

Winston et al., "A family of mammalian F-box proteins," *Current Biol.*, 1999, 9:1180-1182.

Winston et al., "The SCFb-TRCP-ubiquitin ligase complex associates specifically with phosphorylated destruction motifs in Ika and b-catenin and stimulates IkBa ubiquitination in vitro," *Genes Dev.*, 1999, 13:270-283.

Wu and Ghosh, "b-TrCP Mediates the Signalinduced Ubiquitination of IkBb ," *J. Biol. Chem.*, 1999, 274:29591-29594.

Yaron et al., "Identification of the receptor component of the IkBα-ubiquitin ligase," *Nature*, 1998, 396:590-594.

Amerik & Hochstrasse, "Ubiquitin-specific protease Doa4 (*Saccharomyces cerevisiae*)," In *Handbook of Proteolytic Enzymes*, 2004, 2 Ed., Barrett, A. J., Rawlings, N. D. & Woessner, J. F.), p. 1229-1231, Elsevier, London.

Baker, "Ubiquitin-specific proteases 4 and 15," In *Handbook of Proteolytic Enzymes*, 2 Ed. (Barrett, A. J., Rawlings, N. D. & Woessner, J. F.), p. 1232-1236, Elsevier, London.

Everett, "Ubiquitin-specific protease 7," In *Handbook of Proteolytic Enzymes*, 2 Ed. (Barrett, A. J., Rawlings, N. D. & Woessner, J. F.), p. 1236-1238, Elsevier, London.

Neer et al., "The ancient regulatory-protein family of WD-repeat proteins," *Nature*, 1996, 371:297-300.

Spevak et al., "Saccharomyces cerevisiae cdc 15 mutants arrested at a late stage in anaphase are rescued by Xenopus cDNAs encoding N-ras or a protein with beta-transducin repeats," *Mol. Cell. Biol.*, 1993, 8:4953-4966.

Wilkinson (2004), Ubiquitin isopeptidase T. In *Handbook of Proteolytic Enzymes*, 2 Ed. (Barrett, A. J., Rawlings, N. D. & Woessner, J. F.), p. 1239-1243, Elsevier, London.

\* cited by examiner

USP47 INHIBTORS AND METHODS TO INDUCE APOPTOSIS

CROSS REFERENCE TO RELATED APPLICATIONS

The present application claims the benefit of U.S. Provisional Patent Application Ser. No. 61/049,264, filed Apr. 30, 2008, the contents of which are hereby incorporated by reference in its entirety.

This invention was made in part in the course of research sponsored by the National Institutes of Health (NIH) Grant R37-CA76584. The U.S. government may have certain rights in this invention.

FIELD OF THE INVENTION

The present invention relates to USP47 (ubiquitin specific protease 47) inhibitors and methods for inducing apoptosis. In certain embodiments, the invention relates to methods and kits to screen for USP47 inhibitors and related agents that induce apoptosis.

BACKGROUND OF THE INVENTION

The availability of the human and mouse genome sequences has allowed the identification and comparison of their respective degradomes—the complete repertoire of proteases that are produced by these organisms. Because of the essential roles of proteolytic enzymes in the control of cell behaviour, survival and death, degradome analysis provides a useful framework for the global exploration of these protease-mediated functions in normal and pathological conditions.

One such family of proteases is the C19 hydrolases. The ubiquitinyl hydrolases of family C19 are intracellular peptidases that remove ubiquitin molecules from polyubiquinated peptides by cleavage of isopeptide bonds. The purpose of the de-ubiquitination is thought to be editing of the ubiquitin conjugates, which could rescue them from degradation, as well as recycling of the ubiquitin. The ubiquitin/proteasome system is responsible for most protein turnover in the mammalian cell, and with over 50 members, family C19 is one of the largest families of peptidases in the human genome.

The peptidases of family C19 have a more complicated structure than the ubiquitinyl hydrolases in the related family C12. Many of the proteins have multiple domains. The peptidase unit contains a 'fingers domain' that is a four-stranded beta sheet that interacts with the ubiquinated substrate. The USP proteolytic system in human tissues is extremely complex.

The Ubiquitin Pathway

Ubiquitin-mediated proteolysis is an important pathway of non-lysosomal protein degradation which controls the timed destruction of many cellular regulatory proteins including, p27, p53, p300, cyclins, E2F, STAT-1, c-Myc, c-Jun, EGF receptor, IκBα, NFκB and β-catenin (reviewed in Pagano, 1997, FASEB J. 11: 1067). Ubiquitin is an evolutionary highly conserved 76-amino acid polypeptide which is abundantly present in all eukaryotic cells. The ubiquitin pathway leads to the covalent attachment of a poly-ubiquitin chain to target substrates which are then degraded by the multi-catalytic proteasome complex (see Pagano, supra, for a recent review). Many of the steps regulating protein ubiquitination are known. Initially the ubiquitin activating enzyme (E1), forms a high energy thioester with ubiquitin which is, in turn, transferred to a reactive cysteine residue of one of many ubiquitin conjugating enzymes (Ubcs or E2s). The final transfer of ubiquitin to an e-amino group of a reactive lysine residue in the target protein occurs in a reaction that may or may not require an ubiquitin ligase (E3) protein. The large number of ubiquitin ligases ensures a high level of substrate specificity.

The Ubiquitin Pathway and the Regulation of the G1 Phase by F Box Proteins

Genetic and biochemical studies in several organisms have shown that the G1 phase of the cell cycle is regulated by the ubiquitin pathway. Proteolysis of cyclins, Ckis and other G1 regulatory proteins is controlled in yeast by the ubiquitin conjugating enzyme Ubc3 (also called Cdc34) and by an E3 ubiquitin ligase formed by three subunits: Cdc53, Skp1 and one of many F box proteins (reviewed in Patton, et al., 1998, Trends in Genet. 14:6). The F box proteins (FBPs) are so called because they contain a motif, the F Box, that was first identified in Cyclin F, and that is necessary for FBP interaction with Skp1 (Bai, et al., 1996, Cell 86:263). Cdc53 (also called Cul A) and Skp1 appear to participate in the formation of at least three distinct E3s, each containing a different FBP. Because these ligases are similar protein modules composed of Skp1, Cul A, and an FBP, they have been named SCF. The three SCFs identified so far in *S. cerevisiae* are: $SCF^{Cdc4}$ (which recruits the Ckis Sic1 and Far1, the replication factor Cdc6, and the transcriptional activator Gcn4, as substrates through the F-Box protein Cdc4), $SC^{Grr1}$ (which recruits the G1 cyclins Cln1 and Cln2 as substrates through the F-Box protein GRR1), and $SCF^{Met30}$ (which recruits the G1 cyclin Cln3 as a substrate throughout the F box protein MET30; see Pagano and Patton, supra, for recent reviews).

The interaction of SCF ligase with its substrates occurs via the FBP. FBPs are present in all eukaryotes (at least 54 in mammals; Cenciarelli, et al., 1999, Current Biol. 9: 1177; Winston, et al., 1999, Current Biol. 9: 1180). In addition to the F Box, many FBPs contain additional domains that facilitate both protein:protein interactions, e.g. WD-40 domains or leucine-rich repeats (LRRs), and protein:DNA interactions, e.g. tankyrase binding domains or HNH domains. Since the substrate specificity of SCF ligases is dictated by different FBPs that act as substrate targeting subunits, the large numbers of FBPs with varying combinations of protein or DNA interaction domains ensure highly specific substrate recognition (Cenciarelli, et al., supra; Winston, et al., supra).

FBP1, A Mammalian FBP Involved in Regulation of APC/C

Fbp1, the mammalian homolog of *Xenopus* β-TrCP1 (β-transducin repeat containing protein) (Spevak, et al., 1993, Mol. Cell. Biol. 8:4953), was identified using Skp1 as a bait in a two-hybrid screen (Cenciarelli, et al., supra). Fbp1 is an F box protein containing seven WD-40 domains (Margottin, et al., 1998, Mol. Cell. 1:565), and is involved in the degradation of IKBα. family members in response to NFKB activating stimuli (Gonen, et al., 1999, J. Biol. Chem. 274:14823; Hatakeyama, et al., 1999, Proc. Natl. Acad. Sci. USA 96:3859; Hattori, et al., 1999, J. Biol. Chem. 274:29641; Kroll, et al., 1999, J. Biol. Chem. 274:7941; Ohta, et al., 1999, Mol. Cell. 3:535; Shirane, et al., 1999, J. Biol. Chem. 274: 28169; Spencer, et al., 1999, Genes Dev. 13:284; Winston, et al., 1999, Genes Dev. 13:270; Wu and Ghosh, 1999, J. Biol. Chem. 274:29591; Yaron, et al., 1998, Nature 396:590). In addition, consistent with the finding that *Xenopus* and *Drosophila* Fbp1 orthologs act as negative regulators of the Wnt/β-catenin signaling pathway (Jiang and Struhl, 1998, Nature 391:493; Marikawa and Elinson, 1998, Mech. Dev. 77:75), several studies report that human Fbp1 controls .beta.-catenin stability in vitro and in mammalian cultured cells (Ilart, et al., 1999, Curr. Biol. 9:207; Ilatakeyama, et al., supra; Kitagawa, et al., 1999, EMBO J. 18:2401; Latres, et al., 1999, Oncogene 18:849; Winston, et al., 1999, Genes Dev. 13:270).

To date, well-characterized substrates of mammalian Fbp1 have been found to share a common destruction motif, DSGxxS, and are recognized by Fbp1 only upon phosphorylation of the two serine residues present in this motif. There is, however, some recent evidence for additional mammalian substrates of Fbp1 lacking a completely conserved binding domain, such as ATF4 (Lassot, et al., 2001, Mol. Cell. Biol. 21:2192), Smad3 (Fukuchi, et al., 2001, Mol. Biol. Cell 12-1431), NFKB p105 (Orian, et al., 2000, EMBO J. 19:2580) and NFKB p100 (Fong and Sun, 2002, J. Biol. Chem. 277:22111). A conserved DSGxxS motif is present not only in Fbp1 substrates but also in certain regulators of Fbp1, such as the HIV protein Vpu, which targets Fbp1 to the non-physiological substrate, CD4, in virally infected cells. (Margottin, et al., supra). The DSGxxS destruction motif may also be found in peptide regulators of Fbp1 termed pseudosubstrates; however, pseudosubstrates escape the normal degradation fate of other FBP target proteins and instead modulate the activity of the FBP, and corresponding Cks, such as cellular localization and substrate targeting. For example, the Fbp1 pseudostibstrate hnRNP-U not only inhibits Fpb1 from targeting inappropriate substrates but also serves to localize Fbp1 to the nucleus (Davis, et al., 2002, Genes Dev. 16:439).

A further level of complexity is added by the presence of a Fbp1/β-TrCP1 paralogous gene product, called β-TrCP2 or Fbxw1B (78% identical, 86% similar; Kipreos and Pagano, 2000, Genome Biology 1:3002.1). Fbp1 and β-TrCP2 are ubiquitously expressed in adult human tissues (Cenciarelli, et al., supra; Koike, et al., 2000, Biochem. Biophys. Res. Commun. 269:103). In addition, β-TrCP2 has biochemical properties similar to Fbp1 in its ability to sustain the ubiquitinylation of both β-catenin and IKBα. family members in vitro and to control their degradation in mammalian cultured cells (Fuchs, et al., 1999, Oncogene 18:2039; Suzuki, et al., 1999, Biochem. Biophys. Res. Commun. 256:127; Tan, et al., 1999, Mol. Cell. 3:527). Despite these similarities, Fbp1 localizes to the nucleus and β-TrCP2 mainly to the cytoplasm (Davis, et al., 2002, Genes Dev. 16:439). It is not clear whether these two FBPs have overlapping functions in vivo, or if each of them recognizes specific substrates.

Deregulation of the Ubiquitin Pathway in Cancer and Other Proliferative Disorders Cancer develops when cells multiply too quickly. Cell proliferation is determined by the net balance of positive and negative signals. When positive signals overcome or when negative signals are absent, the cells multiply too quickly and cancer develops.

Ordinarily cells precisely control the amount of any given protein and eliminate the excess or any unwanted protein. To do so, the cell ubiquitinates the undesired protein to tag the protein for proteasome degradation. This mechanism goes awry in tumors, leading to the excessive accumulation of positive signals (oncogenic proteins), or resulting in the abnormal degradation of negative regulators (tumor suppressor proteins). Thus, without tumor suppressor proteins or in the presence of too much of an oncogenic protein, cells multiply without control, forming tumors (reviewed by Ciechanover, 1998, EMBO J. 17: 7151; Spataro, 1998, Br. J. Cancer 77: 448). For example, abnormal ubiquitin-mediated degradation of the p53 tumor suppressor (reviewed by Brown and Pagano, 1997, Biochim. Biophys. Acta 1332:1), the putative oncogene β-catenin (reviewed by Peifer, 1997, Science 275: 1752) and the Cki p27 (reviewed in Ciechanover, supra; Spataro, supra; Lloyd, 1999, Am. J. Pathol. 154: 313) have been correlated with tumorgenesis, opening to the hypothesis that some genes encoding ubiquitinating enzymes may be mutated in tumors.

Initial evidence indicates that human F box proteins play a role in the ubiquitination of G1 regulatory proteins as do their lioniologues in yeast. Unchecked degradation of cell cycle regulatory proteins has been observed in certain tumors and it is possible that deregulated ubiquitin ligase plays a role in the altered degradation of cell cycle regulators. A well understood example is that of Mdm2, a ubiquitin ligase whose overexpression induces low levels of its substrate, the tumor suppressor p53.

Alternately, F box proteins have been shown to interact directly with DNA regulating proteins or DNA itself (see below). F box proteins in yeast are known to regulate genomic stability and senescence, and recent data has shown that F box inhibition in mammalian cells can lead to the loss of DNA damage checkpoints. The identification of novel F box protein substrates or activity may thus extend the role of F box proteins in tumorigenesis beyond the understood regulation of traditional cell cycle proteins.

One member of the C19 peptidase family is ubiquitin specific protease 47 (USP47), a cysteine protease and deubiquitinating enzyme. While the sequence of USP47 has been identified, no molecular studies have been conducted. Since C19 peptidases are generally involved in regulating the cell cycle, characterizing the activities and roles of specific members would be useful for studying cell cycle regulation and in particular to study the effects on apoptosis.

There is a general need for cancer treatments that utilize methods and agents that regulate or affect the cell cycle to stimulate apoptosis of desired target cells, including cancer cells. Identification of the effects of inhibiting or blocking USP47 would be useful for studying cell cycle regulation and in particular to study the effects on apoptosis. In particular, there is a need for small molecule inhibitors of USP47 useful as cancer chemotherapeutics.

SUMMARY OF THE INVENTION

The present invention provides methods of inducing apoptosis or cell death comprising contacting a target cell with an effective amount of an inhibitor of USP47. In certain embodiments, the target cell is a diseased or abnormal cell from tissue or a cell that exhibits a disease or abnormal condition selected from the group consisting of cancer, infection, immune disorder, cardiovascular disease, and inflammatory disorders.

In certain embodiments, the method further comprises contacting the cell with a second agent for sensitizing the cell to DNA damage or apoptosis.

In yet additional embodiments, the invention provides a method of killing a target cell comprising contacting a cell with an effective amount of an inhibitor of USP47. In certain embodiments, the method further comprises contacting the cell with a second agent for sensitizing the cell to DNA damage or apoptosis.

In certain embodiments, the target cell is a diseased or abnormal cell from tissue or a cell that exhibits a disease or abnormal condition selected from the group consisting of cancer, infection, immune disorder, cardiovascular disease, and inflammatory disorders.

In yet additional embodiments, the invention provides a method of screening for an agent useful for inducing apoptosis of a cancer cell comprising:

i) contacting a cell expressing USP47 with a test compound; and ii) comparing the degradation rate of the USP47 to a control, wherein the control is the degradation rate of USP47 in the absence of test compound; and iii) selecting any test compound increasing the degradation rate of USP47 as useful for inducing apoptosis of a cancer cell.

In certain embodiments, the USP47 comprises the sequence of SEQ ID NO:1.

In yet additional embodiments, the invention provides a method of screening for an agent useful for inducing apoptosis of a cancer cell comprising:

i) contacting a cell expressing USP47 with a test compound;

ii) comparing the amount of USP47 in the cell in the presence and absence of the test compound; and iii) selecting any test compound decreasing the amount of USP47 as useful for inducing apoptosis of a cancer cell.

In certain embodiments, the test compound is an siRNA.

In yet additional embodiments, the USP47 comprises the sequence of SEQ ID NO:1, 3, 4, 5, or 12.

In yet additional embodiments, the invention provides a method of treating cancer comprising: administering an effective amount of a USP47 inhibitor to a subject suffering from cancer. In certain embodiments, the USP47 inhibitor induces apoptosis or cell death.

In other embodiments, the USP47 inhibitor results in loss of β-TrCP activity.

In yet additional embodiments, the invention provides a kit for screening for an agent useful for inhibiting β-TrCP activity, comprising: a USP47 protein, a β-TrCP protein, a means for detecting binding between the USP47 and β-TrCP proteins, and instructions for use.

In yet additional embodiments, the invention provides a kit for screening for an agent useful for inducing apoptosis or cell death comprising: a USP47 protein, a β-TrCP protein, a means for detecting binding between the USP47 and β-TrCP proteins, and instructions for use.

In yet additional embodiments, the invention provides a method of inducing apoptosis or cell death in a target cell of a mammal which comprises contacting said target cell with an effective amount of an inhibitor of USP47 for inducing apoptosis or cell death of an inhibitor of USP47. In certain embodiments, the mammal is a human. In certain embodiments, the inhibitor of USP47 is SEQ ID NO:16 or SEQ ID NO:17.

In yet additional embodiments, the invention provides inhibitors of USP47 comprising SEQ ID NO:16 or SEQ ID NO:17.

In yet other embodiments, the invention is directed to use of any of the aforementioned USP47 inhibitor compounds or compositions in the manufacture of a medicament for inducing apoptosis, cell death, or for treating cancer.

DETAILED DESCRIPTION

Figure 1:
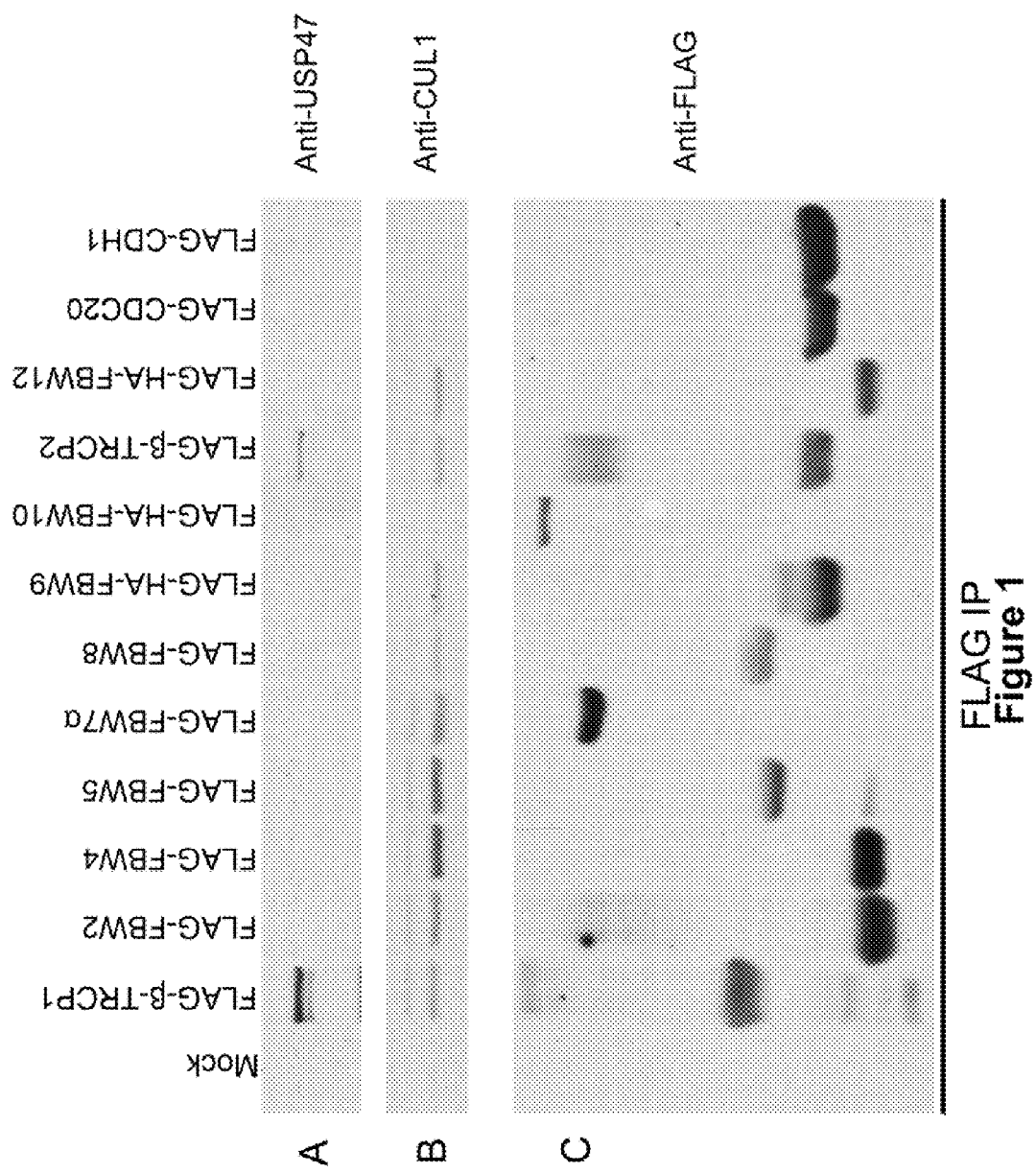
FIG. 1A-C illustrates USP47 specifically binding to β-TrCP1 and β-TRCP2.
Figure 2:
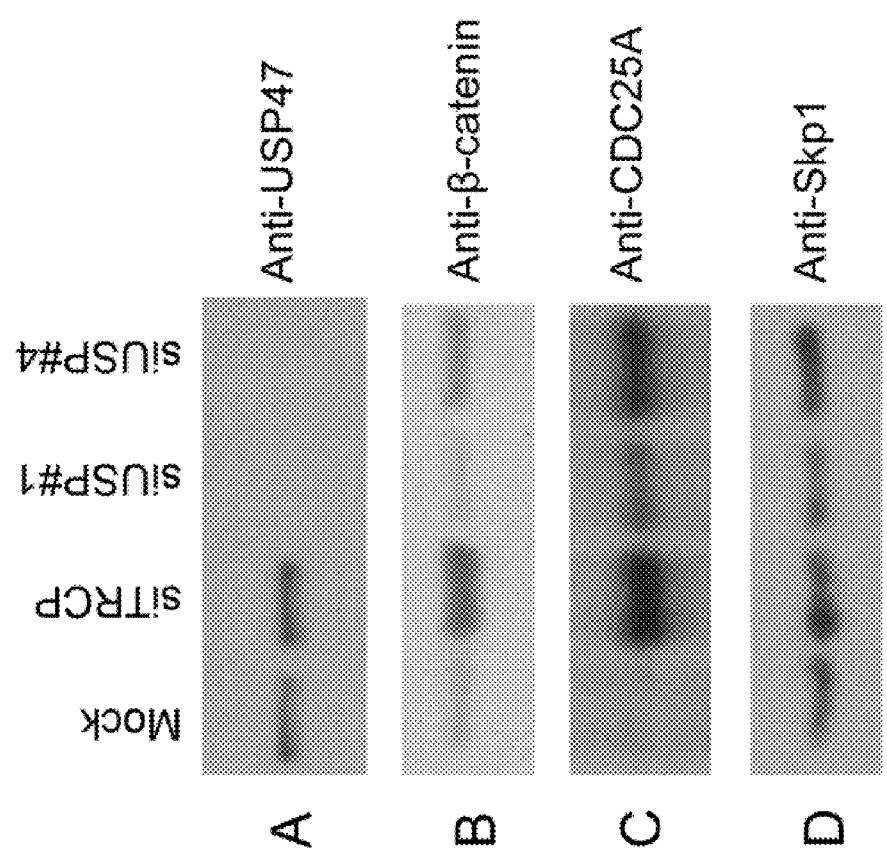
FIG. 2A-D shows USP47 knockdown results increasing β-TrCP substrate levels.

The present invention relates to USP47 (ubiquitin specific protease 47) inhibitors and methods for inducing apoptosis in a target cell. In certain embodiments, the invention relates to methods and kits to screen for related agents that induce apoptosis. The present invention provides methods, compositions, and kits relating to the use of inhibitors of USP47 (ubiquitin specific protease 47) to kill cancerous cells.

In certain embodiments, USP47 inhibition has been found to induce cell death without any additional DNA damage agents. In another embodiment, the invention relates to methods for inducing cell death using at least one USP47 inhibitor along with at least one additional DNA damage or apoptosis inducing agent. In certain embodiments, the invention relates to assays for screening compounds capable of acting as USP47 inhibitors. In additional embodiments, the invention relates to methods for inducing cell death by contacting a target cell with an effective amount of an inhibitor of USP47 and a second agent for sensitizing the cell to DNA damage or apoptosis. In additional embodiments, the invention provides methods relating to cancer therapies and diagnostics. In other embodiments, the USP47 inhibitors and assays will be employed for identifying novel drugs useful for various proliferative and/or differentiative disorders such as major opportunistic infections, immune disorders, cardiovascular diseases and inflammatory disorders.

The peptidases of family C19 hydrolyse bonds involving the carboxyl group of the C-terminal Gly residue of ubiquitin. These ubiquitinyl bonds can be alpha-peptide bonds to the N-terminus of another ubiquitin molecule, or isopeptide bonds to the sidechain of Lys48 in another ubiquitin molecule or to the sidechain of a Lys residue in another protein.

The varied specificities of peptidases in the family have been reviewed by Amerik & Hochstrasse (2004), Ubiquitin-specific protease Doa4 (*Saccharomyces cerevisiae*); In *Handbook of Proteolytic Enzymes*, 2 Ed. (Barrett, A. J., Rawlings, N. D. & Woessner, J. F.), p. 1229-1231, Elsevier, London; Baker (2004), Ubiquitin-specific proteases 4 and 15, In *Handbook of Proteolytic Enzymes*, 2 Ed. (Barrett, A. J., Rawlings, N. D. & Woessner, J. F.), p. 1232-1236, Elsevier, London (2004); Everett (2004), Ubiquitin-specific protease 7. In *Handbook of Proteolytic Enzymes*, 2 Ed. (Barrett, A. J., Rawlings, N. D. & Woessner, J. F.), p. 1236-1238, Elsevier, London (2004); and Wilkinson (2004), Ubiquitin isopeptidase T. In *Handbook of Proteolytic Enzymes*, 2 Ed. (Barrett, A. J., Rawlings, N. D. & Woessner, J. F.), p. 1239-1243, Elsevier, London (2004).

The active site residues in C19 hydrolases occur in the order Asn, Cys, His and Asp. Inhibitors of the ubiquitinyl hydrolases of family C19 include N-Ethylmaleimide (1 mM). More selective blocking reagents include ubiquitin aldehyde (Hu et al., 2002) and vinyl sulfones (Hemelaar et al., 2004).

Ubiquitination of a substrate is believed to take place on one or more lysine residues, and can be detected by assays described herein (see, e.g., the Examples) and in, e.g., Carrano et al. (Nat Cell Biol 1, 193-199 (1999)). The proteolysis of cellular regulatory proteins is a multistep process orchestrated by the concerted action of three enzymes, all leading up to the addition of a ubiquitin peptide to the protein, and subsequent transfer of the ubiquitinylated protein to a cellular structure called the proteasome where it is proteolyzed. The enzymes responsible for recruitment of each particular type of target protein to be proteolyzed are called ubiquitin ligases. Given the diversity of target proteins, there is an equally large number of ubiquitin ligases.

For most substrates of ubiquitin (Ub)-dependent degradation, recognition by the proteasome is mediated by a covalently attached signal assembled from multiple ubiquitins linked to each other via the C terminus of one Ub and the epsilon-amine of Lys(48) of another Ub.

In eukaryotes, covalent attachment of the 76-residue protein ubiquitin (Ub) identifies a substrate for intracellular proteolysis by the 26 S proteasome. Usually, the C-terminal carboxyl group of Ub is linked to an internal lysine side chain of the substrate, and subsequently, multiple ubiquitins are added to form a poly-Ub chain extension.

One of the C19 hydrolases is USP47. USP47 is also known by a number of different names including: "ubiquitin-specific-processing protease 47, ubiquitin thioesterase 47, and deubiquitinating enzyme 47." In the present studies, USP47 has been found to be a substrate for β-TrCP, an F-box protein, that is one of many F-box proteins that specifically recruits substrates for ubiquitin ligation.

Human USP47 has been sequenced and has an amino acid sequence according to the Accession No. NP 060414 (SEQ ID NO:1), the coding sequence is Accession No. NM 017944 (SEQ ID NO:2). To date, three isoforms of USP47 have been identified, Accession No. AAH00226 (SEQ ID NO:3) isolated from retinoblastoma; Accession No. AAH47044 (SEQ ID NO:4) isolated from embryonal carcinomal testis tissue, and Accession No. AAH17795 (SEQ ID NO:5), the partial cDNA sequence is Accession No. BC017795 (SEQ ID NO:11). Another human USP47 isoform, a long isoform has been identified as SEQ ID NO:12. There is an EST that provides the coding sequence for this long isoform. However, there is a frameshift error in this preliminary sequence (SEQ ID NO:13, *Homo sapiens* cDNA clone IMAGE:4815410, Accession No. BC071559).

Human β-TrCP1 has been sequenced and has an amino acid sequence according to Accession No. NP 378663 (SEQ ID NO:6); the β-TrCP1 coding sequence is Accession No. 033637 (SEQ ID NO:7), while a cDNA fragment corresponds to SEQ ID NO:8. This gene encodes a member of the F-box protein family which is characterized by an approximately 40 amino acid motif, the F-box. The F-box proteins constitute one of the four subunits of ubiquitin protein ligase complex called SCFs (SKP1-cullin-F-box), which function in phosphorylation-dependent ubiquitination. The F-box proteins are divided into 3 classes: Fbws containing WD-40 domains, Fb1s containing leucine-rich repeats, and Fbxs containing either different protein-protein interaction modules or no recognizable motifs. The protein encoded by this gene belongs to the Fbws class; in addition to an F-box, this protein contains multiple WD-40 repeats. This protein is homologous to *Xenopus* β-TRCP1, yeast Met30, *Neurospora* Scon2 and *Drosophila* Slimb proteins. It interacts with HIV-1 Vpu and connects CD4 to the proteolytic machinery. It also associates specifically with phosphorylated IkappaBalpha and beta-catenin destruction motifs, most likely functioning in multiple transcriptional programs by activating the NF-kappaB pathway and inhibiting the beta-catenin pathway. The β-TrCP1 is a variant that contains an additional 108 nt fragment within the coding region, as compared to variant 2 (β-TrCP2), and thus encodes an in-frame 36 aa longer isoform than variant β-TrCP2. Pending U.S. patent application Ser. No. 10/968,871 (hereby incorporated by reference in its entirety) describes various aspects of β-TrCP1 and β-TrCP2 including therapeutic and diagnostic methods and assays.

Human β-TrCP2 has been sequenced and has an amino acid sequence according to Accession No. 003930 (SEQ ID NO:9); the coding sequence is Accession No. 003939 (SEQ ID NO: 10).

In accordance with the present invention there may be employed conventional molecular biology, microbiology, protein expression and purification, antibody, and recombinant DNA techniques within the skill of the art. Such techniques are explained fully in the literature. See, e.g., Sambrook et al. (2001) *Molecular Cloning: A Laboratory Manual.* 3$^{rd}$ ed. Cold Spring Harbor Laboratory Press: Cold Spring Harbor, N.Y.; Ausubel et al. eds. (2005) *Current Protocols in Molecular Biology.* John Wiley and Sons, Inc.: Hoboken, N.J.; Bonifacino et al. eds. (2005) *Current Protocols in Cell Biology.* John Wiley and Sons, Inc.: Hoboken, N.J.; Coligan et al. eds. (2005) *Current Protocols in Immunology*, John Wiley and Sons, Inc.: Hoboken, N.J.; Coico et al. eds. (2005) *Current Protocols in Microbiology*, John Wiley and Sons, Inc.: Hoboken, N.J.; Coligan et al. eds. (2005) *Current Protocols in Protein Science*, John Wiley and Sons, Inc.: Hoboken, N.J.; and Enna et al. eds. (2005) *Current Protocols in Pharmacology*, John Wiley and Sons, Inc.: Hoboken, N.J.; *Nucleic Acid Hybridization*, Hames & Higgins eds. (1985); *Transcription And Translation*, Hames & Higgins, eds. (1984); *Animal Cell Culture* Freshney, ed. (1986); *Immobilized Cells And Enzymes*, IRL Press (1986); Perbal, *A Practical Guide To Molecular Cloning* (1984); and Harlow and Lane. *Antibodies: A Laboratory Manual* (Cold Spring Harbor Laboratory Press: 1988).

DEFINITIONS

The following definitions are provided for clarity and illustrative purposes only, and are not intended to limit the scope of the invention.

The term apoptosis means a form of cell death in which a programmed sequence of events leads to the elimination of cells, typically without releasing harmful substances into the surrounding area. Apoptosis plays an important role in developing and maintaining health by eliminating old cells, unnecessary cells, and unhealthy cells. The human body replaces perhaps a million cells a second. Too little or too much apoptosis plays a role in a great many diseases. When programmed cell death does not work properly, cells that should be eliminated may hang around and become immortal. An example of the lack of proper apoptosis occurs for example, in cancer and leukemia. When apoptosis works overly well, it kills too many cells and inflicts tissue damage. Apoptosis is also called programmed cell death or cell suicide. As used herein, apoptosis, cell suicide, and programmed cell death are used interchangeably.

A "β-transducin repeat containing protein" or "β-TrCP" herein is a protein belonging to the family of F-box proteins containing 6-7 repeats of WD40 domains. Synonyms of β-TrCP1/2 include Fbw1a, FWD1a, Fbw1b, FWD1b, FBP1, and Hos. An F-box motif is a stretch of about 40 amino acids identified as being necessary for the interaction of F-box proteins with Skp1. The consensus sequence of an F-box motif is described in Bai et al., Cell, 1996; 86:263-274, hereby incorporated by reference in its entirety. A WD40 domain is a consensus sequence of about 40 amino acid repeats rich in tryptophan (Trp) and aspartic acid (Asp) residues (Neer et al., Nature, 1996; 371:297-300 and references therein, all of which hereby incorporated by reference in their entireties). A β-TrCP is characterized by being capable of a substrate specificity for at least one, preferably at least two, more preferably at least three, and most preferably at least all of phosphorylated Cdc25A, β-catenin, Emil (Guardavaccaro et al., Developmental Cell, 2003; 4:799-812), and IkB (Soldatenkov et al., Cancer Res, 1999; 59:5085-5088). A β-TrCP protein exhibits has at least 50%, 70%, 80%, 90%, 95%, 96%, 97%, 98%, or 99% sequence identity to at least one of the β-TRCP1 amino acid sequence (SEQ ID NO:6) or the β-TrCP2 amino acid sequence (SEQ ID NO:9), and includes functionally equivalent derivates of β-TrCP1 and β-TrCP2 such as mutants, conjugates (including radiolabeled or chemically tagged β-TrCP1/2), fusion proteins, and fragments thereof, which retain the substrate specificity of a β-TrCP. "β-TrCP1/2" means "β-TrCP1 and/or β-TrCP2".

As used herein, a "β-TrCP inhibitor" is a compound or agent reducing β-TrCP1/2 expression, translation, or activity, or increasing β-TrCP1/2 degradation.

A "cell division cycle 25A" or "Cdc25A" protein herein means a protein comprising a peptide sequence corresponding at least to residues 82-88 of human wild-type Cdc25A (SEQ ID NO:14) and encoded by SEQ ID NO:15. Preferably, the peptide sequence comprises the sequence of SEQ ID NO: corresponding to residues 80-93 of human wild-type Cdc25A. To function as a substrate for a β-TrCP, the serine residues corresponding to residues 82 and 88 of SEQ ID NO: must be at least phosphorylated, preferably double phosphorylated. Exemplary Cdc25A fragments useful for testing binding to or ubiquitination by β-TrCP1/2 include-peptides corresponding to residues 73-95 (of SEQ ID NO:14) and residues 80-93 (of SEQ ID NO:14).

A "DNA damaging agent" is a chemical compound or treatment method that induces DNA damage when applied to a cell, including single-strand breaks, double-strand breaks and alkylation. Such agents include, without limitation, ionizing radiation and waves that induce DNA damage, such as γ-irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Contemplated chemotherapeutic agents include alkylating agents such as mitomycin C, adozelesin, cis-platinum, and nitrogen mustard.

"Ubiquitin ligation", "ubiquitination", and "ubiquitinylation" as used herein all refer to the addition of a ubiquitin polypeptide to a protein substrate targeted for degradation.

About or Approximately

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Unless otherwise stated, the term 'about' means within an acceptable error range for the particular value.

Administration

In the case of the present invention, parenteral routes of administration are also possible. Such routes include intravenous, intra-arteriole, intramuscular, intradermal, subcutaneous, intraperitoneal, transmucosal, intranasal, rectal, vaginal, or transdermal routes. If desired, inactivated therapeutic formulations may be injected, e.g., intravascular, intratumor, subcutaneous, intraperitoneal, intramuscular, etc. In a preferred embodiment, the route of administration is oral. Although there are no physical limitations to delivery of the formulation, oral delivery is preferred because of its ease and convenience, and because oral formulations readily accommodate additional mixtures, such as milk and infant formula.

Adjuvant

As used herein, the term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-ttireonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipaimitoyl-sn-glycero-3-hydroxyphosphoryloxy)-ethylamine, BCG (*bacille Calmette-Guerin*) and *Corynebacterium parvum*. Preferably, the adjuvant is pharmaceutically acceptable.

Amplification

"Amplification" of DNA as used herein denotes the use of polymerase chain reaction (PCR) to increase the concentration of a particular DNA sequence within a mixture of DNA sequences. For a description of PCR see Saiki et al., Science 1988, 239:487.

Carrier

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

Coding Sequence or A Sequence Encoding an Expression Product

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

Dosage

The dosage of the therapeutic formulation will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. In some cases, oral administration will require a higher dose than if administered intravenously.

Expression Construct

By "expression construct" is meant a nucleic acid sequence comprising a target nucleic acid sequence or sequences whose expression is desired, operatively associated with expression control sequence elements which provide for the proper transcription and translation of the target nucleic acid sequence(s) within the chosen host cells. Such sequence elements may include a promoter and a polyadenylation signal. The "expression construct" may further comprise "vector sequences." By "vector sequences" is meant any of several nucleic acid sequences established in the art which have utility in the recombinant DNA technologies of the invention to facilitate the cloning and propagation of the expression constructs including (but not limited to) plasmids, cosmids, phage vectors, viral vectors, and yeast artificial chromosomes.

Expression constructs of the present invention may comprise vector sequences that facilitate the cloning and propagation of the expression constructs. A large number of vectors, including plasmid and fungal vectors, have been described for replication and/or expression in a variety of eukaryotic and prokaryotic host cells. Standard vectors useful in the current invention are well known in the art and include (but are not limited to) plasmids, cosmids, phage vectors, viral vectors, and yeast artificial chromosomes. The vector sequences may contain a replication origin for propagation in *E. coli*; the SV40 origin of replication; an ampicillin, neomycin, or puromycin resistance gene for selection in host cells; and/or genes (e.g., dihydrofolate reductase gene) that amplify the dominant selectable marker plus the gene of interest.

Express and Expression

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cells genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

Expression System

The term "expression system" means a host cell and compatible vector under suitable conditions, e.g. for the expression of a protein coded for by foreign DNA carried by the vector and introduced to the host cell.

Gene or Structural Gene

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operatively associated with" expression control sequences in a cell when RNA polymerase transcribes the coding sequence into RNA, particularly mRNA, which is then trans-RNA spliced (if it contains introns) and translated into the protein encoded by the coding sequence.

The term "expression control sequence" refers to a promoter and any enhancer or suppression elements that combine to regulate the transcription of a coding sequence. In a preferred embodiment, the element is an origin of replication.

Heterologous

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. For example, the present invention includes chimeric DNA molecules that comprise a DNA sequence and a heterologous DNA sequence which is not part of the DNA sequence. A heterologous expression regulatory element is such an element that is operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed.

Homologous

The term "homologous" as used in the art commonly refers to the relationship between nucleic acid molecules or proteins that possess a "common evolutionary origin," including nucleic acid molecules or proteins within superfamilies (e.g., the immunoglobulin superfamily) and nucleic acid molecules or proteins from different species (Reeck et al., *Cell* 1987; 50: 667). Such nucleic acid molecules or proteins have sequence homology, as reflected by their sequence similarity, whether in terms of substantial percent similarity or the presence of specific residues or motifs at conserved positions.

Host Cell

The term "host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells can further be used for screening or other assays that are described infra. Host cells may be cultured in vitro or one or more cells in a non-human animal (e.g. a transgenic animal or a transiently transfected animal). Suitable host cells include but are not limited to *Streptomyces* species and *E. Coli*.

Immune Response

An "immune response" refers to the development in the host of a cellular and/or antibody-mediated immune response to a composition or vaccine of interest. Such a response usually consists of the subject producing antibodies, B cells, helper T cells, suppressor T cells, and/or cytotoxic T cells directed specifically to an antigen or antigens included in the composition or vaccine of interest.

Isolated

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, a PCR product, an isolated mRNA, a cDNA, or a restriction fragment. Isolated nucleic acid molecules also include, for example, sequences inserted into plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated protein may be associated with other proteins or nucleic acids, or both, with which it associates in the cell, or with cellular membranes if it is a membrane-associated protein.

Mutant

As used herein, the terms "mutant" and "mutation" refer to any detectable change in genetic material (e.g., DNA) or any process, mechanism, or result of such a change. This includes gene mutations, in which the structure (e.g., DNA sequence) of a gene is altered, any gene or DNA arising from any mutation process, and any expression product (e.g., protein or enzyme) expressed by a modified gene or DNA sequence. As used herein, the term "mutating" refers to a process of creating a mutant or mutation.

Nucleic Acid Hybridization

The term "nucleic acid hybridization" refers to anti-parallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See *Molecular Biology of the Cell*, Alberts et al., $3^{rd}$ ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M $NaHPO_4$, 7% SDS, 1 mM EDTA at 65° C., followed by washing in 0.1×SSC/0.1% SDS at 68° C. (where 1×SSC is 0.15M NaCl, 0.15M Na citrate) or for oligonucleotide molecules washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos)). Accordingly, the term "high stringency hybridization" refers to a combination of solvent and temperature where two strands will pair to form a "hybrid" helix only if their nucleotide sequences are almost perfectly complementary (see *Molecular Biology of the Cell*, Alberts et al., $3^{rd}$ ed., New York and London: Garland Publ., 1994, Ch. 7).

Conditions of intermediate or moderate stringency (such as, for example, an aqueous solution of 2×SSC at 65° C.; alternatively, for example, hybridization to filter-bound DNA in 0.5 M $NaHPO_4$, 7% SDS, 1 mM EDTA at 65° C., and washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA and length and base composition of the probe, and are normally determined empirically in preliminary experiments, which are routine (see Southern, *J. Mol. Biol.* 1975; 98: 503; Sambrook et al., *Molecular Cloning: A Laboratory Manual*, $2^{nd}$ ed., vol. 2, ch. 9.50, CSH Laboratory Press, 1989; Ausubel et al. (eds.), 1989, *Current Protocols in Molecular Biology*, Vol. I, Green Publishing Associates, Inc., and John Wiley & Sons, Inc., New York, at p. 2.10.3).

As used herein, the term "standard hybridization conditions" refers to hybridization conditions that allow hybridization of sequences having at least 75% sequence identity. According to a specific embodiment, hybridization conditions of higher stringency may be used to allow hybridization of only sequences having at least 80% sequence identity, at least 90% sequence identity, at least 95% sequence identity, or at least 99% sequence identity.

Nucleic acid molecules that "hybridize" to any desired nucleic acids of the present invention may be of any length. In one embodiment, such nucleic acid molecules are at least 10, at least 15, at least 20, at least 30, at least 40, at least 50, and at least 70 nucleotides in length. In another embodiment, nucleic acid molecules that hybridize are of about the same length as the particular desired nucleic acid.

Nucleic Acid Molecule

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

Orthologs

As used herein, the term "orthologs" refers to genes in different species that apparently evolved from a common ancestral gene by specification. Normally, orthologs retain the same function through the course of evolution. Identification of orthologs can provide reliable prediction of gene function in newly sequenced genomes. Sequence comparison algorithms that can be used to identify orthologs include without limitation BLAST, FASTA, DNA Strider, and the GCG pileup program. Orthologs often have high sequence similarity. The present invention encompasses all orthologs of the desired protein.

Operatively Associated

By "operatively associated with" is meant that a target nucleic acid sequence and one or more expression control sequences (e.g., promoters) are physically linked so as to permit expression of the polypeptide encoded by the target nucleic acid sequence within a host cell.

Patient or Subject

"Patient" or "subject" refers to mammals and includes human and veterinary subjects.

Percent Sequence Similarity or Percent Sequence Identity

The terms "percent (%) sequence similarity", "percent (%) sequence identity", and the like, generally refer to the degree of identity or correspondence between different nucleotide sequences of nucleic acid molecules or amino acid sequences of proteins that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, *Proc. Natl. Acad. Sci. USA* 1990, 87:2264, modified as in Karlin and Altschul, *Proc. Natl. Acad. Sci. USA* 1993, 90:5873-5877. Such an algorithm is incorporated into the NBLAST and XBLAST programs of Altschul et al., *J. Mol. Biol.* 1990; 215: 403. BLAST nucleotide searches can be performed with the NBLAST program, score=100, wordlength=12, to obtain nucleotide sequences homologous to sequences of the invention. BLAST protein searches can be performed with the XBLAST program, score=50, wordlength=3, to obtain amino acid sequences homologous to protein sequences of the invention. To obtain gapped alignments for comparison purposes, Gapped BLAST can be utilized as described in Altschul et al., *Nucleic Acids Res.* 1997, 25:3389. Alternatively, PSI-Blast can be used to perform an iterated search that detects distant relationship between molecules. See Altschul et al. (1997) supra. When utilizing BLAST, Gapped BLAST, and PSI-Blast programs, the default parameters of the respective programs (e.g., XBLAST and NBLAST) can be used. See ncbi.nim.nih.gov/BLAST/ on the WorldWideWeb. Another non-limiting example of a mathematical algorithm utilized for the comparison of sequences is the algorithm of Myers and Miller, *CABIOS* 1988; 4: 1-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In a preferred embodiment, the percent identity between two amino acid sequences is determined using the algorithm of Needleman and Wunsch (*J. Mol. Biol.* 1970, 48:444-453), which has been incorporated into the GAP program in the GCG software package (Accelrys, Burlington, Mass.; available at accelrys.com on the WorldWideWeb), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

In addition to the cDNA sequences encoding various desired proteins, the present invention further provides polynucleotide molecules comprising nucleotide sequences having certain percentage sequence identities to any of the aforementioned sequences. Such sequences preferably hybridize under conditions of moderate or high stringency as described above, and may include species orthologs.

Pharmaceutically Acceptable

When formulated in a pharmaceutical composition, a therapeutic compound such as an USP47 inhibitor can be admixed with a pharmaceutically acceptable carrier or excipient. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human.

Pharmaceutically Acceptable Derivative

The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives. Preferred pharmaceutically acceptable derivatives are salts, solvates, esters, carbamates, and phosphate esters. Particularly preferred pharmaceutically acceptable derivatives are salts, solvates, and esters. Most preferred pharmaceutically acceptable derivatives are salts and esters.

Pharmaceutical Compositions and Administration

While it is possible to use a composition provided by the present invention for therapy as is, it may be preferable to administer it in a pharmaceutical formulation, e.g., in admixture with a suitable pharmaceutical excipient, diluent or carrier selected with regard to the intended route of administration and standard pharmaceutical practice. Accordingly, in one aspect, the present invention provides a pharmaceutical composition or formulation comprising at least one active composition, or a pharmaceutically acceptable derivative thereof, in association with a pharmaceutically acceptable excipient, diluent and/or carrier. The excipient, diluent and/or carrier must be "acceptable" in the sense of being compatible with the other ingredients of the formulation and not deleterious to the recipient thereof.

The compositions of the invention can be formulated for administration in any convenient way for use in human or veterinary medicine. The invention therefore includes within its scope pharmaceutical compositions comprising a product of the present invention that is adapted for use in human or veterinary medicine, including treating food allergies and related immune disorders.

In a preferred embodiment, the pharmaceutical composition is conveniently administered as an oral formulation. Oral dosage forms are well known in the art and include tablets, caplets, gelcaps, capsules, and medical foods. Tablets, for example, can be made by well-known compression techniques using wet, dry, or fluidized bed granulation methods.

Such oral formulations may be presented for use in a conventional manner with the aid of one or more suitable excipients, diluents, and carriers. Pharmaceutically acceptable excipients assist or make possible the formation of a dosage form for a bioactive material and include diluents, binding agents, lubricants, glidants, disintegrants, coloring agents, and other ingredients. Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may be also used. An excipient is pharmaceutically acceptable if, in addition to performing its desired function, it is non-toxic, well tolerated upon ingestion, and does not interfere with absorption of bioactive materials.

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

The term "therapeutically effective amount" is used herein to mean an amount or dose sufficient to modulate, e.g., decrease the level of USP47 activity e.g., by about 10 percent, preferably by about 50 percent, and more preferably by about 90 percent. Preferably, a therapeutically effective amount is sufficient to cause an improvement in a clinically significant condition in the host following a therapeutic regimen involving one or more USP47 inhibitors. The concentration or amount of the active ingredient depends on the desired dosage and administration regimen, as discussed below. Suitable dosages may range from about 0.01 mg/kg to about 100 mg/kg of body weight per day, week, or month. The pharmaceutical compositions may also include other biologically active compounds.

According to the invention, a therapeutically effective amount of the USP47 inhibitor can be formulated in a pharmaceutical composition of the invention to be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. Optionally, the USP47 inhibitor can be formulated together with an DNA damaging agent such as an alkylating agent.

In another embodiment, the active ingredient can be delivered in a vesicle, in particular a liposome (see Langer, Science, 1990; 249:1527-1533; Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.).

In yet another embodiment, the therapeutic compound(s) can be delivered in a controlled release system. For example, a polypeptide may be administered using intravenous infusion with a continuous pump, in a polymer matrix such as poly-lactic/glutamic acid (PLGA), a pellet containing a mixture of cholesterol and the active ingredient (Silastic®; Dow Corning, Midland, Mich.; see U.S. Pat. No. 5,554,601) implanted subcutaneously, an implantable osmotic pump, a transdermal patch, liposomes, or other modes of administration.

The effective amounts of compounds of the present invention include doses that partially or completely achieve the desired therapeutic, prophylactic, and/or biological effect. The actual amount effective for a particular application depends on the condition being treated and the route of administration. The effective amount for use in humans can be determined from animal models. For example, a dose for humans can be formulated to achieve circulating and/or gastrointestinal concentrations that have been found to be effective in animals.

Kits

In certain embodiments, the invention provides a kit for screening for an agent useful for inhibiting USP47 activity, comprising: a USP47 protein, at least one β-TrCP protein, a means for detecting binding between the USP47 and β-TrCP protein, packaged in association with instructions teaching one or more of the methods described herein.

Polynucleotide or Nucleotide Sequence

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphiorothiioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radio-isotopes, fluorescent molecules, biotin, and the like.

Promoter

The promoter sequences may be endogenous or heterologous to the host cell to be modified, and may provide ubiquitous (i.e. +, expression occurs in the absence of an apparent external stimulus) or inducible (i.e., expression only occurs in presence of particular stimuli) expression. Promoters which may be used to control gene expression include, but are not limited to, cytomegalovirus (CMV) promoter (U.S. Pat. No. 5,385,839 and No. 5,168,062), the SV40 early promoter region (Benoist and Chambon, Nature 1981; 290:304-310), the promoter contained in the 3' long terminal repeat of Rous sarcoma virus (Yamamoto, et al., Cell 1980; 22:787-797), the herpes thymidine kinase promoter (Wagner et al., Proc. Natl. Acad. Sci. USA 1981; 78: 1441-1445), the regulatory sequences of the metallothionein gene (Brinster et al., Nature 1982; 296:39-42); prokaryotic promoters such as the alkaline phosphatase promoter, the trp-lac promoter, the bacteriophage lambda $P_L$ promoter, the T7 promoter, the beta-lactamase promoter (Villa-Komaroff, et al., Proc. Natl. Acad. Sci. USA 1978; 75:3727-3731), or the tac promoter (DeBoer, et al., Proc. Natl. Acad. Sci. USA 1983; 80:21-25); see also "Useful proteins from recombinant bacteria" in Scientific American 1980; 242:74-94; promoter elements from yeast or other fungi such as the Gal4 promoter, the ADC (alcohol dehydrogenase) promoter, and the PGK (phosphoglycerol kinase) promoter.

Small Molecule

The term "small molecule" refers to a compound that has a molecular weight of less than about 2000 Daltons, less than about 1000 Daltons, or less than about 500 Daltons. Small molecules, without limitation, may be, for example, nucleic acids, peptides, polypeptides, peptide nucleic acids, peptidomimetics, carbohydrates, lipids, or other organic (carbon containing) or inorganic molecules and may be synthetic or naturally occurring or optionally derivatized. Such small molecules may be a therapeutically deliverable substance or may be further derivatized to facilitate delivery or targeting.

Substantially Homologous or Substantially Similar

In a specific embodiment, two DNA sequences are "substantially homologous" or "substantially similar" when at least about 80%, and most preferably at least about 90% or 95% of the nucleotides match over the defined length of the DNA sequences, as determined by sequence comparison algorithms, such as BLAST, FASTA, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar. Preferably, the amino acids are functionally identical. Preferably, the similar or homologous sequences are identified by alignment using, for example, the GCG (Genetics Computer Group, Program Manual for the GCG Package, Version 10, Madison, Wis.) pileup program, or any of the programs described above (BLAST, FASTA, etc.).

Substantially Identical

By "substantially identical" is meant a polypeptide or nucleic acid molecule exhibiting at least 80%, more preferably at least 90%, and most preferably at least 95% identity in comparison to a reference amino acid or nucleic acid sequence. For polypeptides, the length of sequence comparison will generally be at least 20 amino acids, preferably at least 30 amino acids, more preferably at least 40 amino acids, and most preferably at least 50 amino acids. For nucleic acid molecules, the length of sequence comparison will generally be at least 60 nucleotides, preferably at least 90 nucleotides, and more preferably at least 120 nucleotides.

The degree of sequence identity between any two nucleic acid molecules or two polypeptides may be determined by sequence comparison and alignment algorithms known in the art, including but not limited to BLAST, FASTA, DNA Strider, and the GCG Package (Madison, Wis.) pileup program (see, for example, Gribskov and Devereux *Sequence Analysis Primer* (Stockton Press: 1991) and references cited therein). The percent similarity between two nucleotide sequences may be determined, for example, using the Smith-Waterman algorithm as implemented in the BESTFIT software program using default parameters.

Therapeutically Effective Amount

A "therapeutically effective amount" means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

Therapeutically or Prophylactically Effective Amount of an Antibody

The compositions of the invention may include a "therapeutically effective amount" or a "prophylactically effective amount" of an antibody or antigen-binding portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Transfection

By "transfection" is meant the process of introducing one or more of the expression constructs of the invention into a host cell by any of the methods well established in the art, including (but not limited to) microinjection, electroporation, liposome-mediated transfection, calcium phosphate-mediated transfection, or virus-mediated transfection.

Treating or Treatment

"Treating" or "treatment" of a state, disorder or condition includes:

(1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms.

The benefit to a subject to be treated is either statistically significant or at least perceptible to the patient or to the physician.

Vaccine

As used herein, the term "vaccine" refers to a composition comprising a cell or a cellular antigen, and optionally other pharmaceutically acceptable carriers, administered to stimulate an immune response in an animal, preferably a mammal, most preferably a human, specifically against the antigen and preferably to engender immunological memory that leads to mounting of a protective immune response should the subject encounter that antigen at some future time. Vaccines often comprise an adjuvant.

Variant

The term "variant" may also be used to indicate a modified or altered gene, DNA sequence, enzyme, cell, etc., i.e., any kind of mutant.

Vector, Cloning Vector and Expression Vector

The terms "vector", "cloning vector" and "expression vector" refer to the vehicle by which DNA can be introduced into a host cell, resulting in expression of the introduced sequence. In one embodiment, vectors comprise a promoter and one or more control elements (e.g., enhancer elements) that are heterologous to the introduced DNA but are recognized and used by the host cell. In another embodiment, the sequence that is introduced into the vector retains its natural promoter that may be recognized and expressed by the host cell (Boniann et al., J. Bacteriol. 1996; 178:1216-1218).

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct". A common type of vector is a "plasmid", which generally is a self-contained molecule of double-stranded DNA, usually of bacterial origin, that can readily accept additional (foreign) DNA and which can readily be introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes. Vector constructs may be produced using conventional molecular biology and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); F. M. Ausubel et al. (eds.), Current Protocols in Molecular Biology, John Wiley & Sons, Inc. (1994).

The abbreviations in the specification correspond to units of measure, techniques, properties or compounds as follows: "min" means minutes, "h" means hour(s), "µL" means microliter(s), "mL" means milliliter(s), "mM" means millimolar, "M" means molar, "mmole" means millimole(s), "kb" means kilobase, "bp" means base pair(s), and "IU" means International Units. "Polymerase chain reaction" is abbreviated PCR; "Reverse transcriptase polymerase chain reaction" is abbreviated RT-PCR; "Estrogen receptor" is abbreviated ER; "DNA binding domain" is abbreviated DBD; "Untranslated region" is abbreviated UTR; "Sodium dodecyl sulfate" is abbreviated SDS; and "High Pressure Liquid Chromatography" is abbreviated HPLC.

Expression of USP47 Polypeptides and β-TrCP1/2 and β-TrCP1/2 Substrates

For the screening and evaluation of compounds for their ability to modulate the USP47 interaction with β-TRCP1/2 or other β-TrCP substrates, both in vitro (including reconstituted systems) and in vivo systems (including cellular systems and transgenic animals) can be used. Regardless of the screening or testing system of choice, various expression methods can be employed to provide the protein components or cellular/transgenic animals to be used in the method.

A wide variety of host/expression vector combinations (i.e., expression systems) may be employed in expressing DNA sequences for USP47, β-TrCP1 or fragments or mutants thereof, β-TrCP2 or fragments or mutants thereof, Cdc25A or fragments or mutants thereof, Skp1, Cul1, β-catenin, Emi1, IκB-α, IκB-β, IκB-ε, and other components to be included. These may be co-expressed from the same vector, expressed from different vectors, or one may be expressed while the other one is added externally to the screening or evaluation system. Useful expression vectors, for example, may consist of segments of chromosomal, non chromosomal and synthetic DNA sequences. Suitable vectors include derivatives of SV40 and known bacterial plasmids, e.g., E. coli plasmids col E1, pCR1, pBR322, pMal-C2, pET, pGEX (Smith et al., Gene, 1988; 67:31-40), pMB9 and their derivatives, plasmids such as RP4; phage DNAS, e.g., the numerous derivatives of phage 1, e.g., NM989, and other phage DNA, egg., M13 and filamentous single stranded phage DNA; yeast plasmids such as the 2 m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. In a preferred embodiment, various tumor cells lines can be used in expression systems of the invention.

Yeast expression systems can also be used according to the invention to express any protein of interest. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, Kpn1, and HindIII cloning site, N-terminal peptide purified with ProBond resin and cleaved with enterokinase; Invitrogen), to mention just two, can be employed according to the invention.

Expression of the protein or polypeptide may be controlled by any promoter/enhancer element known in the art, but these regulatory elements must be functional in the host selected for expression. Promoters which may be used to control gene expression include, but are not limited to, cytomegalovirus (CMV) promoter (U.S. Pat. No. 5,385,839 and No. 5,168,062), the SV40 early promoter region (Benoist and Chambon, Nature, 1981; 290:304-310), the promoter contained in the 3' long terminal repeat of Rous sarcoma virus (Yamamoto, et al., Cell, 1980; 22:787-797), the herpes thymidine kinase promoter (Wagner et al., Proc. Natl. Acad. Sci. U.S.A., 1981; 78: 1441-1445), the regulatory sequences of the metallothionein gene (Brinster et al., Nature, 1982; 296:39 42); prokaryotic expression vectors such as the β-lactamase promoter (Villa-Komaroff, et al., Proc. Natl. Acad. Sci. U.S.A., 1978; 75:3727-3731), or the tac promoter (DeBoer, et. al., Proc. Natl. Acad. Sci. U.S.A., 1983; 80:21-25); see also "Useful proteins from recombinant bacteria" in Scientific American, 1980; 242:74-94; promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Mogram et al., Nature, 1985; 315:338-340; Kollias et al., Cell, 1986; 46:89-94), hematopoietic stem cell differentiation factor promoters, erythropoietin receptor promoter (Maouche et al., Blood, 1991; 15:2557), etc.

Preferred vectors, particularly for cellular assays in vitro and in vivo, are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional or mutant protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques, 1992; 7:980-990). Preferably, the viral vectors are replication defective, that is, they are unable to replicate autonomously in the target cell. Preferably, the replication defective virus is a minimal virus, i.e., it retains only the sequences of its genome which are necessary for encapsidating the genome to produce viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci., 1991; 2:320-330), defective herpes virus vector lacking a glycoprotein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenoviral vector, such as the vector described by Stratford-Perricaudet et al. (J. Clin. Invest., 1992; 90:626-630; see also La Salle et al., Science, 1993; 259:988-990); and a defective adeno-associated virus vector (Samulski et al., J. Virol., 1987; 61:3096-3101; Samulski et al., J. Virol., 1989; 63:3822-3828; Lebkowski et al., Mol. Cell. Biol., 1988; 8:3988-3996).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo. Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (see, e.g., Wilson, Nature Medicine 1995). In that regard, it is advantageous to employ a viral vector that is engineered to express a minimal number of antigens.

It is also possible to introduce the vector in vivo as a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (see, e.g., Wu et al., J. Biol. Chem., 1992; 267:963-967; Wu and Wu, J. Biol. Chem., 1988; 263:14621-14624; Harmut et al., Canadian Patent Application No. 2,012,311, filed Mar. 15, 1990; Williams et al., Proc. Natl. Acad. Sci. USA, 1991; 88:2726-2730). Receptor-mediated DNA delivery approaches can also be used (Curiel et al., Hum. Gene Ther., 1992; 3:147-154; Wu and Wu, J. Biol. Chem., 1987; 262:4429-4432). U.S. Pat. Nos. 5,580,859 and 5,589,466 disclose delivery of exogenous DNA sequences, free of transfection facilitating agents, in a mammal. A relatively low voltage, high efficiency in vivo DNA transfer technique, termed electrotransfer, has also been described (Mir et al., C. P. Acad. Sci., 1998; 321:893; WO 99/01157, WO99/01158; WO99/01175).

Another option is to transcribe and translate cDNA sequences in vitro. Various commercial systems are available for such techniques, including the TNT Quick Coupled Transcription/Translation System with Transcend™ (Promega, Madison, Wis.). For in vitro production of labeled or modified peptides or proteins, labeled or chemically modified amino acid precursors such as, e.g., $^{35}$S-methionine or phosphoserine, can be added to the translation system.

Transgenic Animals

Transgenic mammals can be prepared for evaluating the interaction of human USP47 and β-TrCP1/2, or any other β-TrCP1/2 substrates. Such mammals provide excellent models for screening or testing drug candidates, i.e., USP47 inhibitors such as exemplary siRNAs SEQ ID NO:16 and SEQ ID NO:17. Thus, human USP47 "knock-in" mammals can be prepared for evaluating the molecular biology of this system in greater detail than is possible with human subjects. In one embodiment, the animal can be double-transgenic, in that both human USP47 and human β-TrCP1/2 is expressed in the transgenic animal. It is also possible to evaluate compounds or diseases in "knock-out" animals, e.g., to identify a compound that can compensate for a defect in USP47. Both technologies permit manipulation of single units of genetic information in their natural position in a cell genome and to examine the results of that manipulation in the background of a terminally differentiated organism. Transgenic mammals can be prepared by any method, including but not limited to modification of embryonic stein (ES) cells and heteronuclear injection into blast cells.

A "knock-in" mammal is a mammal in which an endogenous gene is substituted with a heterologous gene (Roemer et al., New Biol., 1991, 3:331). Preferably, the heterologous gene is "knocked-in" to a locus of interest, either the subject of evaluation (in which case the gene may be a reporter gene, see Elefanty et al., Proc Natl Acad Sci USA, 1998; 95:11897) of expression or function of a homologous gene, thereby linking the heterologous gene expression to transcription from the appropriate promoter. This can be achieved by homologous recombination, transposon (Westphal and Leder, Curr Biol, 1997; 7:530), using mutant recombination sites (Araki et al., Nucleic Acids Res, 1997; 25:868) or PCR (Zhang and Henderson, Biotechniques, 1998; 25:784).

A "knock-out mammal" is a mammal (e.g., mouse) that contains within its genome a specific gene that has been inactivated by the method of gene targeting (see, e.g., U.S. Pat. Nos. 5,777,195 and 5,616,491). A knockout mammal includes both a heterozygote knockout (i.e., one defective allele and one wild type allele) and a homozygous mutant. Preparation of a knockout mammal requires first introducing a nucleic acid construct that will be used to suppress expression of a particular gene into an undifferentiated cell type termed an embryonic stem cell. This cell is then injected into a mammalian embryo. A mammalian embryo with an integrated cell is then implanted into a foster mother for the duration of gestation. Zhou, et al. (Genes and Development, 1995; 9:2623 34) describes PPCA knock out mice. The term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise (1) a full or partial sequence of one or more exons and/or introns of the gene to be suppressed, (2) a full or partial promoter sequence of the gene to be suppressed, or (3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo. Generally, for homologous recombination, the DNA will be at least about 1 kilobase (kb) in length and preferably 3-4 kb in length, thereby providing sufficient complementary sequence for recombination when the knockout construct is introduced into the genomic DNA of the ES cell. Double knock-out mammals can be generated by repeating the procedures set forth herein for generating each knock-in or knock-out construct, or by breeding to mammals, each with a single gene knocked out, to each other, and screening for those with the double knockout genotype. Regulated knockout animals can be prepared using various systems, such as the tet-repressor system (see U.S. Pat. No. 5,654,168) or the Cre-Lox system (see U.S. Pat. No. 4,959, 317 and No. 5,801,030). The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

In another series of embodiments, transgenic animals are created in which (i) a human USP47 and/or β-TrCP1/2 is stably inserted into the genome of the transgenic animal; and/or (ii) the corresponding endogenous genes are inactivated and replaced with their human counterparts (see, e.g., Coffman, Semin. Nephrol., 1997; 17:404; Esther et al., Lab. Invest., 1996; 74:953; Murakami et al., Blood Press. Suppl., 1996; 2:36). Such animals can be treated with candidate compounds and monitored for neuronal development, neurodegeneration, or efficacy of a candidate therapeutic compound.

Antibodies to USP47 and USP47 Substrates

As described in the Examples, various antibodies useful for detecting USP47, binding of USP47 to β-TrCP1/2 substrates, or other interactions including Cdc25A, have been produced, some of which are available commercially. Such antibodies may be used in immunoblotting or immunoprecipitation techniques to study binding of USP47 to β-TrCP1/2 or to another one of its substrates, to detect ubiquitinated Cdc25A, to inhibit interaction between USP47 and β-TrCP1/2 or one of its other substrates, or for other purposes in the screening and treatment methods described herein. Additional antibodies with different specificity or other particular properties may also be prepared. Antibodies useful for these purposes include but are not limited to polyclonal, monoclonal, chimeric, single chain, Fab fragments, and Fab expression library.

Various procedures known in the art may be used for the production of polyclonal antibodies. For example, various host animals can be immunized by injection with the antigenic polypeptide, including but not limited to rabbits, mice, rats, sheep, goats, etc. For preparation of monoclonal antibodies, any technique that provides for the production of antibody molecules by continuous cell lines in culture may be used. These include but are not limited to the hybridoma technique originally developed by Kohler and Milstein (Nature, 1975; 256:495-497), as well as the trioma technique, the human B-cell hybridoma technique (Kozbor et al., Immunology Today, 1983; 4:72, Cote et al., Proc. Natl. Acad. Sci. U.S.A., 1983, 80:2026-2030), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (International Patent Publication No. WO 89/12690, published 28 Dec., 1989).

According to the invention, techniques described for the production of single chain antibodies (U.S. Pat. Nos. 5,476, 786 and 5,132,405 to Huston; U.S. Pat. No. 4,946,778) can be adapted to produce polypeptide-specific single chain antibodies. Indeed, these genes can be delivered for expression in vivo to, e.g., express an antibody inhibiting USP47 interaction with β-TrCP1/2. An additional embodiment of the invention utilizes the techniques described for the construction of Fab expression libraries (Huse et al., Science, 1989; 246: 1275-1281) to allow rapid and easy identification of monoclonal Fab fragments with the desired specificity for a PTPN11 polypeptide, or its derivatives, or analogs.

Antibody fragments which contain the idiotype of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Screening

A "test substance" or "test compound" is a chemically defined compound or mixture of compounds (as in the case of a natural extract or tissue culture supernatant), whose ability to modulate USP47 activity may be defined by various assays. A "test substance" is also referred to as a "candidate drug" or "candidate compound" in the present description.

Test substances may be screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from, e.g., Pan Laboratories (Bothell, Wash.) or MycoSearch (NC), or are readily producible. Additionally, natural and synthetically produced libraries and compounds are readily modified through conventional chemical, physical, and biochemical means (Blondelle et al., TIBTech, 1996; 14:60).

A modulatory effect may be determined by an in vitro method using a recombinant USP47 reporter gene promoter activity system. Reporter genes for use in the invention encode detectable proteins, include, but are by no means limited to, chloramphenicol transferase (CAT), β-galactosidase (β-gal), luciferase, green fluorescent protein (GFP) and derivatives thereof, yellow fluorescent protein and derivatives thereof, alkaline phosphatase, other enzymes that can be adapted to produce a detectable product, and other gene products that can be detected, e.g., immunologically (by immunoassay).

A screen according to the invention involves detecting expression of the reporter gene by the host cell when contacted with a test substance. If there is no change in expression of the reporter gene, the test substance is not an effective modulator. If reporter gene expression is modified, in particular reduced or eliminated, the test substance has modulated, e.g., inhibited, USP47-mediated gene expression, and is thus a candidate for development as a USP47 inhibitor, and as a β-TrCP1/2 modulator (increases β-TrCP1/2 substrate levels, inducing apoptosis) for use as a tumor sensitizing agent. The reporter gene assay system described herein may be used in a high-throughput primary screen for antagonists, or it may be used as a secondary functional screen for candidate compounds identified by a different primary screen, e.g., a binding assay screen that identifies compounds that modulate USP47 transcription activity.

Potential drugs may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time (see, e.g., U.S. Pat. Nos. 5,585,277, 5,679,582, and 6,020,141). Such high-throughput screening methods are particularly preferred. Alternatively, simple reporter-gene based cell assays such as the one described here are also highly desirable.

Intact cells or whole animals expressing genes encoding at least one of USP47, β-TrCP1/2 and Cdc25A, and optionally also any of the remaining components of an SCF complex, can be used in screening methods to identify candidate drugs. In one series of embodiments, a permanent cell line is established. Alternatively, cells are transiently programmed to express a USP47 gene by introduction of appropriate DNA or mRNA. As described herein, transgenic animals can also be used to screen for or study USP47 inhibitors.

Identification of candidate substances can be achieved using any suitable assay, including without limitation (i) assays that measure selective binding of test compounds to USP47, to the USP47 binding site on β-TrCP1/2 or another one of its substrates (ii) assays that measure the ability of a test substance to modify (e.g., inhibit) a measurable activity or function of USP47, (iii) assays that measure the ability of a substance to modify (i.e., inhibit) the transcriptional activity of sequences derived from the promoter (i.e., regulatory) regions of the USP47 gene; and (iv) assays that modulate (e.g., promote) the degradation of USP47 proteins. Examples of USP47 inhibitors include siRNAs SEQ ID NO:16 and SEQ ID NO:17.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways, e.g. to enhance their proteolytic stability.

RNA Interference (RNAi or siRNA)

Another technique of interest for therapeutic purposes is based on the same principles employed for interfering with USP47 translation in a cellular system, namely siRNA technology. Particularly, expression of selected genes can be suppressed in human cells by transfecting with exogenous, short RNA duplexes (siRNA) where one strand corresponds to a target region of the mRNA, i.e., EST of interest (Elbashir et al., Nature, 2001; 411:494-498). The siRNA molecules are typically greater than 19 duplex nucleotides, and upon entry into the cell, siRNA causes the degradation of single-stranded (ssRNAs) RNAs of identical sequences, including endogenous mRNAs. siRNA is more potent than standard antisense technology since it acts through a catalytic mechanism. Effective strategies to deliver siRNAs to target cells in cell culture include physical or chemical transfection. An alternative strategy uses the endogenous expression of siRNAs by various Pol III promoter expression cassettes that allow transcription of functional siRNAs or their precursors (Scherr et al., Curr. Med. Chem., 2003; 10(3):245-56). Recently, the RNA-polymerase III dependent promoter (H1-RNA promoter) was inserted in the lentiviral genome to drive the expression of a small hairpin RNA (shRNA) against enhanced green fluorescent protein (Abbas-Turki et al., Hum. Gene Ther., 2002; 13(18):2197-201). siRNA can also be delivered in a viral vector derived, e.g., from a lentivirus (Tiscornia et al., Proc. Natl. Acad. Sci. U.S.A., 2003; 100: 1844-8). For review articles, see Hannon, Nature, 2002; 418: 244-51 and Bernstein et al., RNA, 2001; 7(11):1509-21. This technology also has been described in vitro in cultured mammalian neurons in Krickevsky and Kosik, Proc. Natl. Acad. Sci. USA, 2002; 99(18):11926-9. siRNA technology is also being used to make transgenic animals (Cornell et al., Nat. Struct. Biol., 2003; 10(2):91-2). RNA is described in Publication Nos. WO 99/49029 and WO 01/70949.

Exemplary siRNA duplexes suitable for USP47 are described. The siRNAs used correspond to duplexes 1 and 4 from Dharmacon (Lafayette, Colo.). Oligo 1 uses the sequence (sense strand) GGACUUGACUCUCA-CAGUAUU (SEQ ID NO:16) and oligo 2 uses the sequence (sense strand) GCAACGAUUUCUCCAAUGAUU (SEQ ID NO:17). siRNAs SEQ ID NO:16 and SEQ ID NO:17 are examples of inhibitors of USP47.

EXAMPLES

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials & Methods

The following describes the materials and methods employed in Examples 1-3.

Cells. HeLa (human carcinoma; obtained from ATCC) or U2OS (human osteosarcoma) cells are used in the Examples. Cell culture is conducted essentially as described in Donzelli et al. (Embo J, 2002; 21:4875-84). Cells are grown at 37° C. in a 5% $CO_2$ atmosphere in Dulbecco's modified Eagle's medium (Euroclone) supplemented with 10% bovine calf serum (Hyclone) and 2 mM L-glutamine (Euroclone), or in DMEM containing 5% FCS.

Cell Synchronizations. This is conducted essentially as described in Donzelli et al. (2002), supra. Briefly, to obtain HeLa cells arrested at specific stages of the cell cycle, nocodazole treatment is used. Cells are synchronized in metaphase by treatment with 0.05 μg/ml nocodazole for 16 h. Rounded cells are collected by gentle pipetting and released from drug-induced cell cycle block by washing three times with phosphate-buffered saline (PBS) and re-plated in drug-free medium. Cells are collected at different time points up to 12 h.

Cells are synchronized in early S-phase by double thymidine treatment (2 mM) for 12 h, and released in drug-free medium for 8 and 12 h. Cell cycle position can be monitored by flow cytometry. The following procedure is used: Thymidine (Sigma Chemical Co.) is prepared as a 100 mM stock solution in phosphate buffered saline, pH 7.4. Briefly, (1) exponentially growing cells are diluted to $2.5 \times 10^5$/ml with fresh medium supplemented with 2 mM thymidine for 12 hours. During this period, the G2/M cells progress into G1 and then, with the original G1 population, acquire a biochemical state equivalent to a G1/S phase border cell. (G2M=3.6 hours+G1=8.4 hours, TOTAL=12 hours). Any cells in S phase upon addition of thyrnidine are blocked in S phase. (2) Release of the cells from the first thymidine block is performed by centrifuging suspension cells (600×g for 5 minutes), discarding the thymidine-medium and washing twice in an equal volume of complete medium. For monolayer cultures, the thymidine is removed by pouring-off the thymidine-medium, and adding fresh medium, repeat twice for a total of three washes. (3) Cells are then incubated in fresh medium for 16 hours. During this period the cells recover from the thymidine-block (approximately 1-2 hours) and progress through the cell cycle, divide and enter G1 of the next cell cycle. Entry into G1 of the next cell will commence with the cells that were blocked at the end of S phase (the leading-edge cells). This takes about 5-6 hours following release from thymidine block (1-2 hours recovery+4 hours progression through G2/M). Entry into G1 of the next cell cycle will end with the lagging-edge cells (those arrested at G1/S) progressing through the cell cycle and dividing (between 16 and 18 hours). (4) At the end of the 16 hour release period, cells are diluted to $2.5 \times 10^5$/ml and re-incubated with 2 mM thymidine-containing medium for 12-14 hours. Cells in G2/M or G1 would progress and arrest at the G1/S phase border. Flow cytometric determination of cell cycle position at 8-10 hours following the re-addition of thymidine will ensure that the population of cells is sufficiently synchronized before the more complex cell cycle study is commenced. (5) Release of cells from the second thymidine block follows essentially the washing procedures laid out in Step 2.

Cycloheximide Treatment. To inhibit protein synthesis, cells are cultured in the presence of 10 μg/ml cycloheximide for the indicated time points. Inhibition of protein synthesis in metaphase-arrested cells is achieved as follows: cells are treated with 0.05 μg/ml nocodazole for 16 h, and rounded cells are collected by gentle pipetting and cultured further with 0.05 μg/ml nocodazole and 10 μg/ml cycloheximide for up to 120 min. Inhibition of protein synthesis in cells exiting mitosis as achieved as follows: nocodazole-arrested cells are released in drug-free medium for 1 h and cultured further with 10 μg/ml cycloheximide for up to 60 min.

$CaPO_4$ Transfection. The following protocol describes transfection in a 24-well plate. On Day 1, cells are seeded at $5 \times 10^5$ cells/well, and left in medium containing fetal calf serum (FCS). On Day 2, cells are re-feed cells with 1 ml fresh medium containing FCS. A DNA precipitate is prepared by mixing 47.5 µl 1×TBS (TBS: 8 g NaCl, 0.2 g KCl, 3 g Tris base, in 1 L, pH 7.4)] with 20 µl DNA (500 µg/ml). and 7.5 µl 2.5 M $CaCl_2$. The above mix is added to 75 µl 2×HBS (8 g NaCl, 6 g Hepes, 0.2 g $Na_2HPO_4$ (anhydrous) per 500 ml, pH 7.1, sterile-filtered). The precipitate is then added directly to the medium on cells, and the cells incubated for 3 hours at 37° C. The medium is removed, and 1 ml 15% glycerol in PBS (8 g NaCl, 0.2 g KCl, 1.44 g $Na_2HPO_4$, 0.24 g $KH_2PO_4$ in 1 L, pH 7.4, autoclaved) is added to each well. After 1 minute, the glycerol is removed, taking great care not to dislodge cells (some cell types become less well attached after glycerol shock), and the cells washed with PBS or serum free medium. One ml growth medium is added, and left at 37° C. for 6-72 hours.

Plasmids.

Mammalian expression constructs of USP47 (FLAG or FLAG-HA) were constructed using PCR from an EST containing USP47. cDNAs were cloned using EcoRV and XhoI. Mutations present in the cDNA were reverted by QuikChange Site-directed mutatgenesis using the kit from Strategene, La Jolla, Calif. Mutants in the catalytic cysteine were also generated by QuikChange. USP47 truncation mutants were generated by PCR. His-tagged baculovirus constructs were constructed by cloning USP47 cDNAs into pFastBac before homologous recombination in bacteria to generate the complete baculovirus (Invitrogen). All constructs are verified by DNA sequencing.

Cell Lysis. This procedure is used to lyse cells prior to immunoblotting and immunoprecipitation. Each plate is rinsed once with cold PBS (5 ml for a 100 mm plate), and aspirated off. The plates are placed on ice and 1 ml of lysis buffer (see below) added. When lysis becomes apparent, keeping the lid on, the plate is held partially open with one hand while tilting the plate to one side. Using a pipette, aspirate and re-release buffer until the particulate cellular matter has accumulated in the pool. Collect each of the lysates into centrifuge tubes, and spin at maximum speed for 5-10 minutes at 4° C. to pellet cell debris. Add 50 to 100 µl of Protein A beads (in a 50% slurry, pre-washed with PBS) to new centrifuge tubes, transfer the cell lysate supernatants to the new tubes, and place at 4° C. for 20 to 30 minutes (pre-clearing step). Preimmune sera or normal sera may be used to further pre-clear the cell lysate as necessary. After the pre-clearing step, centrifuge the lysate in a microcentrifuge for 5 minutes at low speed (4000-5000 rpm) to pellet the beads. The supernatant is now ready for immunoprecipitation. Lysis buffer: Nonidet P-40 lysis buffer (NP-40 LB). NP-40: 50 mM Tris-HCl (pH 7.5), 150 mM NaCl, 0.5% NP-40, and 50 mM NaF). Immediately before use, add the following 100× stocks to the lysis buffer: 100 mM $NaVO_3$ in $ddH_2O$, 100 mM DTT in $ddH_2O$, 100 mM PMSF in 100% isopropyl alcohol, and 100× Protease inhibitor (2.5 mg/ml Leupeptin, 2.5 mg/ml Aprotinin, 100 mM (=15 mg/ml) Benzamidine, and 1 mg/ml Trypsin inhibitor in ddH2O.

Antibodies. The following antibodies are used for immunoblotting and/or immunoprecipitation: anti-Cdc25A (F6, Santa Cruz Biotechnology, Santa Cruz, Calif.); anti-Flag (M2, Sigma); anti-Cul1, (Zymed, San Francisco, Calif.); anti-Skp1 (1C10F4, Zymed), anti-β-TrCP1 (polyclonal serum), anti-β-TrCP1 (Zymed); anti-USP47 (monoclonal, Abnova), anti-USP47 (Bethyl Laboratories), anti-HA (Bethyl Laboratories), and anti-ECS (Bethyl Laboratories).

Immunoprecipitation. Add the desired antibody or antibodies (with or without competing peptides) as appropriate to fresh 1.5 ml Eppendorf tubes. Add pre-cleared cell lysate supernatant to the appropriate tubes, not carrying over any beads, and incubate at cold temperature for 2 hours to overnight. Add pre-washed Protein A beads to each of the tubes, and place in cold for 1 hour. Spin the tubes for 2 minutes at 2000 rpm to pellet the beads. Aspirate off the supernatants. Wash the pellets with a large volume (1 ml) of lysis buffer per tube (i.e., lysis buffer without protease inhibitors). Spin the tubes for 2 minutes at 2000 rpm, and then aspirate off the supernatant as before. Repeat for a total of three washes. After the final aspiration, add 10 µl of 2×SDS sample buffer to the lid of each tube, and briefly spin the tubes to draw the sample buffer down to the pellet. Boil the samples on a 100° C. heater for 4 minutes. Load all of the supernatant onto a SDS gel and run the gel. If conducting an immuno-blotting, proceed to description below. For autoradiography, dry and develop the gel via phospho-imaging (2 hours to an overnight exposure) and/or standard autoradiography (2 to 5 day exposure while stored at −80 degrees with enhancer screens).

Western Blotting (IP-Western). Immuno-blotting is conducted essentially as described in Donzelli et al. (2002), supra. Wet three pieces of the Whatman paper in Western transfer buffer (48 mM Tris Base, 39 mM Glycine, 0.0375% SDS, and 20% Methanol in $ddH_2O$), remove excess of buffer and place them onto the platinum anode (BIO-RAD semi-dry trans-blot SD). Wet the nitrocellulose in the same buffer and place it onto the Whatman paper. Wet the gel in the transfer buffer for 5 to 10 seconds and place it onto the nitrocellulose. Wet three pieces of Whatman paper and, removing excess of buffer, place them onto the gel. Air bubbles should be removed throughout this procedure. Place the trans-blot cathode onto the stack. Transfer the gel at a constant voltage between 15 to 25V for 30 minutes.

Place the nitrocellulose in staining solution (100 ml $dH_2O$ and 1 ml Ponceau S solution (2 g Ponceau S, 30 ml trichloroacetic acid, 100 ml $dH_2O$) to stain for 2 to 5 minutes. Pour out the Ponceau S staining solution, and rinse twice with $dH_2O$. Pour out the $dH_2O$ and add some PBS to de-stain the nitrocellulose, with slow shaking until the protein bands disappear (about 5 to 10 minutes). Pour off the PBS, and add blocking solution (100 ml 1×PBS, 0.1 ml Tween-20, 5 g non-fat dry milk) to the nitrocellulose (30 to 50 ml per filter). Place the dish on a shaker (slow) for at least 1 hour to overnight. Pour out the blocking solution and rinse the blot once with PBS. Pour off the PBS, and add enough blocking solution to cover the nitrocellulose. Also add the primary antibody. The dilution of antibody used is entirely antibody dependent. The range of dilution runs from 1:5 (for some low titer monoclonal antibodies, it is possible to directly incubate the filter in the hybridoma supernatant without any dilution) to 1:5000. Place the dish on a shaker (slow) for at least 1 hour to overnight at room temperature. Transfer the blot to a new dish. Wash the blot five to six times each for 10 minutes with 0.1% Tween-20 in PBS and slow shaking. Add some blocking solution and secondary antibody (e.g. horseradish peroxidase-conjugated mouse anti-rabbit antibody in a 1:10,000 dilution if the primary antibody is of rabbit origin and the signal is to be detected by luminescence) to the nitrocellulose. Continue with slow shaking for 1 hour at room temperature. Wash the blot 5 times for 10 minutes each with 0.1% Tween-20 in PBS and slow shaking as before. Wash the blot once for 5 minutes with PBS and slow shaking.

The blot is now ready for developing with the detection reagents. Using ECL detection reagents (RPN 2106, Amersham), mix equal volumes of each of the reagents in a fresh dish. Place the blot in the mixture for exactly 1 minute, with frequent agitation, making sure all blot surfaces receive sufficient contact with the reagents. Place saran-wrapped blot in an X-ray cassette, and using a timer, expose the blot to X-ray film for between 30 seconds to 5 minutes. Develop the films, and if available time remains, adjust the exposure times as necessary.

Phosphatase treatment. 500 units of λ protein phosphatase (New England Biolabs, Beverly, Mass.) were added to USP47 or USP47/β-TrCP1/2 immunocomplexes in the presence of $MgCl_2$ for 30 min at 30° C.

Peptide binding assay. The peptides are coupled to agarose beads using the Aminolink Kit (Pierce, Rockford, Ill.). Coupled USP47 peptides (10 mg) are incubated with $^{35}$S-methionine-labeled in vitro-translated β-TrCP1 and β-TrCP2 proteins are obtained using the TNT-coupled reticulocyte lysate system (Promega, Madison, Wis.) in the presence of 5 μCi of $^{35}$S-labeled methionine (Amersham Biosciences, Piscataway, N.Y.). Agarose beads are washed with RIPA buffer and binding is assayed by SDS-PAGE followed by autoradiography.

In Vitro Ubiquitination Assay

Ubiquitin ligation is determined essentially as described in Carrano et al. (Nat Cell Biol, 1999; 1:193-199), using $^{35}$S-methionine-labeled in vitro-translated USP47. Baculovirus β-TrCP1, Skp2 or Fbw7 are all co-expressed with $His_6$-Skp1, purified by nickel-agarose chromatography and added at roughly similar amounts to the reaction. Briefly, 2 μl of in vitro-translated $^{35}$S-labeled USP47 is incubated at 30° C. for various time periods in 10 μl of ubiquitinylation mix containing 40 mM Tris pH 7.6, 5 mM $MgCl_2$, 1 mM DTT, 10% glycerol, 1 μM ubiquitin aldehyde, 1 mg/ml methyl ubiquitin, 10 mM creatine phosphate, 0.1 mg/ml creatine kinase, 0.5 mM ATP, 1 μM okadaic acid, and 20 μg cell extract obtained from prometaphase MEFs using a "cell nitrogen-disruption bomb" (Parr, cat #4639). Where indicated, approximately 5 ng of purified recombinant SCF complexes are added. Reactions are stopped with Laemmli sample buffer and the products are run on protein gels under denaturing conditions. Polyubiquitinylated USP47 forms are identified by autoradiography. Roc1/Ha-Cul1/His-Skp1/β-Trcp1 and Roc1/Ha-Cul1/His-Skp1/Skp2 complexes are expressed in 5B insect cells and purified by Nickel-Agarose chromatography.

siRNA.

Cdh1 (Donzelli et al., (2002), supra); β-TrCP1/2 (Guardavaccaro et al., In vivo Dev Cell 4, 799-812 (2003); Margottin-Goguet et al., Dev Cell, 2003; 4:813-26); Emil (Hsu et al., Nat Cell Biol, 2002; 4:358-66); and Cdc25A (Zhao et al., Proc Natl Acad Sci USA, 2002; 24:24) 21 base pairs siRNA oligonucleotides were from Dharmacon Research Inc. (Lafayette, Colo.). Cells were transfected with siRNA duplexes by Metafectene (Biontex, Germany), following manufacturer's instructions.

Briefly, the siRNA oligos used for USP47 silencing were based on available human USP47 coding regions (Accession No. NM 017944 (SEQ ID NO:2), the partial cDNA sequence Accession No. BC017795 (SEQ ID NO:11), or (SEQ ID NO:13), Homo sapiens cDNA clone IMAGE:4815410, Accession No. BC071559). The USP47 siRNAs correspond to oligos 1 and 4 from the Dharmacon (Lafayette, Colo.) USP47 smartpool SEQ ID NO:16 and SEQ ID NO:17.

Example 1

Binding Characteristics of USP47

USP47 was characterized using an immunoprecipitation procedure followed by mass spectrometry analysis. This analysis identified USP47 as a protein that interacts with the F-box protein β-TrCP, FIG. 1A-C shows USP47 specifically binding to β-TrCP-1 and β-TrCP-2. USP47 binding to both β-TrCP-1 and β-TrCP-2 requires an intact WD-40 repeat region of β-TrCP. The WD repeat region of TRCP is the substrate binding domain. For these binding studies, 293T cells were transfected with the indicated FLAG-tagged Fbw family F-box protein constructs (in FIG. 1A-C), and lysates from transfected cells were immunoprecipitated using anti-FLAG constructs prior to Western blotting for USP47, CUL1, and the FLAG epitope, as shown in FIG. 1A-C.

Under normal conditions, β-TrCP binds USP47 through a region containing amino acids 1-1000 (of for example SEQ ID NO:1, 3, 4, 5, or 12), while in the presence of proteasome inhibitor, only the catalytic region of USP47 (1-500) of SEQ ID NO:1 is required. These results show that USP47 exhibits both β-TrCP specific and ubiquitin-specific binding.

Example 2

USP47 Binding to β-TrCP Controls β-TrCP Substrate Levels

FIG. 2A-D illustrates USP47 knockdown leads to increased β-TrCP substrate levels. HeLa cells were transfected with siRNAs for USP47 and β-TRCP; lysates from the transfected cells were analyzed by Western blotting. Skp1 is used as a loading control.

Example 3

USP47 Inhibition Induces Apoptosis

Figure 3:
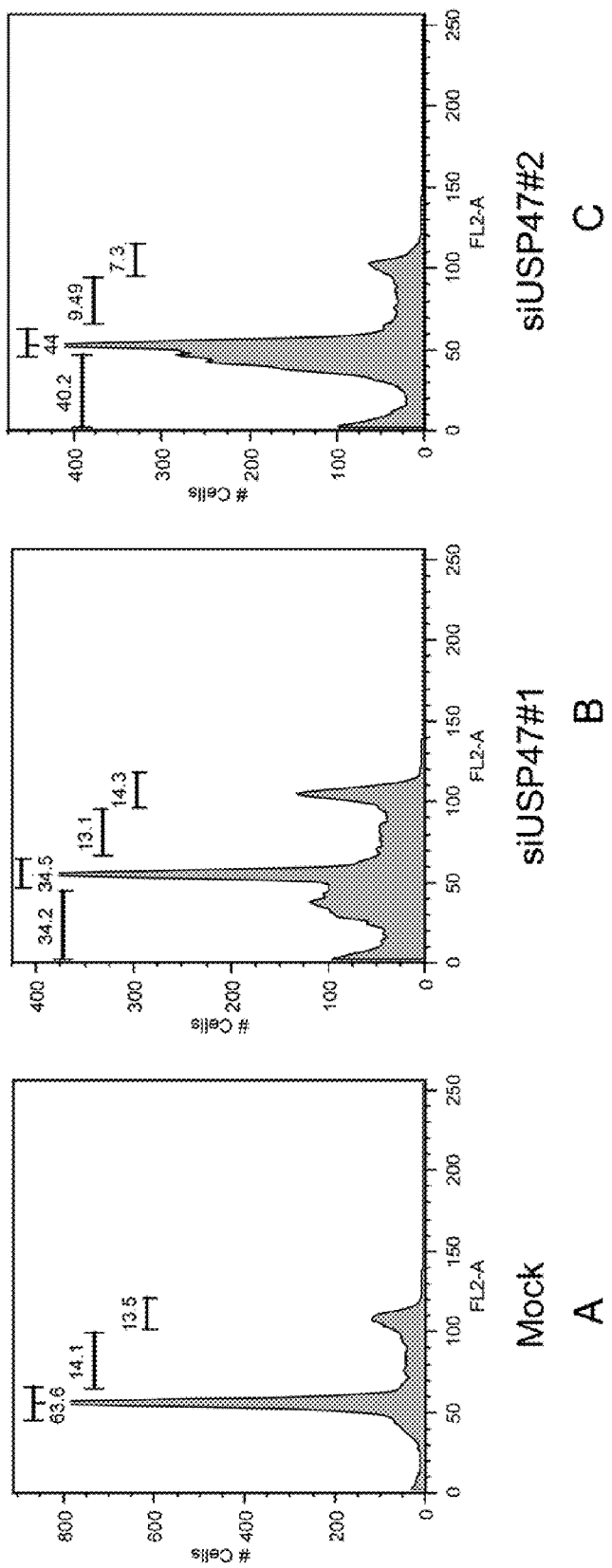
FIG. 3A-C shows FACS results of USP47 siRNA knockdowns inducing apoptosis.

FIG. 3A-C shows FACS results of USP47 siRNA knockdowns inducing apoptosis. HeLa cells were transfected with siRNA for USP47 with SEQ ID NO:16 and cells were also transfected with siRNA for USP47 with SEQ ID NO:17. Mock-transfected HeLa cells were used as a control. The transfected cells were analyzed by propidium iodide staining and FACS.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

While the compositions and methods of this invention have been described in terms of specific embodiments, it will be apparent to those of skill in the art that variations may be applied to the compositions and methods and in the steps or in the sequence of steps of the method described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention as defined by the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method of inducing apoptosis or cell death in a target cell comprising contacting the target cell with an effective amount of an inhibitor of ubiquitin specific protease 47 (USP47), wherein the inhibitor of USP47 is a siRNA comprising SEQ ID NO:16 or SEQ ID NO:17.

2. The method of claim 1, wherein the target cell is a diseased or abnormal cell from tissue or a cell that exhibits a disease or abnormal condition selected from the group consisting of cancer, infection, immune disorder, cardiovascular disease, and inflammatory disorders.

3. The method of claim 1, further comprising contacting the target cell with a second agent for sensitizing the cell to DNA damage or apoptosis.

4. A method of killing a target cell comprising contacting the target cell with an effective amount of an inhibitor of ubiquitin specific protease 47 (USP47), wherein the inhibitor of USP47 is a siRNA comprising SEQ ID NO:16 or SEQ ID NO:17.

5. The method of claim 4, further comprising contacting the target cell with a second agent for sensitizing the cell to DNA damage.

6. The method of claim 4, wherein the target cell is a diseased or abnormal cell from tissue or a cell that exhibits a disease or abnormal condition selected from the group consisting of cancer, infection, immune disorder, cardiovascular disease, and inflammatory disorders.

7. A method of treating cancer in a subject suffering from cancer comprising administering to the subject an effective amount of a ubiquitin specific protease 47 (USP47) inhibitor, wherein the USP47 inhibitor is a siRNA comprising SEQ ID NO:16 or SEQ ID NO:17.

8. The method of claim 7, wherein the USP47 inhibitor induces apoptosis.

9. The method of claim 7, wherein the USP47 inhibitor results in loss of beta-transducin repeat containing protein (beta-TrCP) activity.

10. A method of inducing apoptosis or cell death in a target cell of a mammal which comprises contacting said target cell with an effective amount of an inhibitor of ubiquitin specific protease 47 (USP47), wherein the inhibitor of USP47 is a siRNA comprising SEQ ID NO:16 or SEQ ID NO:17.

11. The method of claim 10, wherein the mammal is a human.

12. An inhibitor of ubiquitin specific protease 47 (USP47) comprising SEQ ID NO:16 or SEQ ID NO:17.

* * * * *

UNITED STATES PATENT AND TRADEMARK OFFICE
CERTIFICATE OF CORRECTION

PATENT NO. : 8,076,309 B2  
APPLICATION NO. : 12/431336  
DATED : December 13, 2011  
INVENTOR(S) : Michele Pagano et al.

Page 1 of 1

It is certified that error appears in the above-identified patent and that said Letters Patent is hereby corrected as shown below:

In the Specification

At Column 1, beginning in Line 11 and ending in Line 14 please replace:
"This invention was made in part in the course of research sponsored by the National Institutes of Health (NIH) Grant R37-CA76584. The U.S. government may have certain rights in this invention."

With:
--This invention was made with government support under grant CA076584 awarded by the National Institutes of Health. The government has certain rights in the invention.--

Signed and Sealed this
Thirteenth Day of August, 2019

Andrei Iancu
*Director of the United States Patent and Trademark Office*

SEQUENCE LISTING

<160> NUMBER OF SEQ ID NOS: 17

<210> SEQ ID NO 1
<211> LENGTH: 1287
<212> TYPE: PRT
<213> ORGANISM: Homo sapiens

<400> SEQUENCE: 1

```
Met Val Pro Gly Glu Glu Asn Gln Leu Val Pro Lys Glu Ala Pro Leu
1               5                   10                  15

Asp His Thr Ser Asp Lys Ser Leu Leu Asp Ala Asn Phe Glu Pro Gly
                20                  25                  30

Lys Lys Asn Phe Leu His Leu Thr Asp Lys Asp Gly Glu Gln Pro Gln
            35                  40                  45

Ile Leu Leu Glu Asp Ser Ser Ala Gly Glu Asp Ser Val His Asp Arg
50                  55                  60

Phe Ile Gly Pro Leu Pro Arg Glu Gly Ser Gly Ser Thr Ser Asp
65                  70                  75                  80

Tyr Val Ser Gln Ser Tyr Ser Tyr Ser Ile Leu Asn Lys Ser Glu
                85                  90                  95

Thr Gly Tyr Val Gly Leu Val Asn Gln Ala Met Thr Cys Tyr Leu Asn
                100                 105                 110

Ser Leu Leu Gln Thr Leu Phe Met Thr Pro Glu Phe Arg Asn Ala Leu
            115                 120                 125

Tyr Lys Trp Glu Phe Glu Glu Ser Glu Glu Asp Pro Val Thr Ser Ile
130                 135                 140

Pro Tyr Gln Leu Gln Arg Leu Phe Val Leu Leu Gln Thr Ser Lys Lys
145                 150                 155                 160

Arg Ala Ile Glu Thr Thr Asp Val Thr Arg Ser Phe Gly Trp Asp Ser
                165                 170                 175

Ser Glu Ala Trp Gln Gln His Asp Val Gln Glu Leu Cys Arg Val Met
            180                 185                 190

Phe Asp Ala Leu Glu Gln Lys Trp Lys Gln Thr Glu Gln Ala Asp Leu
        195                 200                 205

Ile Asn Glu Leu Tyr Gln Gly Lys Leu Lys Asp Tyr Val Arg Cys Leu
210                 215                 220

Glu Cys Gly Tyr Glu Gly Trp Arg Ile Asp Thr Tyr Leu Asp Ile Pro
225                 230                 235                 240

Leu Val Ile Arg Pro Tyr Gly Ser Ser Gln Ala Phe Ala Ser Val Glu
                245                 250                 255

Glu Ala Leu His Ala Phe Ile Gln Pro Glu Ile Leu Asp Gly Pro Asn
            260                 265                 270

Gln Tyr Phe Cys Glu Arg Cys Lys Lys Lys Cys Asp Ala Arg Lys Gly
        275                 280                 285

Leu Arg Phe Leu His Phe Pro Tyr Leu Leu Thr Leu Gln Leu Lys Arg
290                 295                 300

Phe Asp Phe Asp Tyr Thr Thr Met His Arg Ile Lys Leu Asn Asp Arg
305                 310                 315                 320

Met Thr Phe Pro Glu Glu Leu Asp Met Ser Thr Phe Ile Asp Val Glu
                325                 330                 335

Asp Glu Lys Ser Pro Gln Thr Glu Ser Cys Thr Asp Ser Gly Ala Glu
            340                 345                 350

Asn Glu Gly Ser Cys His Ser Asp Gln Met Ser Asn Asp Phe Ser Asn
        355                 360                 365
```

```
Asp Asp Gly Val Asp Glu Gly Ile Cys Leu Glu Thr Asn Ser Gly Thr
    370                 375                 380

Glu Lys Ile Ser Lys Ser Gly Leu Glu Lys Asn Ser Leu Ile Tyr Glu
385                 390                 395                 400

Leu Phe Ser Val Met Val His Ser Gly Ser Ala Ala Gly Gly His Tyr
                405                 410                 415

Tyr Ala Cys Ile Lys Ser Phe Ser Asp Glu Gln Trp Tyr Ser Phe Asn
                420                 425                 430

Asp Gln His Val Ser Arg Ile Thr Gln Glu Asp Ile Lys Lys Thr His
            435                 440                 445

Gly Gly Ser Ser Gly Ser Arg Gly Tyr Tyr Ser Ser Ala Phe Ala Ser
        450                 455                 460

Ser Thr Asn Ala Tyr Met Leu Ile Tyr Arg Leu Lys Asp Pro Ala Arg
465                 470                 475                 480

Asn Ala Lys Phe Leu Glu Val Asp Glu Tyr Pro Glu His Ile Lys Asn
                485                 490                 495

Leu Val Gln Lys Glu Arg Glu Leu Glu Glu Gln Lys Arg Gln Arg
            500                 505                 510

Glu Ile Glu Arg Asn Thr Cys Lys Ile Lys Leu Phe Cys Leu His Pro
            515                 520                 525

Thr Lys Gln Val Met Met Glu Asn Lys Leu Glu Val His Lys Asp Lys
530                 535                 540

Thr Leu Lys Glu Ala Val Glu Met Ala Tyr Lys Met Met Asp Leu Glu
545                 550                 555                 560

Glu Val Ile Pro Leu Asp Cys Cys Arg Leu Val Lys Tyr Asp Glu Phe
                565                 570                 575

His Asp Tyr Leu Glu Arg Ser Tyr Glu Gly Glu Asp Thr Pro Met
            580                 585                 590

Gly Leu Leu Leu Gly Gly Val Lys Ser Thr Tyr Met Phe Asp Leu Leu
            595                 600                 605

Leu Glu Thr Arg Lys Pro Asp Gln Val Phe Gln Ser Tyr Lys Pro Gly
            610                 615                 620

Glu Val Met Val Lys Val His Val Asp Leu Lys Ala Glu Ser Val
625                 630                 635                 640

Ala Ala Pro Ile Thr Val Arg Ala Tyr Leu Asn Gln Thr Val Thr Glu
                645                 650                 655

Phe Lys Gln Leu Ile Ser Lys Ala Ile His Leu Pro Ala Glu Thr Met
            660                 665                 670

Arg Ile Val Leu Glu Arg Cys Tyr Asn Asp Leu Arg Leu Leu Ser Val
        675                 680                 685

Ser Ser Lys Thr Leu Lys Ala Glu Gly Phe Phe Arg Ser Asn Lys Val
        690                 695                 700

Phe Val Glu Ser Ser Glu Thr Leu Asp Tyr Gln Met Ala Phe Ala Asp
705                 710                 715                 720

Ser His Leu Trp Lys Leu Leu Asp Arg His Ala Asn Thr Ile Arg Leu
            725                 730                 735

Phe Val Leu Leu Pro Glu Gln Ser Pro Val Ser Tyr Ser Lys Arg Thr
                740                 745                 750

Ala Tyr Gln Lys Ala Gly Gly Asp Ser Gly Asn Val Asp Asp Cys
            755                 760                 765

Glu Arg Val Lys Gly Pro Val Gly Ser Leu Lys Ser Val Glu Ala Ile
770                 775                 780

Leu Glu Glu Ser Thr Glu Lys Leu Lys Ser Leu Ser Leu Gln Gln Gln
```

```
              785                 790                 795                 800
        Gln Asp Gly Asp Asn Gly Asp Ser Ser Lys Ser Thr Glu Thr Ser Asp
                        805                 810                 815
        Phe Glu Asn Ile Glu Ser Pro Leu Asn Glu Arg Asp Ser Ser Ala Ser
                        820                 825                 830
        Val Asp Asn Arg Glu Leu Glu Gln His Ile Gln Thr Ser Asp Pro Glu
                        835                 840                 845
        Asn Phe Gln Ser Glu Glu Arg Ser Asp Ser Asp Val Asn Asn Asp Arg
                        850                 855                 860
        Ser Thr Ser Ser Val Asp Ser Asp Ile Leu Ser Ser Ser His Ser Ser
        865                 870                 875                 880
        Asp Thr Leu Cys Asn Ala Asp Asn Ala Gln Ile Pro Leu Ala Asn Gly
                        885                 890                 895
        Leu Asp Ser His Ser Ile Thr Ser Ser Arg Arg Thr Lys Ala Asn Glu
                        900                 905                 910
        Gly Lys Lys Glu Thr Trp Asp Thr Ala Glu Glu Asp Ser Gly Thr Asp
                        915                 920                 925
        Ser Glu Tyr Asp Glu Ser Gly Lys Ser Arg Gly Glu Met Gln Tyr Met
                        930                 935                 940
        Tyr Phe Lys Ala Glu Pro Tyr Ala Ala Asp Glu Gly Ser Gly Glu Gly
        945                 950                 955                 960
        His Lys Trp Leu Met Val His Val Asp Lys Arg Ile Thr Leu Ala Ala
                        965                 970                 975
        Phe Lys Gln His Leu Glu Pro Phe Val Gly Val Leu Ser Ser His Phe
                        980                 985                 990
        Lys Val Phe Arg Val Tyr Ala Ser  Asn Gln Glu Phe Glu  Ser Val Arg
                        995                1000                1005
        Leu Asn  Glu Thr Leu Ser Ser  Phe Ser Asp Asp Asn  Lys Ile Thr
        1010                1015                1020
        Ile Arg  Leu Gly Arg Ala Leu  Lys Lys Gly Glu Tyr  Arg Val Lys
        1025                1030                1035
        Val Tyr  Gln Leu Leu Val Asn  Glu Gln Glu Pro Cys  Lys Phe Leu
        1040                1045                1050
        Leu Asp  Ala Val Phe Ala Lys  Gly Met Thr Val Arg  Gln Ser Lys
        1055                1060                1065
        Glu Glu  Leu Ile Pro Gln Leu  Arg Glu Gln Cys Gly  Leu Glu Leu
        1070                1075                1080
        Ser Ile  Asp Arg Phe Arg Leu  Arg Lys Leu Thr Trp  Lys Asn Pro
        1085                1090                1095
        Gly Thr  Val Phe Leu Asp Tyr  His Ile Tyr Glu Glu  Asp Ile Asn
        1100                1105                1110
        Ile Ser  Ser Asn Trp Glu Val  Phe Leu Glu Val Leu  Asp Gly Val
        1115                1120                1125
        Glu Lys  Met Lys Ser Met Ser  Gln Leu Ala Val Leu  Ser Arg Arg
        1130                1135                1140
        Trp Lys  Pro Ser Glu Met Lys  Leu Asp Pro Phe Gln  Glu Val Val
        1145                1150                1155
        Leu Glu  Ser Ser Ser Val Asp  Glu Leu Arg Glu Lys  Leu Ser Glu
        1160                1165                1170
        Ile Ser  Gly Ile Pro Leu Asp  Asp Ile Glu Phe Ala  Lys Gly Arg
        1175                1180                1185
        Gly Thr  Phe Pro Cys Asp Ile  Ser Val Leu Asp Ile  His Gln Asp
        1190                1195                1200
```

| Leu | Asp | Trp | Asn | Pro | Lys | Val | Ser | Thr | Leu | Asn | Val | Trp | Pro | Leu |
|---|---|---|---|---|---|---|---|---|---|---|---|---|---|---|
| 1205 | | | | 1210 | | | | | 1215 | | | | | |

| Tyr | Ile | Cys | Asp | Asp | Gly | Ala | Val | Ile | Phe | Tyr | Arg | Asp | Lys | Thr |
|---|---|---|---|---|---|---|---|---|---|---|---|---|---|---|
| 1220 | | | | | 1225 | | | | | 1230 | | | | |

| Glu | Glu | Leu | Met | Glu | Leu | Thr | Asp | Glu | Gln | Arg | Asn | Glu | Leu | Met |
|---|---|---|---|---|---|---|---|---|---|---|---|---|---|---|
| 1235 | | | | | 1240 | | | | | 1245 | | | | |

| Lys | Lys | Glu | Ser | Ser | Arg | Leu | Gln | Lys | Thr | Gly | His | Arg | Val | Thr |
|---|---|---|---|---|---|---|---|---|---|---|---|---|---|---|
| 1250 | | | | | 1255 | | | | | 1260 | | | | |

| Tyr | Ser | Pro | Arg | Lys | Glu | Lys | Ala | Leu | Lys | Ile | Tyr | Leu | Asp | Gly |
|---|---|---|---|---|---|---|---|---|---|---|---|---|---|---|
| 1265 | | | | | 1270 | | | | | 1275 | | | | |

| Ala | Pro | Asn | Lys | Asp | Leu | Thr | Gln | Asp |
|---|---|---|---|---|---|---|---|---|
| 1280 | | | | | 1285 | | | |

<210> SEQ ID NO 2
<211> LENGTH: 7777
<212> TYPE: DNA
<213> ORGANISM: Homo sapiens

<400> SEQUENCE: 2

| | |
|---|---|
| agaggggaaa agaacgtcag gagagtgaac gggagcaaat aaaacgctgt ccattctgac | 60 |
| tggaagggcc agagccgtgt ctaagggcgg gggccgggag gtggcccgcg gtggtgtctc | 120 |
| taccaggacg aggcctgggg tatctgaaga ggggatgacg tccaggcgct ttgctaaagg | 180 |
| gaagccagaa gggtatgagt tgctagggtc agagatgggg ctttcggctc gagtcttttcc | 240 |
| ctgcagggca gagagtccga agagcccgag aaggcaggga ggacagtggg cctggtcctt | 300 |
| ccccggccgg cagagggagt cccgagatgg aacgtccagc tctcctctaa cgaaaagcgt | 360 |
| ttgcatggct gtctcgccaa ttctgtacct cccggggctg aggaagagcc gaggtgacta | 420 |
| gaagctagcg acaagtgccg gccacctccg acgccaggcc ccgggcttgg agcccgacgg | 480 |
| gccgaattct cgcgagagcg gccgccgcca ttttccatt gattgcagcg ggctggggga | 540 |
| ggggccgacg acgaaggcgg ctgtggtagc ggcggcggcg gcggcggagc cctgggtcgg | 600 |
| tgtctgcgcg ctggtgtctg aggcccaggc tgaggcctcc gctattgctg gagcgcaggc | 660 |
| ggcggagagg atgactgccg ctgccattct ctcttgagct agcgagccgc cgccaccctc | 720 |
| cacccctcccc cggcagggcg gagaggagcg gccggagtca gcgatggtgc ccggcgagga | 780 |
| gaaccaactg gtcccgaaag aggcaccact ggatcatacc agtgacaagt cacttctcga | 840 |
| cgctaatttt gagccaggaa agaagaactt tctgcatttg acagataaag atggtgaaca | 900 |
| acctcaaata ctgctggagg attccagtgc tggggaagac agtgttcatg acaggtttat | 960 |
| aggtccgctt ccaagagaag gttctggggg ttctaccagt gattatgtca gccaaagcta | 1020 |
| ctcctactca tctattttga ataaatcaga aactggatat gtgggactag taaccaagc | 1080 |
| aatgacttgc tatttgaata gccttttgca acactttttt atgactcctg aatttaggaa | 1140 |
| tgcattatat aagtgggaat ttgaagaatc tgaagaagat ccagtgacaa gtattccata | 1200 |
| ccaacttcaa aggcttttttg ttttgttaca aaccagcaaa aagagagcaa ttgaaaccac | 1260 |
| agatgttaca aggagctttg gatgggatag tagtgaggct tggcagcagc atgatgtaca | 1320 |
| agaactatgc agagtcatgt ttgatgcttt ggaacagaaa tggaagcaaa cagaacaggc | 1380 |
| tgatcttata aatgagctat atcaaggcaa gctgaaggac tacgtgagat gtctggaatg | 1440 |
| tggttatgag ggctggcgaa tcgacacata tcttgatatt ccattggtca tccgacctta | 1500 |
| tgggtccagc caagcatttg ctagtgtgga agaagcattg catgcattta ttcagccaga | 1560 |
| gattctggat ggcccaaatc agtattttttg tgaacgttgt aagaagaagt gtgatgcacg | 1620 |

```
gaagggcctt cggtttttgc attttcctta tctgctgacc ttacagctga aaagattcga    1680
ttttgattat acaaccatgc ataggattaa actgaatgat cgaatgacat tcccgagga     1740
actagatatg agtactttta ttgatgttga agatgagaaa tctcctcaga ctgaaagttg    1800
cactgacagt ggagcagaaa atgaaggtag ttgtcacagt gatcagatga gcaacgattt   1860
ctccaatgat gatggtgttg atgaaggaat ctgtcttgaa accaatagtg gaactgaaaa   1920
gatctcaaaa tctggacttg aaaagaattc cttgatctat gaacttttct ctgttatggt   1980
tcattctggg agcgctgctg gtggtcatta ttatgcatgt ataaagtcat tcagtgatga   2040
gcagtggtac agcttcaatg atcaacatgt cagcaggata acacaagagg acattaagaa   2100
aacacatggt ggatcttcag gaagcagagg atattattct agtgctttcg caagttccac   2160
aaatgcatat atgctgatct atagactgaa ggatccagcc agaaatgcaa aatttctaga   2220
agtggatgaa tacccagaac atattaaaaa cttggtgcag aaagagagag agttggaaga   2280
acaagaaaag agacaacgag aaattgagcg caatacatgc aagataaaat tattctgttt   2340
gcatcctaca aaacaagtaa tgatggaaaa taaattggag gttcataagg ataagacatt   2400
aaaggaagca gtagaaatgg cttataagat gatggattta aagaggtaa tacccctgga    2460
ttgctgtcgc cttgttaaat atgatgagtt tcatgattat ctagaacggt catatgaagg   2520
agaagaagat acaccaatgg ggcttctact aggtggcgtc aagtcaacat atatgtttga   2580
tctgctgttg gagacgagaa agcctgatca ggttttccaa tcttataaac ctggagaagt   2640
gatggtgaaa gttcatgttg ttgatctaaa ggcagaatct gtagctgctc ctataactgt   2700
tcgtgcttac ttaaatcaga cagttacaga attcaaacaa ctgatttcaa aggccatcca   2760
tttacctgct gaaacaatga gaatagtgct ggaacgctgc tacaatgatt tgcgtcttct   2820
cagtgtctcc agtaaaaccc tgaaagctga aggatttttt agaagtaaca aggtgtttgt   2880
tgaaagctcc gagactttgg attaccagat ggcctttgca gactctcatt tatggaaact   2940
cctggatcgg catgcaaata caatcagatt atttgttttg ctacctgaac aatccccagt   3000
atcttattcc aaaaggacag cataccagaa agctggaggc gattctggta atgtggatga   3060
tgactgtgaa agagtcaaag gacctgtagg aagcctaaag tctgtggaag ctattctaga   3120
agaaagcact gaaaaactca aaagcttgtc actgcagcaa cagcaggatg gagataatgg   3180
ggacagcagc aaaagtactg agacaagtga ctttgaaaac atcgaatcac ctctcaatga   3240
gagggactct tcagcatcag tggataatag agaacttgaa cagcatattc agacttctga   3300
tccagaaaat tttcagtctg aagaacgatc agactcagat gtgaataatg acaggagtac   3360
aagttcagtg gacagtgata ttcttagctc cagtcatagc agtgatactt tgtgcaatgc   3420
agacaatgct cagatccctt tggctaatgg acttgactct cacagtatca agtagtag    3480
aagaacgaaa gcaaatgaag ggaaaaaga aacatgggat acagcagaag aagactctgg   3540
aactgatagt gaatatgatg agagtggcaa gagtagggga gaaatgcagt acatgtattt   3600
caaagctgaa ccttatgctg cagatgaagg ttctggggaa ggacataaat ggttgatggt   3660
gcatgttgat aaaagaatta ctctggcagc tttcaaacaa catttagagc cctttgttgg   3720
agttttgtcc tctcacttca aggtctttcg agtgtatgcc agcaatcaag agtttgagag   3780
cgtccggctg aatgagacac tttcatcatt ttctgatgac aataagatta caattagact   3840
ggggagagca cttaaaaaag gagaatacag agttaaagta taccagcttt tggtcaatga   3900
acaagagcca tgcaagtttc tgctagatgc tgtgtttgct aaaggaatga ctgtacggca   3960
atcaaaagag gaattaattc ctcagctcag ggagcaatgt ggtttagagc tcagtattga   4020
```

```
caggtttcgt ctaaggaaaa aaacatggaa gaatcctggc actgtctttt tggattatca    4080
tatttatgaa gaagatatta atatttccag caactgggag gttttccttg aagttcttga    4140
tggggtagag aagatgaagt ccatgtcaca gcttgcagtt ttgtcaagac ggtggaagcc    4200
ttcagagatg aagttggatc ccttccagga ggttgtattg gaaagcagta gtgtggacga    4260
attgcgagag aagcttagtg aaatcagtgg gattcctttg gatgatattg aatttgctaa    4320
gggtagagga acatttccct gtgatatttc tgtccttgat attcatcagg atttagactg    4380
gaatcctaaa gtttctaccc tgaatgtctg gcctctttat atctgtgatg atggtgcggt    4440
catattttat agggataaaa cagaagaatt aatggaattg acagatgagc aaagaaatga    4500
actgatgaaa aagaaagca gtcgactcca gaagactgga catcgtgtaa catactcacc    4560
tcgtaaagag aaagcactaa aaatatatct ggatggagca ccaaataaag atctgactca    4620
agactgactc tgatagtgta gcattttccc tgggggagtt ttggttttaa ttagatggtt    4680
cactaccact gggtagtgcc attttggccg acatggttg gggtaaccca gtgacaccag    4740
cactgattgg actgccctac accaatcaga agctcagtgc ccaatgggcc actgttttga    4800
ctcggaatca tgttgtgcac tatagtcaaa tgtactgtaa agtgaaaagg gatgtgcaaa    4860
aaaataaaaa aaacaacaa aaaaagctaa ccttctatta gaaaggggga caggggaatg    4920
agtaaacttc ttttattgcg gacaaatgtg cacatagccg ctagtaaaac tagcctcaaa    4980
caggatgctc atagcttaat aataaaagct gtgcaaaggc catgaatgaa tgaattttct    5040
gtttatttca ctgatgcaca cattacctca ttgacaattc agaagtaaat ccaacgtgtg    5100
ttgactcttg gaaagcagca aaaacaggag ctgaagaaaa gaaattcttg gaaccagccg    5160
taacccagta aggaattgtg aagttgtgtt tttatttgt ttcatttttt gcagagtatt    5220
aagaacatta ttctggaaca tcagaacgtt tcccttagac cgatcccagc aggtggcagc    5280
tcagattgct gcagtgttgt aattataact gattgtactt aagttatgga gtagagaat    5340 atgtttcatt catttattca gcatgtaaat aaaattgatc ctgttgagtt atcataattg    5400
cagttcaact atctgccatg attattcttt tcacgtatca ttcattctgt acatttgtgt    5460
acattgagaa gtatagcaat ctatgtaaat gtaatcctca gtgaggttcc tcagtgctag    5520
gtcccatagg attgtcgttg cccttgttaa tgaggtttct ctgttcagcg gcttcaattt    5580
ttttctcttt gtacatctag ttttgaagat ttacttcaag tttgaatctt ctagaatgct    5640
tgtaagtcca gttttaattt ttagagtcaa tttgtagtta catgtagttt aacttttggg    5700
aaacgtctta acattgttct gaataaactt gctaatgagg tcaggtcatg gtacagactg    5760
atgcagtcaa catgatttca ttgcagagtt tattagtatc agcaagtttt tgctttgcta    5820
aataaaagta ctcaatgaac acaattctac ataaattttg acataccatc taatttataa    5880
aaatcaataa aaaaggtttt ggtaaaactt tttcatgcca gatgctgttt acaacaatga    5940
acatgccaat aaaacatttg ttcattctgt tgtgttattt tagtcattaa acttctgtgg    6000
atgaagaatc tgggttaaga atagatttgt catctttaaa tatgacattt tgtaatgtgt    6060
attggatatc tcatttctat gataaaggta tatttacagt aaagttctca taagagaaat    6120
gaaaagctgt gttaatatct aactttgggg aaccctgtca gtatttcaga tccgattttt    6180 acccttttt tcttataaga aagataaaat tagaaaatac tgttagcaaa tgtggctctg    6240
ccatttgaat ataatcaccg agaattccat gtcttaaaag tctcctggaa tccacaatga    6300
aaaaaaaaat cttttctaag gtatttttct ggctaatttt tatttgaaga aagctatagc    6360
atttagcgaa atttgactga agtaatgttc tgagtttgca ttagtgggat tggtgatgtt    6420
```

```
ctcagaagaa aattggaaac acttgtgatg aattgtctt cagatcactt agattttctg   6480
atgtaagagg acagctgttt ggttctgata caggcctgct tacttgggat gtagggttag   6540
taaatggggt ttctgcttta aaggactgac ttgctatcac acaaagagg cagacttgta   6600
aacacaatgg gctttggagt ttggtctgat tgggttggt ttagtattcc tatgagcgta   6660
aatggtaaaa ttcttctgat acccactctt tagactgtgc cttctgctct gttctttgtt   6720
ttatgtttaa ctgctgtttc taattgcagg tgtattacag atacaaataa gagtaaagaa   6780
aatatattc attatagaaa agaaaaatt aaaagcttct tgcttttcag tgcctgatag   6840
agtgaaaaca caaagttgca ctttaataat ttcaataaaa gctaatctgt gtcagcctcc   6900
ctctgcttca gagagtcagg tgagcatcca taacctaaca ggcagagccc tagcgatgtg   6960
gatcaagttt cctgagcccg ggggcggtgg agcctcatga tctcttatct tttgaggctg   7020
aggcaggtca catgcaacaa attgtgaccc tgctccccac aagtcatgca aaggttttga   7080
agagctttta ccgtggggca gatgaacttg tgtcaaccat gcacaccctg tgagaaccaa   7140
gtacctgtgt ttctaaggcg ggcactcaag gtgaggggtg cattctggcc aaagaaacaa   7200
aagctgtggg ttcaggacca tgccgtgtgt agctgatctg tacgggacgt gtatgtaagg   7260
aagagcaatc atgatagata agaacagtgt gtgaagcagc cttcacacta gagtgtttgg   7320
tcatctctta taatgtaagg gaaggtactt taaaattctg ggaagatgcg atgaactcat   7380
gtcccagtca gaaaataatc caatgaaata agcattggtt gccaggccac agttaggaat   7440
tgtattgtga tacatctaga ggccaagaga gcaggagaga gctaccaact tacactgtgg   7500
tttaagctaa atgaccgcac agcatcatag cattgcagtg ttgttactaa atctggaagt   7560
gacctgtgaa tgtatggaat acaataaagt ctttattct ggttcatttg ctagtacttc   7620
cttttgatt ggatactgta gttcttcctc tggatttat tttgttcagc gtcaaggccc   7680
taattttgca aatgtagtct aaaccacatt acgtggacta gaggatactc tgaattagca   7740
agttttttgt ttgctgaata aaactattcc atcttaa                             7777
```

<210> SEQ ID NO 3
<211> LENGTH: 157
<212> TYPE: PRT
<213> ORGANISM: Homo sapiens

<400> SEQUENCE: 3

```
Met Lys Ser Met Ser Gln Leu Ala Val Leu Ser Arg Arg Trp Lys Pro
1               5                   10                  15

Ser Glu Met Lys Leu Asp Pro Phe Gln Glu Val Leu Glu Ser Ser
            20                  25                  30

Ser Val Asp Glu Leu Arg Glu Lys Leu Ser Glu Ile Ser Gly Ile Pro
        35                  40                  45

Leu Asp Asp Ile Glu Phe Ala Lys Gly Arg Gly Thr Phe Pro Cys Asp
    50                  55                  60

Ile Ser Val Leu Asp Ile His Gln Asp Leu Asp Trp Asn Pro Lys Val
65                  70                  75                  80

Ser Thr Leu Asn Val Trp Pro Leu Tyr Ile Cys Asp Asp Gly Ala Val
                85                  90                  95

Ile Phe Tyr Arg Asp Lys Thr Glu Glu Leu Met Glu Leu Thr Asp Glu
            100                 105                 110

Gln Arg Asn Glu Leu Met Lys Lys Glu Ser Ser Arg Leu Gln Lys Thr
        115                 120                 125

Gly His Arg Val Thr Tyr Ser Pro Arg Lys Glu Lys Ala Leu Lys Ile
    130                 135                 140
```

```
Tyr Leu Asp Gly Ala Pro Asn Lys Asp Leu Thr Gln Asp
145                 150                 155

<210> SEQ ID NO 4
<211> LENGTH: 347
<212> TYPE: PRT
<213> ORGANISM: Homo sapiens

<400> SEQUENCE: 4

Met Gln Tyr Met Tyr Phe Lys Ala Glu Pro Tyr Ala Ala Asp Glu Gly
1               5                   10                  15

Ser Gly Glu Gly His Lys Trp Leu Met Val His Val Asp Lys Arg Ile
            20                  25                  30

Thr Leu Ala Ala Phe Lys Gln His Leu Glu Pro Phe Val Gly Val Leu
        35                  40                  45

Ser Ser His Phe Lys Val Phe Arg Val Tyr Ala Ser Asn Gln Glu Phe
    50                  55                  60

Glu Ser Val Arg Leu Asn Glu Thr Leu Ser Ser Phe Ser Asp Asp Asn
65                  70                  75                  80

Lys Ile Thr Ile Arg Leu Gly Arg Ala Leu Lys Lys Gly Glu Tyr Arg
                85                  90                  95

Val Lys Val Tyr Gln Leu Leu Val Asn Glu Gln Glu Pro Cys Lys Phe
            100                 105                 110

Leu Leu Asp Ala Val Phe Ala Lys Gly Met Thr Val Arg Gln Ser Lys
        115                 120                 125

Glu Glu Leu Ile Pro Gln Leu Arg Glu Gln Cys Gly Leu Glu Leu Ser
130                 135                 140

Ile Asp Arg Phe Arg Leu Arg Lys Lys Thr Trp Lys Asn Pro Gly Thr
145                 150                 155                 160

Val Phe Leu Asp Tyr His Ile Tyr Glu Glu Asp Ile Asn Ile Ser Ser
                165                 170                 175

Asn Trp Glu Val Phe Leu Glu Val Leu Asp Gly Val Glu Lys Met Lys
            180                 185                 190

Ser Met Ser Gln Leu Ala Val Leu Ser Arg Arg Trp Lys Pro Ser Glu
        195                 200                 205

Met Lys Leu Asp Pro Phe Gln Glu Val Val Leu Glu Ser Ser Ser Val
210                 215                 220

Asp Glu Leu Arg Glu Lys Leu Ser Glu Ile Ser Gly Ile Pro Leu Asp
225                 230                 235                 240

Asp Ile Glu Phe Ala Lys Gly Arg Gly Thr Phe Pro Cys Asp Ile Ser
                245                 250                 255

Val Leu Asp Ile His Gln Asp Leu Asp Trp Asn Pro Lys Val Ser Thr
            260                 265                 270

Leu Asn Val Trp Pro Leu Tyr Ile Cys Asp Asp Gly Ala Val Ile Phe
        275                 280                 285

Tyr Arg Asp Lys Thr Glu Glu Leu Met Glu Leu Thr Asp Glu Gln Arg
290                 295                 300

Asn Glu Leu Met Lys Lys Glu Ser Ser Arg Leu Gln Lys Thr Gly His
305                 310                 315                 320

Arg Val Thr Tyr Ser Pro Arg Lys Glu Lys Ala Leu Lys Ile Tyr Leu
                325                 330                 335

Asp Gly Ala Pro Asn Lys Asp Leu Thr Gln Asp
            340                 345

<210> SEQ ID NO 5
```

```
<211> LENGTH: 331
<212> TYPE: PRT
<213> ORGANISM: Homo sapiens

<400> SEQUENCE: 5

Glu Glu Asp Ser Gly Thr Asp Ser Glu Tyr Asp Glu Ser Gly Lys Ser
1               5                   10                  15

Arg Gly Glu Met Gln Tyr Met Tyr Phe Lys Ala Glu Pro Tyr Ala Ala
            20                  25                  30

Asp Glu Gly Ser Gly Glu Gly His Lys Trp Leu Met Val His Val Asp
        35                  40                  45

Lys Arg Ile Thr Leu Ala Ala Phe Lys Gln His Leu Glu Pro Phe Val
50                  55                  60

Gly Val Leu Ser Ser His Phe Lys Val Phe Arg Val Tyr Ala Ser Asn
65                  70                  75                  80

Gln Glu Phe Glu Ser Val Arg Leu Asn Glu Thr Leu Ser Ser Phe Ser
            85                  90                  95

Asp Asp Asn Lys Ile Thr Ile Arg Leu Gly Arg Ala Leu Lys Lys Gly
            100                 105                 110

Glu Tyr Arg Val Lys Val Tyr Gln Leu Leu Val Asn Glu Gln Glu Pro
        115                 120                 125

Cys Lys Phe Leu Leu Asp Ala Val Phe Ala Lys Gly Met Thr Val Arg
    130                 135                 140

Gln Ser Lys Glu Glu Leu Ile Pro Gln Leu Arg Glu Gln Cys Gly Leu
145                 150                 155                 160

Glu Leu Ser Ile Asp Arg Phe Arg Leu Arg Lys Lys Thr Trp Lys Asn
                165                 170                 175

Pro Gly Thr Val Phe Leu Asp Tyr His Ile Tyr Glu Glu Asp Ile Asn
            180                 185                 190

Ile Ser Ser Asn Trp Glu Val Phe Leu Glu Val Leu Asp Gly Val Glu
        195                 200                 205

Lys Met Lys Ser Met Ser Gln Leu Ala Val Leu Ser Arg Arg Trp Lys
210                 215                 220

Pro Ser Glu Met Lys Leu Asp Pro Phe Gln Glu Val Val Leu Glu Ser
225                 230                 235                 240

Ser Ser Val Asp Glu Leu Arg Glu Lys Leu Ser Glu Ile Ser Gly Ile
                245                 250                 255

Pro Leu Asp Asp Ile Glu Phe Ala Lys Gly Arg Gly Thr Phe Pro Cys
            260                 265                 270

Asp Ile Ser Val Leu Asp Ile His Gln Asp Leu Asp Trp Asn Pro Lys
        275                 280                 285

Val Ser Thr Leu Asn Val Trp Pro Leu Tyr Ile Cys Asp Asp Gly Ala
290                 295                 300

Val Ile Phe Tyr Arg Asp Lys Thr Glu Glu Leu Met Glu Leu Thr Asp
305                 310                 315                 320

Glu Gln Lys Lys Lys Lys Lys Lys Lys
                325                 330

<210> SEQ ID NO 6
<211> LENGTH: 605
<212> TYPE: PRT
<213> ORGANISM: Homo sapiens

<400> SEQUENCE: 6

Met Asp Pro Ala Glu Ala Val Leu Gln Glu Lys Ala Leu Lys Phe Met
1               5                   10                  15
```

-continued

```
Cys Ser Met Pro Arg Ser Leu Trp Leu Gly Cys Ser Ser Leu Ala Asp
            20                  25                  30

Ser Met Pro Ser Leu Arg Cys Leu Tyr Asn Pro Gly Thr Gly Ala Leu
        35                  40                  45

Thr Ala Phe Gln Asn Ser Glu Arg Glu Asp Cys Asn Asn Gly Glu
 50                  55                  60

Pro Pro Arg Lys Ile Ile Pro Glu Lys Asn Ser Leu Arg Gln Thr Tyr
 65              70                  75                  80

Asn Ser Cys Ala Arg Leu Cys Leu Asn Gln Glu Thr Val Cys Leu Ala
                 85                  90                  95

Ser Thr Ala Met Lys Thr Glu Asn Cys Val Ala Lys Thr Lys Leu Ala
            100                 105                 110

Asn Gly Thr Ser Ser Met Ile Val Pro Lys Gln Arg Lys Leu Ser Ala
            115                 120                 125

Ser Tyr Glu Lys Glu Lys Glu Leu Cys Val Lys Tyr Phe Glu Gln Trp
        130                 135                 140

Ser Glu Ser Asp Gln Val Glu Phe Val Glu His Leu Ile Ser Gln Met
145                 150                 155                 160

Cys His Tyr Gln His Gly His Ile Asn Ser Tyr Leu Lys Pro Met Leu
                    165                 170                 175

Gln Arg Asp Phe Ile Thr Ala Leu Pro Ala Arg Gly Leu Asp His Ile
                180                 185                 190

Ala Glu Asn Ile Leu Ser Tyr Leu Asp Ala Lys Ser Leu Cys Ala Ala
            195                 200                 205

Glu Leu Val Cys Lys Glu Trp Tyr Arg Val Thr Ser Asp Gly Met Leu
210                 215                 220

Trp Lys Lys Leu Ile Glu Arg Met Val Arg Thr Asp Ser Leu Trp Arg
225                 230                 235                 240

Gly Leu Ala Glu Arg Arg Gly Trp Gly Gln Tyr Leu Phe Lys Asn Lys
                245                 250                 255

Pro Pro Asp Gly Asn Ala Pro Pro Asn Ser Phe Tyr Arg Ala Leu Tyr
            260                 265                 270

Pro Lys Ile Ile Gln Asp Ile Glu Thr Ile Glu Ser Asn Trp Arg Cys
        275                 280                 285

Gly Arg His Ser Leu Gln Arg Ile His Cys Arg Ser Glu Thr Ser Lys
    290                 295                 300

Gly Val Tyr Cys Leu Gln Tyr Asp Asp Gln Lys Ile Val Ser Gly Leu
305                 310                 315                 320

Arg Asp Asn Thr Ile Lys Ile Trp Asp Lys Asn Thr Leu Glu Cys Lys
                325                 330                 335

Arg Ile Leu Thr Gly His Thr Gly Ser Val Leu Cys Leu Gln Tyr Asp
            340                 345                 350

Glu Arg Val Ile Ile Thr Gly Ser Ser Asp Ser Thr Val Arg Val Trp
        355                 360                 365

Asp Val Asn Thr Gly Glu Met Leu Asn Thr Leu Ile His His Cys Glu
 370                 375                 380

Ala Val Leu His Leu Arg Phe Asn Asn Gly Met Met Val Thr Cys Ser
385                 390                 395                 400

Lys Asp Arg Ser Ile Ala Val Trp Asp Met Ala Ser Pro Thr Asp Ile
                405                 410                 415

Thr Leu Arg Arg Val Leu Val Gly His Arg Ala Ala Val Asn Val Val
            420                 425                 430

Asp Phe Asp Asp Lys Tyr Ile Val Ser Ala Ser Gly Asp Arg Thr Ile
        435                 440                 445
```

```
Lys Val Trp Asn Thr Ser Thr Cys Glu Phe Val Arg Thr Leu Asn Gly
    450                 455                 460

His Lys Arg Gly Ile Ala Cys Leu Gln Tyr Arg Asp Arg Leu Val Val
465                 470                 475                 480

Ser Gly Ser Ser Asp Asn Thr Ile Arg Leu Trp Asp Ile Glu Cys Gly
                485                 490                 495

Ala Cys Leu Arg Val Leu Glu Gly His Glu Glu Leu Val Arg Cys Ile
            500                 505                 510

Arg Phe Asp Asn Lys Arg Ile Val Ser Gly Ala Tyr Asp Gly Lys Ile
        515                 520                 525

Lys Val Trp Asp Leu Val Ala Ala Leu Asp Pro Arg Ala Pro Ala Gly
    530                 535                 540

Thr Leu Cys Leu Arg Thr Leu Val Glu His Ser Gly Arg Val Phe Arg
545                 550                 555                 560

Leu Gln Phe Asp Glu Phe Gln Ile Val Ser Ser Ser His Asp Asp Thr
                565                 570                 575

Ile Leu Ile Trp Asp Phe Leu Asn Asp Pro Ala Ala Gln Ala Glu Pro
            580                 585                 590

Pro Arg Ser Pro Ser Arg Thr Tyr Thr Tyr Ile Ser Arg
        595                 600                 605

<210> SEQ ID NO 7
<211> LENGTH: 6146
<212> TYPE: DNA
<213> ORGANISM: Homo sapiens

<400> SEQUENCE: 7
taagagaggg cgggggggaag gaagaggagg cgggatccgg gcgctgcgtt ggctgcggcc      60
tggcaccaaa ggggcggccc cggcggagag cggacccagt ggcctcggcg attatggacc     120
cggccgaggc ggtgctgcaa gagaaggcac tcaagtttat gtgctctatg cccaggtctc     180
tgtggctggg ctgctccagc ctggcggaca gcatgccttc gctgcgatgc ctgtataacc     240
cagggactgg cgcactcaca gctttccaga attcctcaga gagagaagac tgtaataatg     300
gcgaaccccc taggaagata taccagaga agaattcact tagacagaca tacaacagct     360
gtgccagact ctgcttaaac caagaaacag tatgtttagc aagcactgct atgaagactg     420
agaattgtgt ggccaaaaca aaacttgcca atggcacttc cagtatgatt gtgcccaagc     480
aacggaaact ctcagcaagc tatgaaaagg aaaaggaact gtgtgtcaaa tactttgagc     540
agtggtcaga gtcagatcaa gtggaatttg tggaacatct tatatcccaa atgtgtcatt     600
accaacatgg gcacataaac tcgtatctta aacctatgtt gcagagagat ttcataactg     660
ctctgccagc tcggggattg gatcatattg ctgagaacat tctgtcatac ctggatgcca     720
aatcactatg tgctgctgaa cttgtgtgca aggaatggta ccgagtgacc tctgatggca     780
tgctgtggaa gaagcttatc gagagaatgg tcaggacaga ttctctgtgg agaggcctgg     840
cagaacgaag aggatgggga cagtatttat tcaaaaacaa acctcctgac gggaatgctc     900
ctcccaactc ttttttataga gcactttatc ctaaaattat acaagacatt gagacaatag     960
aatctaattg gagatgtgga agacatagtt tacagagaat tcactgccga agtgaaacaa    1020
gcaaaggagt ttactgttta cagtatgatg atcagaaaat agtaagcggc cttcgagaca    1080
acacaatcaa gatctgggat aaaaacacat ggaatgcaa gcgaattctc acaggccata    1140
caggttcagt cctctgtctc cagtatgatg agagagtgat cataacagga tcatcggatt    1200
ccacggtcag agtgtgggat gtaaatacag gtgaaatgct aaacacgttg attcaccatt    1260
```

```
gtgaagcagt tctgcacttg cgtttcaata atggcatgat ggtgacctgc tccaaagatc    1320
gttccattgc tgtatgggat atggcctccc caactgacat taccctccgg agggtgctgg    1380
tcggacaccg agctgctgtc aatgttgtag actttgatga caagtacatt gtttctgcat    1440
ctggggatag aactataaag gtatggaaca caagtacttg tgaatttgta aggaccttaa    1500
atggacacaa acgaggcatt gcctgtttgc agtacaggga caggctggta gtgagtggct    1560
catctgacaa cactatcaga ttatgggaca tagaatgtgg tgcatgttta cgagtgttag    1620
aaggccatga ggaattggtg cgttgtattc gatttgataa caagaggata gtcagtgggg    1680
cctatgatgg aaaaattaaa gtgtgggatc ttgtggctgc tttggacccc cgtgctcctg    1740
cagggacact ctgtctacgg acccttgtgg agcattccgg aagagttttt cgactacagt    1800
ttgatgaatt ccagattgtc agtagttcac atgatgacac aatcctcatc tgggacttcc    1860
taaatgatcc agctgcccaa gctgaacccc ccgttcccc ttctcgaaca tacacctaca    1920
tctccagata aataaccata cactgacctc atacttgccc aggacccatt aaagttgcgg    1980
tatttaacgt atctgccaat accaggatga gcaacaacag taacaatcaa actactgccc    2040
agtttccctg gactagccga ggagcagggc tttgagactc tgttgggac acagttggtc    2100 tgcagtcggc ccaggacggt ctactcagca caactgactg cttcagtgct gctatcagaa    2160
gatgtcttct atcttttgtg aatgattgga actttaaaac ctcccctcct ctcctccttt    2220
cacctctgca cctagttttt tcccattggt tccagacaaa ggtgacttat aaatatattt    2280
agtgttttgc cagaatctct cttgctttgc cattaagcag aagaactagt ttccctgtat    2340
agcctgctgg gagagaccca cttctagggt atggggatg cagcttcaag cccagtgccc    2400
agtgtctccc tgttaactgc aggaatgcca agcacctggc cagagcagcc cagccccaat    2460
atgcttagga ggagacagag ttccctctgt atagcctctg ggacaagaaa aagaaaacac    2520
aagaatgtat acactggaag atttgggcct cctgcctgcc ttctcttttgt ttctgttcct    2580 cttcccatct actcccctac gccccttcaa cctttttttct ctgtctgctt cacctgagaa    2640
gaaagtgtac gaagagagtg tcctcctctc acatgagcca gatcagccag aaaatgcaac    2700
acttggaaga gttaaatgct gttcagtgaa gatttcagcc ccaggccttt gctgcaagtg    2760
accctgtggc aacagtggat tctcagacat gatactctca tcatatttgc aactcttctc    2820 tctcttttctt ccccacaccc aagaggagga ttggtggtag ggggcaggca gaggggtgg    2880 ggagaagttt cctgggctcc atcaatggct gcatcttttc tggactcagc agtctccttg    2940
attccatgta gagtgtggaa aggagttgct gattgcattt cctctcatta acaattgggt    3000
gtgtaataaa aagcattgta cttcatctta aatcactggt aaggctcagc ctacagaaag    3060
atttgaaatg gccagagcca atcgcttggt gcattctgcg taatggtttc catctccgat    3120
ttcctcatca gggcctgtga atacccaggt gcctgtatct ttgccaagac cgtgatcaag    3180
gtagcttaag agagatggtc aggagaaaac actgttttg tttttttgt tgttttgttt    3240 tgttttggcc agttaaatat catctctcaa atattgatct caccgtgtca accttgcact    3300
gcacaacctt ccttctgctt ctcccacacc cagtatttgc agaagggcaa agctgcttaa    3360
gagagaggat cagggtgaag tttggcacac agggtttatt aatggggcaa aaactgcctt    3420
ttcttcctcc tcctgacctt attttgctct tcactctccc cagccaataa agcgtctgtg    3480
gcgattggtg aacagcataa acagctggac ctcagcaagg gtcaggcaaa cccagtcact    3540
cggaaggcag ctgtgtgagc tgccaagcta gtgggcttca ggtgcaaggg tacctgtgcc    3600
acaccaacct gggagcacac agaatactat taatgtgcac ccagctggtc tccccaggca    3660
```

```
agaaggtatc ctcttcccaa ggtgtaccca ctgaatgttg ttactacata ttgagagtca    3720
ttttatgcat atgcattcta cctttcctgc tttatgagta ttttttaagct tttagttcaa   3780 ggttatattc agaaaatatt tcccagtata atgatacatc gtagcctaag aaatattttc    3840
tcaatgtaat tcccttccca gctacccaaa tgctacagag aaatgttttc tacttggcca    3900
ctatcagggt tcgtcatcta ttgtgttgac tattaatggc ttttttgattg ggtaaggatt   3960 ttgctataga tgaaggtaga gggctgtcag ccctgaaaaa cacacaggtc agacatttaa    4020
aaggcatggg tttcgagctg tctcaaaata ttgcccaata gccataattt taccagcctt    4080
tctgtcatat gctgctatta caaagtggaa gctgttgaat gtttattggt gcccagggtt    4140
ttgctctcca atctaggttc agttgaagga atattgtttc taagactgtt ttgagacatg    4200
tccagtacat cacaaaggag atcggggcga cccctgcaga tgtggagcca ttagcccagt    4260
tgaggatatt ctccaagttg tcctctctcc tgctgatgga aatgggaatg aagttaagtg    4320
gtctgaaaaa cttgaatcgt tcacatttct cagctctggg ggtcatttac cagtttgttg    4380
tagaagaaat aatcaggtaa gttaaaagtt catttccaga aaggtaaaac cccacttacc    4440
atctctgcat gatttcagtg ggaattgatt atcactaatc cccaactggg ctagaataaa    4500
tgtaaagttt gacctttta aaacgaaaag agagacaaag tctcagcaca ttccaaggag     4560
tggtagaaac agagctgaag gtgtccccat tgtagattag tctcttctca ctaaaattta    4620 cttttccaacg tagggcctaa aggaaacctt tcttaaagac aggctgaaac cccttcaaag   4680
gcagatgagg aggtacagac acgtgacctt tggtgcaca ctggagctac ttggacaaga     4740
ccagcatgcc ttgctgcacg tgtgtgtatt tcactgctga aacatccttt taacttggtg    4800
tgcaatttga aaggatgtga atcatggatg gaaggccatt tgtacatgtc ccttggcaaa    4860 attcttttctg gtgtctccta acttcagaga cagggactct ttttggatct ctattgacaa   4920
gtaataaaag tctggccctc ataacttgtt tccgaactag aaaagtctgt gagaccccta    4980
catcattctg gttttttttgc ttgagtaaga acaatccttt tttatttttc ttctgtacag   5040
tctaaagcta cagagaaaaa aaaatgcact cttcccttgc cggctcctgg taccattggt    5100
ctgaacagct gtagttggtc tactccttac ttagcacttg attgtgtggg gaaacaaagg    5160
tgggaggggt ggggaatact ggaaataatc agggcaattt ttttctttcc cataattgga   5220
ctagatacct tggtactgtt gaccttctca gcatctccct tttgccttag atggcaacac    5280
cctccagtct gtagcagagc agtccaaccc agattagtgc agcccggagg cttagggtgc    5340
agcctccctg gtcttcctcc acacagttgt tcaccaacag accagacctc ctttaaccac    5400
agtgtcaaca tagtatcgga aagagagcca tttcttaggg gaataaaaca gtttcgcttc    5460
tttagctcat ctgtggtgtc agaatccttg gagctgaaga gagaaatcaa aagagcatga   5520
tgatggctgc ctggtttcag gtggaactta atgcattgat cttttagaagc tccttctgtt   5580 ggaagttgag tacctgtgat ctaaaatgtc ctggaggcag atgacatcta aaatatgtgc    5640
tttccaacca gcacagctgg cgctcttagc tcctgattgg ttgtgtgttt tattaaggat    5700
cagtgcagtt aagtcgtatt ttaaagtgtt acctcccctc ctaacccttc cccttcttgg    5760
acactgaagg aaaaggccaa ctagggtgtt agccctctgg gcaccaagga aactaacagc    5820
tttctcaaag cggtgaccac tcaggccagc ccagacaaat ctgagggatg gccagtgcac    5880
tccaatgatg ggacaggcct aacaacacat gtaagcttcc ccgagagctt tcagctggtt    5940
cacctctttt ttctctagac tcttaagtac tgactgcttt gacttttgtg attatgttat    6000
ggtgatgtgt agtcagtgta ccaatatgtt cacaacctag gatcatgata atggagtgtg    6060
```

```
ttttgggttt tttttaactg ttcagaaaaa aagtaaatta caaatataag attaaagtga    6120
aaaaaaaaaa aaaaaaaaaa aaaaaa                                        6146

<210> SEQ ID NO 8
<211> LENGTH: 2151
<212> TYPE: DNA
<213> ORGANISM: Homo sapiens

<400> SEQUENCE: 8
tgcgttggct gcggcctggc accaaagggg cggccccggc ggagagcgga cccagtggcc     60
tcggcgatta tggacccggc cgaggcggtg ctgcaagaga aggcactcaa gtttatgaat    120
tcctcagaga gagaagactg taataatggc gaaccccta ggaagataat accagagaag     180
aattcactta gacagacata caacagctgt gccagactct gcttaaacca agaaacagta    240
tgtttagcaa gcactgctat gaagactgag aattgtgtgg ccaaaacaaa acttgccaat    300
ggcacttcca gtatgattgt gcccaagcaa cggaaactct cagcaagcta tgaaaaggaa    360
aaggaactgt gtgtcaaata ctttgagcag tggtcagagt cagatcaagt ggaatttgtg    420
gaacatctta tatcccaaat gtgtcattac caacatgggc acataaactc gtatcttaaa    480
cctatgttgc agagagattt cataactgct ctgccagctc ggggattgga tcatatcgct    540
gagaacattc tgtcatacct ggatgccaaa tcactatgtg ctgctgaact tgtgtgcaag    600
gaatggtacc gagtgacctc tgatggcatg ctgtggaaga agcttatcga gagaatggtc    660
aggacagatt ctctgtggag aggcctggca gaacgaagag gatggggaca gtatttattc    720
aaaaacaaac ctcctgacgg gaatgctcct cccaactctt tttatagagc actttatcct    780
aaaattatac aagacattga acaatagaa tctaattgga gatgtggaag acatagttta     840
cagagaattc actgccgaag tgaaacaagc aaaggagttt actgtttaca gtatgatgat    900
cagaaaatag taagcggcct tcgagacaac acaatcaaga tctgggataa aaacacattg    960
gaatgcaagc gaattctcac aggccataca ggttcagtcc tctgtctcca gtatgatgag    1020
agagtgatca taacaggatc atcggattcc acggtcagag tgtgggatgt aaatacaggt    1080
gaaatgctaa acacgttgat tcaccattgt gaagcagttc tgcacttgcg tttcaataat    1140
ggcatgatgg tgacctgctc caaagatcgt tccattgctg tatgggatat ggcctcccca    1200
actgacatta ccctccggag ggtgctggtc ggacaccgag ctgctgtcaa tgttgtagac    1260
tttgatgaca agtacattgt ttctgcatct ggggatagaa ctataaaggt atggaacaca    1320
agtacttgtg aatttgtaag gaccttaaat ggacacaaac gaggcattgc ctgtttgcag    1380
tacagggaca ggctggtagt gagtggctca tctgacaaca ctatcagatt atgggacata    1440
gaatgtggtg catgtttacg agtgttagaa ggccatgagg aattggtgcg ttgtattcga    1500
tttgataaca gaggatagt cagtggggcc tatgatggaa aaattaaagt gtgggatctt    1560
gtggctgctt ggaccccccg tgctcctgca gggacactct gtctacggac ccttgtggag    1620
cattccggaa gagttttttcg actacagttt gatgaattcc agattgtcag tagttcacat    1680
gatgacacaa tcctcatctg ggacttccta aatgatccag ctgcccaagc tgaacccccc    1740
cgttcccctt ctcgaacata cacctacatc tccagataaa taaccataca ctgacctcat    1800
acttgcccag gacccattaa agttgcggta tttaacgtat ctgccaatac caggatgagc    1860
aacaacagta acaatcaaac tactgcccag tttcctgga ctagccgagg agcagggctt      1920
tgagactcct gttgggacac agttggtctg cagtcggccc aggacggtct actcagcaca    1980
actgactgct tcagtgctgc tatcagaaga tgtcttctat caattgtgaa tgattggaac    2040
```

```
ttttaaacct ccctcctct cctcctttca cctctgcacc tagttttttc ccattggttc    2100
cagacaaagg tgacttataa atatatttag tgttttgcca gaaaaaaaaa a           2151
```

<210> SEQ ID NO 9
<211> LENGTH: 569
<212> TYPE: PRT
<213> ORGANISM: Homo sapiens

<400> SEQUENCE: 9

```
Met Asp Pro Ala Glu Ala Val Leu Gln Glu Lys Ala Leu Lys Phe Met
1               5                   10                  15

Asn Ser Ser Glu Arg Glu Asp Cys Asn Asn Gly Glu Pro Pro Arg Lys
            20                  25                  30

Ile Ile Pro Glu Lys Asn Ser Leu Arg Gln Thr Tyr Asn Ser Cys Ala
        35                  40                  45

Arg Leu Cys Leu Asn Gln Glu Thr Val Cys Leu Ala Ser Thr Ala Met
    50                  55                  60

Lys Thr Glu Asn Cys Val Ala Lys Thr Lys Leu Ala Asn Gly Thr Ser
65                  70                  75                  80

Ser Met Ile Val Pro Lys Gln Arg Lys Leu Ser Ala Ser Tyr Glu Lys
                85                  90                  95

Glu Lys Glu Leu Cys Val Lys Tyr Phe Glu Gln Trp Ser Glu Ser Asp
            100                 105                 110

Gln Val Glu Phe Val Glu His Leu Ile Ser Gln Met Cys His Tyr Gln
        115                 120                 125

His Gly His Ile Asn Ser Tyr Leu Lys Pro Met Leu Gln Arg Asp Phe
    130                 135                 140

Ile Thr Ala Leu Pro Ala Arg Gly Leu Asp His Ile Ala Glu Asn Ile
145                 150                 155                 160

Leu Ser Tyr Leu Asp Ala Lys Ser Leu Cys Ala Ala Glu Leu Val Cys
                165                 170                 175

Lys Glu Trp Tyr Arg Val Thr Ser Asp Gly Met Leu Trp Lys Lys Leu
            180                 185                 190

Ile Glu Arg Met Val Arg Thr Asp Ser Leu Trp Arg Gly Leu Ala Glu
        195                 200                 205

Arg Arg Gly Trp Gly Gln Tyr Leu Phe Lys Asn Lys Pro Pro Asp Gly
    210                 215                 220

Asn Ala Pro Pro Asn Ser Phe Tyr Arg Ala Leu Tyr Pro Lys Ile Ile
225                 230                 235                 240

Gln Asp Ile Glu Thr Ile Glu Ser Asn Trp Arg Cys Gly Arg His Ser
                245                 250                 255

Leu Gln Arg Ile His Cys Arg Ser Glu Thr Ser Lys Gly Val Tyr Cys
            260                 265                 270

Leu Gln Tyr Asp Asp Gln Lys Ile Val Ser Gly Leu Arg Asp Asn Thr
        275                 280                 285

Ile Lys Ile Trp Asp Lys Asn Thr Leu Glu Cys Lys Arg Ile Leu Thr
    290                 295                 300

Gly His Thr Gly Ser Val Leu Cys Leu Gln Tyr Asp Glu Arg Val Ile
305                 310                 315                 320

Ile Thr Gly Ser Ser Asp Ser Thr Val Arg Val Trp Asp Val Asn Thr
                325                 330                 335

Gly Glu Met Leu Asn Thr Leu Ile His His Cys Glu Ala Val Leu His
            340                 345                 350

Leu Arg Phe Asn Asn Gly Met Met Val Thr Cys Ser Lys Asp Arg Ser
```

```
                   355                 360                 365
Ile Ala Val Trp Asp Met Ala Ser Pro Thr Asp Ile Thr Leu Arg Arg
370                 375                 380

Val Leu Val Gly His Arg Ala Ala Val Asn Val Asp Phe Asp Asp
385                 390                 395                 400

Lys Tyr Ile Val Ser Ala Ser Gly Asp Arg Thr Ile Lys Val Trp Asn
                405                 410                 415

Thr Ser Thr Cys Glu Phe Val Arg Thr Leu Asn Gly His Lys Arg Gly
                420                 425                 430

Ile Ala Cys Leu Gln Tyr Arg Asp Arg Leu Val Val Ser Gly Ser Ser
                435                 440                 445

Asp Asn Thr Ile Arg Leu Trp Asp Ile Glu Cys Gly Ala Cys Leu Arg
450                 455                 460

Val Leu Glu Gly His Glu Glu Leu Val Arg Cys Ile Arg Phe Asp Asn
465                 470                 475                 480

Lys Arg Ile Val Ser Gly Ala Tyr Asp Gly Lys Ile Lys Val Trp Asp
                485                 490                 495

Leu Val Ala Ala Leu Asp Pro Arg Ala Pro Ala Gly Thr Leu Cys Leu
                500                 505                 510

Arg Thr Leu Val Glu His Ser Gly Arg Val Phe Arg Leu Gln Phe Asp
                515                 520                 525

Glu Phe Gln Ile Val Ser Ser Ser His Asp Asp Thr Ile Leu Ile Trp
                530                 535                 540

Asp Phe Leu Asn Asp Pro Ala Ala Gln Ala Glu Pro Pro Arg Ser Pro
545                 550                 555                 560

Ser Arg Thr Tyr Thr Tyr Ile Ser Arg
                565

<210> SEQ ID NO 10
<211> LENGTH: 6013
<212> TYPE: DNA
<213> ORGANISM: Homo sapiens

<400> SEQUENCE: 10
taagagaggg cggggggaag gaagaggagg cgggatccgg gcgctgcgtt ggctgcggcc      60
tggcaccaaa ggggcggccc cggcggagag cggacccagt ggcctcggcg attatggacc     120
cggccgaggc ggtgctgcaa gagaaggcac tcaagtttat gaattcctca gagagagaag     180
actgtaataa tggcgaaccc cctaggaaga taataccaga gaagaattca cttagacaga     240
catacaacag ctgtgccaga ctctgcttaa accagaaaac agtatgttta gcaagcactg     300
ctatgaagac tgagaattgt gtggccaaaa caaaacttgc caatggcact tccagtatga     360
ttgtgcccaa gcaacggaaa ctctcagcaa gctatgaaaa ggaaaaggaa ctgtgtgtca     420
atactttgga gcagtggtca gagtcagatc aagtggaatt tgtggaacat cttatatccc     480
aaatgtgtca ttaccaacat gggcacataa actcgtatct taaacctatg ttgcagagag     540
atttcataac tgctctgcca gctcggggat tggatcatat tgctgagaac attctgtcat     600
acctggatgc caaatcacta tgtgctgctg aacttgtgtg caaggaatgg taccgagtga     660
cctctgatgg catgctgtgg aagaagctta tcgagagaat ggtcaggaca gattctctgt     720
ggagaggcct ggcagaacga agaggatggg acagtatttt attcaaaaac aaacctcctg     780
acgggaatgc tcctcccaac tcttttttata gagcacttta tcctaaaatt atacaagaca     840
ttgagacaat agaatctaat tggagatgtg aagacatag tttacagaga attcactgcc     900
gaagtgaaac aagcaaagga gtttactgtt tacagtatga tgatcagaaa atagtaagcg     960
```

```
gccttcgaga caacacaatc aagatctggg ataaaaacac attggaatgc aagcgaattc      1020
tcacaggcca tacaggttca gtcctctgtc tccagtatga tgagagagtg atcataacag      1080
gatcatcgga ttccacggtc agagtgtggg atgtaaatac aggtgaaatg ctaaacacgt      1140
tgattcacca ttgtgaagca gttctgcact tgcgtttcaa taatggcatg atggtgacct      1200
gctccaaaga tcgttccatt gctgtatggg atatggcctc cccaactgac attaccctcc      1260
ggagggtgct ggtcggacac cgagctgctg tcaatgttgt agactttgat gacaagtaca      1320
ttgtttctgc atctggggat agaactataa aggtatggaa cacaagtact tgtgaatttg      1380
taaggacctt aaatggacac aaacgaggca ttgcctgttt gcagtacagg gacaggctgg      1440
tagtgagtgg ctcatctgac aacactatca gattatggga catagaatgt ggtgcatgtt      1500
tacgagtgtt agaaggccat gaggaattgg tgcgttgtat tcgatttgat aacaagagga      1560
tagtcagtgg ggcctatgat ggaaaaatta agtgtgggga tcttgtggct gctttggacc      1620
cccgtgctcc tgcagggaca ctctgtctac ggacccttgt ggagcattcc ggaagagttt      1680
ttcgactaca gtttgatgaa ttccagattg tcagtagttc acatgatgac acaatcctca      1740
tctgggactt cctaaatgat ccagctgccc aagctgaacc ccccgttcc ccttctcgaa      1800 catacaccta catctccaga taaataacca tacactgacc tcatacttgc ccaggaccca      1860
ttaaagttgc ggtatttaac gtatctgcca ataccaggat gagcaacaac agtaacaatc      1920
aaactactgc ccagtttccc tggactagcc gaggagcagg gctttgagac tcctgttggg      1980
acacagttgg tctgcagtcg gcccaggacg gtctactcag cacaactgac tgcttcagtg      2040
ctgctatcag aagatgtctt ctatctttttg tgaatgattg gaacttttaa acctcccctc      2100
ctctcctcct ttcacctctg cacctagttt tttcccattg gttccagaca aaggtgactt      2160
ataaatatat ttagtgtttt gccagaatct ctcttgcttt gccattaagc agaagaacta      2220
gtttccctgt atagcctgct gggagagacc cacttctagg gtatggggga tgcagcttca      2280
agcccagtgc ccagtgtctc cctgttaact gcaggaatgc caagcacctg ccagagcag      2340 cccagcccca atatgcttag gaggagacag agttccctct gtatagcctc tgggacaaga      2400
aaaagaaaac acaagaatgt atacactgga agatttgggc ctcctgcctg ccttctcttt      2460
gtttctgttc ctcttcccat ctactcccct acgcccttc aacctttttt ctctgtctgc      2520
ttcacctgag aagaaagtgt acgaagagag tgtcctcctc tcacatgagc cagatcagcc      2580 agaaatgca acacttggaa gagttaaatg ctgttcagtg aagatttcag ccccaggcct      2640
ttgctgcaag tgaccctgtg caacagtgg attctcagac atgatactct catcatattt      2700
gcaactcttc tctctctttc ttccccacac ccaagaggag gattggtggt aggggcagg      2760 cagaggggt ggggagaagt ttcctgggct ccatcaatgg ctgcatcttt tctggactca      2820
gcagtctcct tgattccatg tagagtgtgg aaaggagttg ctgattgcat ttcctctcat      2880
taacaattgg gtgtgtaata aaaagcattg tacttcatct taaatcactg gtaaggctca      2940
gcctacagaa agatttgaaa tggccagagc caatcgcttg gtgcattctg cgtaatggtt      3000
tccatctccg atttcctcat cagggcctgt gaatacccag gtgcctgtat cttcgccaag      3060
accgtgatca aggtagctta agagagatgt tcaggagaaa acactgtttt tgttttttt       3120 gttgttttgt tttgttttgg ccagttaaat atcatctctc aaatattgat ctcaccgtgt       3180
caaccttgca ctgcacaacc ttccttctgc ttctcccaca cccagtattt gcagaagggc      3240
aaagctgctt aagagagagg atcagggtga agtttggcac acagggttta ttaatggggc      3300
aaaaactgcc ttttcttcct cctcctgacc ttattttgct cttcactctc cccagccaat      3360
```

```
aaagcgtctg tggcgattgg tgaacagcat aaacagctgg acctcagcaa gggtcaggca   3420
aacccagtca ctcggaaggc agctgtgtga gctgccaagc tagtgggctt caggtgcaag   3480
ggtacctgtg ccacaccaac ctgggagcac acagaatact attaatgtgc acccagctgg   3540
tctccccagg caagaaggta tcctcttccc aaggtgtacc cactgaatgt tgttactaca   3600
tattgagagt cattttatgc atatgcattc tacctttcct gctttatgag tattttttaag  3660 cttttagttc aaggttatat tcagaaaata tttcccagta taatgataca tcgtagccta   3720
agaaatattt tctcaatgta attcccttcc cagctaccca aatgctacag agaaatgttt   3780
tctacttggc cactatcagg gttcgtcatc tattgtgttg actattaatg gcttttttgat  3840 tgggtaagga ttttgctata gatgaaggta gagggctgtc agccctgaaa aacacacagg   3900
tcagacattt aaaaggcatg ggtttcgagc tgtctcaaaa tattgcccaa tagccataat   3960
tttaccagcc tttctgtcat atgctgctat tacaaagtgg aagctgttga atgtttattg   4020
gtgcccaggg ttttgctctc caatctaggt tcagttgaag gaatattgtt tctaagactg   4080
ttttgagaca tgtccagtac atcacaaagg agatcggggc gacccctgca gatgtggagc   4140
cattagccca gttgaggata ttctccaagt tgtcctctct cctgctgatg gaaatgggaa   4200
tgaagttaag tggtctgaaa aacttgaatc gttcacattt ctcagctctg ggggtcattt   4260
accagtttgt tgtagaagaa ataatcaggt aagttaaaag ttcatttcca gagaaggtaa   4320
accccactta ccatctctgc atgatttcag tgggaattga ttatcactaa tccccaactg   4380
ggctagaata aatgtaaagt ttgacctttt taaaacgaaa agagagacaa agtctcagca   4440
cattccaagg agtggtagaa acagagctga aggtgtcccc attgtagatt agtctcttct   4500
cactaaaatt tactttccaa cgtagggcct aaaggaaacc tttcttaaag acaggctgaa   4560
accccttcaa aggcagatga ggaggtacag acacgtgacc ttttggtgca cactggagct   4620
acttggacaa gaccagcatg ccttgctgca cgtgtgtgta tttcactgct gagaacatcc   4680
tttaacttgg tgtgcaattt gaaaggatgt gaatcatgga tggaaggcca tttgtacatg   4740
tcccttggca aaattctttc tggtgtctcc taacttcaga gacagggact cttttttggat  4800 ctctattgac aagtaataaa agtctggccc tcataacttg tttccgaact agaaaagtct   4860
gtgagacccc tacatcattc tggtttttt gcttgagtaa gaacaatcct tttttatttt    4920
tcttctgtac agtctaaagc tacagagaaa aaaaaatgca ctcttccctt gccggctcct   4980
ggtaccattg gtctgaacag ctgtagttgg tctactcctt acttagcact tgattgtgtg   5040
gggaaacaaa ggtgggaggg gtggggaata ctggaaataa tcagggcaat tttttctttt   5100
cccataattg gactagatac cttggtactg ttgaccttct cagcatctcc cttttgcctt   5160
agatggcaac ccctccagt ctgtagcaga gcagtccaac ccagattagt gcagcccgga   5220
ggcttagggt gcagcctccc tggtcttcct ccacacagtt gttcaccaac agaccagacc   5280
tcctttaacc acagtgtcaa catagtatcg gaaagagagc catttcttag gggaataaaa   5340
cagtttcgct tctttagctc atctgtggtg tcagaatcct tggagctgaa gagagaaatc   5400
aaaagagcat gatgatggct gcctggtttc aggtggaact taatgcattg atctttagaa   5460
gctccttctg ttggaagttg agtacctgtg atctaaaatg tcctggaggc agatgacatc   5520
taaaatatgt gctttccaac cagcacagct ggcgctctta gctcctgatt ggttgtgtgt   5580
tttattaagg atcagtgcag ttaagtcgta ttttaaagtg ttacctcccc tcctaaccct   5640
tccccttctt ggacactgaa ggaaaaggcc aactagggtg ttagccctct gggcaccaag   5700
gaaactaaca gctttctcaa agcggtgacc actcaggcca gcccagacaa atctgaggga   5760
```

```
tggccagtgc actccaatga tgggacaggc ctaacaacac atgtaagctt ccccgagagc      5820
tttcagctgg ttcacctctt tgttctctag actcttaagt actgactgct ttgactttg       5880 tgattatgtt atggtgatgt gtagtcagtg taccaatatg ttcacaacct aggatcatga      5940
taatggagtg tgttttgggt ttttttttaac tgttcagaaa aaagtaaat tacaaatata      6000 agattaaagt gaa                                                         6013
```

<210> SEQ ID NO 11
<211> LENGTH: 996
<212> TYPE: DNA
<213> ORGANISM: Homo sapiens

<400> SEQUENCE: 11

```
cagaagaaga ctctggaact gatagtgaat atgatgagag tggcaagagt aggggagaaa        60
tgcagtacat gtatttcaaa gctgaacctt atgctgcaga tgaaggttct ggggaaggac       120
ataaatggtt gatggtgcat gttgataaaa gaattactct ggcagctttc aaacaacatt      180
tagagccctt tgttggagtt ttgtcctctc acttcaaggt ctttcgagtg tatgccagca      240
atcaagagtt tgagagcgtc cggctgaatg agacactttc atcattttct gatgacaata      300
agattacaat tagactgggg agagcactta aaaaggaga atacagagtt aaagtatacc       360
agcttttggt caatgaacaa gagccatgca agtttctgct agatgctgtg tttgctaaag      420
gaatgactgt acggcaatca aaagaggaat taattcctca gctcagggag caatgtggtt      480
tagagctcag tattgacagg tttcgtctaa ggaaaaaaac atggaagaat cctggcactg      540 tcttttttgga ttatcatatt tatgaagaag atattaatat ttccagcaac tgggaggttt    600
tccttgaagt tcttgatggg gtagagaaga tgaagtccat gtcacagctt gcagttttgt     660
caagacggtg gaagccttca gagatgaagt tggatcccct ccaggaggtt gtattggaaa     720
gcagtagtgt ggacgaattg cgagagaagc ttagtgaaat cagtgggatt cctttggatg     780
atattgaatt tgctaagggt agaggaacat ttccctgtga tatttctgtc cttgatattc     840
atcaagattt agactggaat cctaaagttt ctacccctgaa tgtctggcct ctttatatct    900
gtgatgatgg tgcggtcata ttttataggg ataaaacaga agaattaatg gaattgacag     960
atgagcaaaa aaaaaaaaaa aaaaaaaaaa aaaaaa                                996
```

<210> SEQ ID NO 12
<211> LENGTH: 1355
<212> TYPE: PRT
<213> ORGANISM: Homo sapiens

<400> SEQUENCE: 12

```
Met Val Pro Gly Glu Glu Asn Gln Leu Val Pro Lys Glu Ile Glu Asn
1               5                   10                  15

Ala Ala Glu Glu Pro Arg Val Leu Cys Ile Ile Gln Asp Thr Thr Asn
            20                  25                  30

Ser Lys Thr Val Asn Glu Arg Ile Thr Leu Asn Leu Pro Ala Ser Thr
        35                  40                  45

Pro Val Arg Lys Leu Phe Glu Asp Val Ala Asn Lys Val Gly Tyr Ile
    50                  55                  60

Asn Gly Thr Phe Asp Leu Val Trp Gly Asn Gly Ile Asn Thr Ala Asp
65                  70                  75                  80

Met Ala Pro Leu Asp His Thr Ser Asp Lys Ser Leu Leu Asp Ala Asn
                85                  90                  95

Phe Glu Pro Gly Lys Lys Asn Phe Leu His Leu Thr Asp Lys Asp Gly
```

```
                100             105             110
Glu Gln Pro Gln Ile Leu Leu Glu Asp Ser Ser Ala Gly Glu Asp Ser
            115                 120                 125

Val His Asp Arg Phe Ile Gly Pro Leu Pro Arg Glu Gly Ser Val Gly
            130                 135             140

Ser Thr Ser Asp Tyr Val Ser Gln Ser Tyr Ser Ser Ile Leu
145                     150                 155                 160

Asn Lys Ser Glu Thr Gly Tyr Val Gly Leu Val Asn Gln Ala Met Thr
                165                 170                 175

Cys Tyr Leu Asn Ser Leu Leu Gln Thr Leu Phe Met Thr Pro Glu Phe
                180                 185                 190

Arg Asn Ala Leu Tyr Lys Trp Glu Phe Glu Glu Ser Glu Glu Asp Pro
            195                 200                 205

Val Thr Ser Ile Pro Tyr Gln Leu Gln Arg Leu Phe Val Leu Leu Gln
210                     215                 220

Thr Ser Lys Lys Arg Ala Ile Glu Thr Thr Asp Val Thr Arg Ser Phe
225                     230                 235                 240

Gly Trp Asp Ser Ser Glu Ala Trp Gln Gln His Asp Val Gln Glu Leu
                245                 250                 255

Cys Arg Val Met Phe Asp Ala Leu Glu Gln Lys Trp Lys Gln Thr Glu
                260                 265                 270

Gln Ala Asp Leu Ile Asn Glu Leu Tyr Gln Gly Lys Leu Lys Asp Tyr
            275                 280                 285

Val Arg Cys Leu Glu Cys Gly Tyr Glu Gly Trp Arg Ile Asp Thr Tyr
            290                 295                 300

Leu Asp Ile Pro Leu Val Ile Arg Pro Tyr Gly Ser Ser Gln Ala Phe
305                 310                 315                 320

Ala Ser Val Glu Glu Ala Leu His Ala Phe Ile Gln Pro Glu Ile Leu
                325                 330                 335

Asp Gly Pro Asn Gln Tyr Phe Cys Glu Arg Cys Lys Lys Lys Cys Asp
            340                 345                 350

Ala Arg Lys Gly Leu Arg Phe Leu His Phe Pro Tyr Leu Leu Thr Leu
            355                 360                 365

Gln Leu Lys Arg Phe Asp Phe Asp Tyr Thr Thr Met His Arg Ile Lys
370                 375                 380

Leu Asn Asp Arg Met Thr Phe Pro Glu Glu Leu Asp Met Ser Thr Phe
385                 390                 395                 400

Ile Asp Val Glu Asp Glu Lys Ser Pro Gln Thr Glu Ser Cys Thr Asp
                405                 410                 415

Ser Gly Ala Glu Asn Glu Gly Ser Cys His Ser Asp Gln Met Ser Asn
            420                 425                 430

Asp Phe Ser Asn Asp Asp Gly Val Asp Glu Gly Ile Cys Leu Glu Thr
        435                 440                 445

Asn Ser Gly Thr Glu Lys Ile Ser Lys Ser Gly Leu Glu Lys Asn Ser
            450                 455                 460

Leu Ile Tyr Glu Leu Phe Ser Val Met Ala His Ser Gly Ser Ala Ala
465                 470                 475                 480

Gly Gly His Tyr Tyr Ala Cys Ile Lys Ser Phe Ser Asp Glu Gln Trp
                485                 490                 495

Tyr Ser Phe Asn Asp Gln His Val Ser Arg Ile Thr Gln Glu Asp Ile
            500                 505                 510

Lys Lys Thr His Gly Gly Ser Ser Gly Ser Arg Gly Tyr Tyr Ser Ser
            515                 520                 525
```

```
Ala Phe Ala Ser Ser Thr Asn Ala Tyr Met Leu Ile Tyr Arg Leu Lys
            530                 535                 540

Asp Pro Ala Arg Asn Ala Lys Phe Leu Glu Val Asp Glu Tyr Pro Glu
545                 550                 555                 560

His Ile Lys Asn Leu Val Gln Lys Glu Arg Glu Leu Glu Glu Gln Glu
                565                 570                 575

Lys Arg Gln Arg Glu Ile Glu Arg Asn Thr Cys Lys Ile Lys Leu Phe
            580                 585                 590

Cys Leu His Pro Thr Lys Gln Val Met Met Glu Asn Lys Leu Glu Val
        595                 600                 605

His Lys Asp Lys Thr Leu Lys Glu Ala Val Glu Met Ala Tyr Lys Met
610                 615                 620

Met Asp Leu Glu Glu Val Ile Pro Leu Asp Cys Cys Arg Leu Val Lys
625                 630                 635                 640

Tyr Asp Glu Phe His Asp Tyr Leu Glu Arg Ser Tyr Glu Gly Glu Glu
                645                 650                 655

Asp Thr Pro Met Gly Leu Leu Gly Gly Val Lys Ser Thr Tyr Met
            660                 665                 670

Phe Asp Leu Leu Leu Glu Thr Arg Lys Pro Asp Gln Val Phe Gln Ser
        675                 680                 685

Tyr Lys Pro Gly Glu Val Met Val Lys Val His Val Val Asp Leu Lys
690                 695                 700

Ala Glu Ser Val Ala Ala Pro Ile Thr Val Arg Ala Tyr Leu Asn Gln
705                 710                 715                 720

Thr Val Thr Glu Phe Lys Gln Leu Ile Ser Lys Ala Ile His Leu Pro
                725                 730                 735

Ala Glu Thr Met Arg Ile Val Leu Glu Arg Cys Tyr Asn Asp Leu Arg
            740                 745                 750

Leu Leu Ser Val Ser Ser Lys Thr Leu Lys Ala Glu Gly Phe Phe Arg
        755                 760                 765

Ser Asn Lys Val Phe Val Glu Ser Glu Thr Leu Asp Tyr Gln Met
770                 775                 780

Ala Phe Ala Asp Ser His Leu Trp Lys Leu Leu Asp Arg His Ala Asn
785                 790                 795                 800

Thr Ile Arg Leu Phe Val Leu Pro Glu Gln Ser Pro Val Ser Tyr
                805                 810                 815

Ser Lys Arg Thr Ala Tyr Gln Lys Ala Gly Asp Ser Gly Asn Val
            820                 825                 830

Asp Asp Asp Cys Glu Arg Val Lys Gly Pro Val Gly Ser Leu Lys Ser
        835                 840                 845

Val Glu Ala Ile Leu Glu Glu Ser Thr Glu Lys Leu Lys Ser Leu Ser
850                 855                 860

Leu Gln Gln Gln Gln Asp Gly Asp Asn Gly Asp Ser Ser Lys Ser Thr
865                 870                 875                 880

Glu Thr Ser Asp Phe Glu Asn Ile Glu Ser Pro Leu Asn Glu Arg Asp
                885                 890                 895

Ser Ser Ala Ser Val Asp Asn Arg Glu Leu Glu Gln His Ile Gln Thr
            900                 905                 910

Ser Asp Pro Glu Asn Phe Gln Ser Glu Arg Ser Asp Ser Asp Val
        915                 920                 925

Asn Asn Asp Arg Ser Thr Ser Ser Val Asp Asp Ile Leu Ser Ser
930                 935                 940

Ser His Ser Ser Asp Thr Leu Cys Asn Ala Asp Asn Ala Gln Ile Pro
945                 950                 955                 960
```

-continued

```
Leu Ala Asn Gly Leu Asp Ser His Ser Ile Thr Ser Ser Arg Arg Thr
                965                 970                 975
Lys Ala Asn Glu Gly Lys Lys Glu Thr Trp Asp Thr Ala Glu Glu Asp
            980                 985                 990
Ser Gly Thr Asp Ser Glu Tyr Asp  Glu Ser Gly Lys Ser  Arg Gly Glu
        995                 1000                1005
Met Gln Tyr Met Tyr Phe Lys  Ala Glu Pro Tyr Ala  Ala Asp Glu
    1010                1015                1020
Gly Ser Gly Glu Gly His Lys  Trp Leu Met Val His  Val Asp Lys
    1025                1030                1035
Arg Ile Thr Leu Ala Ala Phe  Lys Gln His Leu Glu  Pro Phe Val
    1040                1045                1050
Gly Val Leu Ser Ser His Phe  Lys Val Phe Arg Val  Tyr Ala Ser
    1055                1060                1065
Asn Gln Glu Phe Glu Ser Val  Arg Leu Asn Glu Thr  Leu Ser Ser
    1070                1075                1080
Phe Ser Asp Asp Asn Lys Ile  Thr Ile Arg Leu Gly  Arg Ala Leu
    1085                1090                1095
Lys Lys Gly Glu Tyr Arg Val  Lys Val Tyr Gln Leu  Leu Val Asn
    1100                1105                1110
Glu Gln Glu Pro Cys Lys Phe  Leu Leu Asp Ala Val  Phe Ala Lys
    1115                1120                1125
Gly Met Thr Val Arg Gln Ser  Lys Glu Glu Leu Ile  Pro Gln Leu
    1130                1135                1140
Arg Glu Gln Cys Gly Leu Glu  Leu Ser Ile Asp Arg  Phe Arg Leu
    1145                1150                1155
Arg Lys Lys Thr Trp Lys Asn  Pro Gly Thr Val Phe  Leu Asp Tyr
    1160                1165                1170
His Ile Tyr Glu Glu Asp Ile  Asn Ile Ser Ser Asn  Trp Glu Val
    1175                1180                1185
Phe Leu Glu Val Leu Asp Gly  Val Glu Lys Met Lys  Ser Met Ser
    1190                1195                1200
Gln Leu Ala Val Leu Ser Arg  Arg Trp Lys Pro Ser  Glu Met Lys
    1205                1210                1215
Leu Asp Pro Phe Gln Glu Val  Val Leu Glu Ser Ser  Ser Val Asp
    1220                1225                1230
Glu Leu Arg Glu Lys Leu Ser  Glu Ile Ser Gly Ile  Pro Leu Asp
    1235                1240                1245
Asp Ile Glu Phe Ala Lys Gly  Arg Gly Thr Phe Pro  Cys Asp Ile
    1250                1255                1260
Ser Val Leu Asp Ile His Gln  Asp Leu Asp Trp Asn  Pro Lys Val
    1265                1270                1275
Ser Thr Leu Asn Val Trp Pro  Leu Tyr Ile Cys Asp  Asp Gly Ala
    1280                1285                1290
Val Ile Phe Tyr Arg Asp Lys  Thr Glu Glu Leu Met  Glu Leu Thr
    1295                1300                1305
Asp Glu Gln Arg Asn Glu Leu  Met Lys Lys Glu Ser  Ser Arg Leu
    1310                1315                1320
Gln Lys Thr Gly His Arg Val  Thr Tyr Ser Pro Arg  Lys Glu Lys
    1325                1330                1335
Ala Leu Lys Ile Tyr Leu Asp  Gly Ala Gln Asn Lys  Asp Leu Thr
    1340                1345                1350
Gln Asp
```

1355

<210> SEQ ID NO 13
<211> LENGTH: 4524
<212> TYPE: DNA
<213> ORGANISM: Homo sapiens

<400> SEQUENCE: 13

```
gaagtcggct gtggtagcgg cggcggcggc ggcggagccc tgggtcggtg tctgcgcgct     60
ggtgtctgag gcccaggctg aggcctccgc tattgctgga gcgcaggcgg cggagaggat    120
gactgccgct gccattctct cttgagctag cgagccgccg ccaccctcca ccctcccccg    180
gcagggcgga gaggagcggc cggagtcagc gatggtgccc ggcgaggaga accaactggt    240
cccgaaagag atagaaaatg ctgctgaaga acctagagtc ttatgtatta tacaagatac    300
tactaattca aagacagtga atgaacggat cactttaaat ttaccagcat ctactccagt    360
cagaaagctc tttgaagatg tggccaacaa agtaggctac ataaatgaa cctttgactt    420
ggtgtgggga aatggaatca atactgctga tatggcacca ctggatcata ccagtgacaa    480
gtcacttctc gacgctaatt tgagccagg aaagaagaac tttctgcatt tgacagataa    540
agatggtgaa caacctcaaa tactgctgga ggattccagt gctggggaag acagtgttca    600
tgacaggttt ataggtccgc ttccaagaga aggttctgtg ggttctacca gtgattatgt    660
cagccaaagc tactcctact catctatttt gaataaatca gaaactggat atgtgggact    720
agtaaaccaa gcaatgactt gctatttgaa tagccttttg caaacacttt ttatgactcc    780
tgaatttagg aatgcattat ataagtggga atttgaagaa tctgaagaag atccagtgac    840
aagtattcca taccaacttc aaaggctttt tgttttgtta caaaccagca aaaagagagc    900
aattgaaacc acagatgtta caaggagctt tggatgggat agtagtgagg cttggcagca    960
gcatgatgta caagaactat gcagagtcat gtttgatgct ttggaacaga atggaagca   1020
aacagaacag gctgatctta taaatgagct atatcaaggc aagctgaagg actacgtgag   1080
atgtctggaa tgtggttatg agggctggcg aatcgacaca tatcttgata ttccattggt   1140
catccgacct tatgggtcca gccaagcatt tgctagtgtg gaagaagcat tgcatgcatt   1200
tattcagcca gagattctgg atggcccaaa tcagtatttt tgtgaacgtt gtaagaagaa   1260
gtgtgatgca cggaagggcc ttcggttttt gcattttcct tatctgctga ccttacagct   1320
gaaaagattc gatttttgatt atacaacaat gcataggatt aaactgaatg atcgaatgac   1380
atttcccgag gaactagata tgagtacttt tattgatgtt gaagatgaga atctcctca   1440
gactgaaagt tgcactgaca gtggagcaga aaatgaaggt agttgtcaca gtgatcagat   1500
gagcaacgat ttctccaatg atgatggtgt tgatgaagga atctgtcttg aaaccaatag   1560
tggaactgaa aagatctcaa atctggact tgaaaagaat tccttgatct atgaactttt   1620
ctctgttatg gctcattctg ggagcgctgc tggtggtcat tattatgcat gtataaagtc   1680
attcagtgat gagcagtggt acagcttcaa tgatcaacat gtcagcagga taacacaaga   1740
ggacattaag aaaacacatg gtggatcttc aggaagcaga ggatattatt ctagtgcttt   1800
cgcaagttcc acaaatgcat atatgctgat ctatagactg aaggatccag ccagaaatgc   1860
aaaatttcta gaagtggatg aatacccaga acatattaaa acttggtgc agaaagagag   1920
agagttggaa gaacaagaaa agagacaacg agaaattgag cgcaatacat gcaagataaa   1980
attattctgt ttgcatccta caaaacaagt aatgatggaa aataaattgg aggttcataa   2040
ggataagaca ttaaaggaag cagtagaaat ggcttataag atgatggatt tagaagaggt   2100
```

```
aataccoctg gattgctgtc gccttgttaa atatgatgag tttcatgatt atctagaacg    2160
gtcatatgaa ggagaagaag atacaccaat ggggcttcta ctaggtggcg tcaagtcaac    2220
atatatgttt gatctgctgt tggagacgag aaagcctgat caggttttca atcttataaa    2280
cctggagaag tgatggtgaa agttcatgtt gttgatctaa aggcagaatc tgtagctgct    2340
cctataactg ttcgtgctta cttaaatcag acagttacag aattcaaaca actgatttca    2400
aaggccatcc atttacctgc tgaaacaatg agaatagtgc tggaacgctg ctacaatgat    2460
ttgcgtcttc tcagtgtctc cagtaaaacc ctgaaagctg aaggattttt tagaagtaac    2520
aaggtgtttg ttgaaagctc cgagactttg gattaccaga tggcctttgc agactctcat    2580
ttatggaaac tcctggatcg gcatgcaaat acaatcagat tatttgtttt gctacctgaa    2640
caatccccag tatcttattc caaaaggaca gcataccaga aagctggagg cgattctggt    2700
aatgtggatg atgactgtga agagtcaaa ggacctgtag aagcctaaa gtctgtggaa    2760 gctattctag aagaaagcac tgaaaaactc aaaagcttgt cactgcagca acagcaggat    2820
ggagataatg gggacagcag caaaagtact gagacaagtg actttgaaaa catcgaatca    2880
cctctcaatg agagggactc ttcagcatca gtggataata gagaacttga acagcatatt    2940
cagacttctg atccagaaaa ttttcagtct gaagaacgat cagactcaga tgtgaataat    3000
gacaggagta caagttcagt ggacagtgat attcttagct ccagtcatag cagtgatact    3060
ttgtgcaatg cagacaatgc tcagatccct ttggctaatg acttgactc tcacagtatc    3120 acaagtagta aagaacgaa agcaaatgaa gggaaaaaag aaacatggga tacagcagaa    3180
gaagactctg gaactgatag tgaatatgat gagagtggca agagtagggg agaaatgcag    3240
tacatgtatt tcaaagctga accttatgct gcagatgaag ttctgggga aggacataaa    3300 tggttgatgg tgcatgttga taaagaatt actctggcag ctttcaaaca acatttagag    3360 cccttgttg gagttttgtc ctctcacttc aaggtctttc gagtgtatgc cagcaatcaa    3420
gagtttgaga gcgtccggct gaatgagaca ctttcatcat tttctgatga caataagatt    3480
acaattagac tggggagagc acttaaaaaa ggagaataca gagttaaagt ataccagctt    3540
ttggtcaatg aacaagagcc atgcaagttt ctgctagatg ctgtgtttgc taaggaatg    3600 actgtacggc aatcaaaaga ggaattaatt cctcagctca gggagcaatg tggtttagag    3660
ctcagtattg acaggtttcg tctaaggaaa aaaacatgga agaatcctgg cactgtcttt    3720
ttggattatc atatttatga agaagatatt aatatttcca gcaactggga ggttttcctt    3780
gaagttcttg atggggtaga gaagatgaag tccatgtcac agcttgcagt tttgtcaaga    3840
cggtggaagc cttcagagat gaagttggat cccttccagg aggttgtatt ggaaagcagt    3900
agtgtggacg aattgcgaga gaagcttagt gaaatcagtg ggattccttt ggatgatatt    3960
gaatttgcta agggtagagg aacatttccc tgtgatattt ctgtccttga tattcatcaa    4020
gatttagact ggaatcctaa agtttctacg ctgaatgtct ggcctcttta tatctgtgat    4080
gatggtgcgg tcatatttta tagggataaa acagaagaat taatggaact gacagatgag    4140
caaagaaatg aactgatgaa aaagaaagc agtcgactcc agaagactgg acatcgtgta    4200
acatactcac ctcgtaaaga gaaagcacta aaaatatatc tggatggagc acaaaataaa    4260
gatctgactc aagactgact ctgatagtgt agcattttcc ctgggggagt tttggtttta    4320
attagatggt tcactaccac tgggtagtgc cattttggcc ggacatggtt ggggtaaccc    4380
agtgacacca gcactgattg gactgcccta caccaatcag aagctcagtg cccaatgggc    4440 cactgtttt actcggaatc atgttgtgca ctatagtcaa atgtactgta aagtgaaaag    4500
```

```
ggatgtgcaa aaaaaaaaaa aaaa                                          4524
```

<210> SEQ ID NO 14
<211> LENGTH: 524
<212> TYPE: PRT
<213> ORGANISM: Homo sapiens

<400> SEQUENCE: 14

| Met | Glu | Leu | Gly | Pro | Glu | Pro | His | Arg | Arg | Leu | Leu | Phe | Ala |
|---|---|---|---|---|---|---|---|---|---|---|---|---|---|
| 1 | | | | 5 | | | | | 10 | | | | 15 |

Cys Ser Pro Pro Pro Ala Ser Gln Pro Val Val Lys Ala Leu Phe Gly
              20                  25                  30

Ala Ser Ala Ala Gly Gly Leu Ser Pro Val Thr Asn Leu Thr Val Thr
             35                  40                  45

Met Asp Gln Leu Gln Gly Leu Gly Ser Asp Tyr Glu Gln Pro Leu Glu
 50                  55                  60

Val Lys Asn Asn Ser Asn Leu Gln Arg Met Gly Ser Ser Glu Ser Thr
 65                  70                  75                  80

Asp Ser Gly Phe Cys Leu Asp Ser Pro Gly Pro Leu Asp Ser Lys Glu
                 85                  90                  95

Asn Leu Glu Asn Pro Met Arg Arg Ile His Ser Leu Pro Gln Lys Leu
            100                 105                 110

Leu Gly Cys Ser Pro Ala Leu Lys Arg Ser His Ser Asp Ser Leu Asp
        115                 120                 125

His Asp Ile Phe Gln Leu Ile Asp Pro Asp Glu Asn Lys Glu Asn Glu
    130                 135                 140

Ala Phe Glu Phe Lys Lys Pro Val Arg Pro Val Ser Arg Gly Cys Leu
145                 150                 155                 160

His Ser His Gly Leu Gln Glu Gly Lys Asp Leu Phe Thr Gln Arg Gln
                165                 170                 175

Asn Ser Ala Pro Ala Arg Met Leu Ser Ser Asn Glu Arg Asp Ser Ser
            180                 185                 190

Glu Pro Gly Asn Phe Ile Pro Leu Phe Thr Pro Gln Ser Pro Val Thr
        195                 200                 205

Ala Thr Leu Ser Asp Glu Asp Asp Gly Phe Val Asp Leu Leu Asp Gly
    210                 215                 220

Glu Asn Leu Lys Asn Glu Glu Thr Pro Ser Cys Met Ala Ser Leu
225                 230                 235                 240

Trp Thr Ala Pro Leu Val Met Arg Thr Thr Asn Leu Asp Asn Arg Cys
                245                 250                 255

Lys Leu Phe Asp Ser Pro Ser Leu Cys Ser Ser Ser Thr Arg Ser Val
            260                 265                 270

Leu Lys Arg Pro Glu Arg Ser Gln Glu Glu Ser Pro Pro Gly Ser Thr
        275                 280                 285

Lys Arg Arg Lys Ser Met Ser Gly Ala Ser Pro Lys Glu Ser Thr Asn
    290                 295                 300

Pro Glu Lys Ala His Glu Thr Leu His Gln Ser Leu Ser Leu Ala Ser
305                 310                 315                 320

Ser Pro Lys Gly Thr Ile Glu Asn Ile Leu Asp Asn Asp Pro Arg Asp
                325                 330                 335

Leu Ile Gly Asp Phe Ser Lys Gly Tyr Leu Phe His Thr Val Ala Gly
            340                 345                 350

Lys His Gln Asp Leu Lys Tyr Ile Ser Pro Glu Ile Met Ala Ser Val
        355                 360                 365

Leu Asn Gly Lys Phe Ala Asn Leu Ile Lys Glu Phe Val Ile Ile Asp

|   |   |   |   |   | 370 |   |   |   | 375 |   |   |   | 380 |   |
|---|---|---|---|---|---|---|---|---|---|---|---|---|---|---|
| Cys | Arg | Tyr | Pro | Tyr | Glu | Tyr | Glu | Gly | Gly | His | Ile | Lys | Gly | Ala | Val |
| 385 |   |   |   |   | 390 |   |   |   | 395 |   |   |   |   | 400 |

Asn Leu His Met Glu Glu Val Glu Asp Phe Leu Leu Lys Lys Pro
               405                   410                   415

Ile Val Pro Thr Asp Gly Lys Arg Val Ile Val Phe His Cys Glu
               420                   425                   430

Phe Ser Ser Glu Arg Gly Pro Arg Met Cys Arg Tyr Val Arg Glu Arg
               435                   440                   445

Asp Arg Leu Gly Asn Glu Tyr Pro Lys Leu His Tyr Pro Glu Leu Tyr
               450                   455                   460

Val Leu Lys Gly Gly Tyr Lys Glu Phe Phe Met Lys Cys Gln Ser Tyr
465                   470                   475                   480

Cys Glu Pro Pro Ser Tyr Arg Pro Met His His Glu Asp Phe Lys Glu
               485                   490                   495

Asp Leu Lys Lys Phe Arg Thr Lys Ser Arg Thr Trp Ala Gly Glu Lys
               500                   505                   510

Ser Lys Arg Glu Met Tyr Ser Arg Leu Lys Lys Leu
               515                   520

<210> SEQ ID NO 15
<211> LENGTH: 3717
<212> TYPE: DNA
<213> ORGANISM: Homo sapiens

<400> SEQUENCE: 15

```
gaacagcgaa gacagcgtga gcctgggccg ttgcctcgag gctctcgccc ggcttctctt      60
gccgacccgc cacgtttgtt tggatttaat cttcaggttg ccggcgcccg cccgcccgct     120
ggcctcgcgg tgtgagaggg aagcacccgt gcctgtggct ggtggctggc gcctggaggg     180
tccgcacacc cgcccggccg cgccgcttgc ccgcggcagc cgcgtccctg aaccgcggag     240
tcgtgtttgt gtttgacccg cgggcgccgg tggcgcgcgg ccgaggccgg tgtcggcggg     300
gcggggcggt cgcggcggag gcagaggaag agggagcggg agctctgcga ggccgggcgc     360
cgccatggaa ctgggcccgg agccccgca ccgccgccgc ctgctcttcg cctgcagccc     420
ccctcccgcg tcgcagcccg tcgtgaaggc gctatttggc gcttcagccg ccgggggact     480
gtcgcctgtc accaacctga ccgtcactat ggaccagctg cagggtctgg gcagtgatta     540
tgagcaacca ctggaggtga agaacaacag taatctgcag agaatgggct cctccgagtc     600
aacagattca ggtttctgtc tagattctcc tgggccattg gacagtaaag aaaaccttga     660
aaatcctatg agaagaatac attccctacc tcagaagctg ttgggatgta gtccagctct     720
gaagaggagc cattctgatt ctcttgacca tgacatcttt cagctcatcg acccagatga     780
gaacaaggaa aatgaagcct ttgagtttaa gaagccagta agacctgtat ctcgtggctg     840
cctgcactct catggactcc aggagggtaa agatctcttc acacagaggc agaactctgc     900
cccagctcgg atgctttcct caaatgaaag agatagcagt gaaccaggga atttcattcc     960 tcttttttaca ccccagtcac ctgtgacagc cactttgtct gatgaggatg atggcttcgt    1020
ggaccttctc gatggagaga atctgaagaa tgaggaggag accccctcgt gcatggcaag    1080
cctctggaca gctcctctcg tcatgagaac tacaaacctt gacaaccgat gcaagctgtt    1140
tgactcccct tccctgtgta gctccagcac tcggtcagtg ttgaagagac cagaacgatc    1200
tcaagaggag tctccacctg gaagtacaaa ggaggaggaag agcatgtctg gggccagccc    1260
caaagagtca actaatccag agaaggccca tgagactctt catcagtctt tatccctggc    1320
```

```
atcttccccc aaaggaacca ttgagaacat tttggacaat gacccaaggg accttatagg   1380
agacttctcc aagggttatc tctttcatac agttgctggg aaacatcagg atttaaaata   1440
catctctcca gaaattatgg catctgtttt gaatggcaag tttgccaacc tcattaaaga   1500
gtttgttatc atcgactgtc gatacccata tgaatacgag ggaggccaca tcaagggtgc   1560
agtgaacttg cacatggaag aagaggttga agacttctta ttgaagaagc ccattgtacc   1620
tactgatggc aagcgtgtca ttgttgtgtt tcactgcgag ttttcttctg agagaggtcc   1680
ccgcatgtgc cggtatgtga gagagagaga tcgcctgggt aatgaatacc ccaaactcca   1740
ctaccctgag ctgtatgtcc tgaaggggg g atacaaggag ttctttatga aatgccagtc   1800
ttactgtgag ccccctagct accggcccat gcaccacgag gactttaaag aagacctgaa   1860
gaagttccgc accaagagcc ggacctgggc aggggagaag agcaagaggg agatgtacag   1920
tcgtctgaag aagctctgag gcggcagga ccagccagca gcagcccaag cttccctcca   1980
tccccctttta ccctctttgc tgcagagaaa cttaagcaaa ggggacagct gtgtgacatt   2040
tggagagggg gcctgggact tccatgcctt aaacctacct cccacactcc caaggttgga   2100
gcccagggca tcttgctggc tacgcctctt ctgtccctgt tagacgtcct ccgtccatat   2160
cagaactgtg ccacaatgca gttctgagca ccgtgtcaag ctgctctgag ccacagtggg   2220
atgaaccagc cggggcctta tcgggctcca gccatctcat gaggggagag gagacgagg   2280
ggagtagaga agttacacag aaatgctgct ggccaaatag caaagacaac ctgggaagga   2340
aaggtctttg tgggataatc catatgttta atttattcaa cttcatcaat cactttattt   2400
tatttttttt tctaactcct ggagacttat tttactgctt cattaggttg aaatactgcc   2460
attctaggta gggttttatt atcccaggga ctacctcggc ttttaattta aaaaaaaaa   2520
agaagtgggt aagaaaatgc aaacctgtta taagttatcg gacagaaagc taggtgctct   2580
gtcaccccca ggaggcgctg tggtactggg gctgctgcta tttaagccaa gaactgaggt   2640
cctggtgaga gcgttggacc caggcttggc tgcctgacat aagctaaatc tcccagaccc   2700
accactggct accgatatct atttggtggg aggtgtggcc ctgttcttcc tcaccccagt   2760
tccatgacat tggctggtat aggagccaca gtcaggaaag cacttgaggc agcatctgtt   2820
gggccacccc cggctcagtg ctggaatgtt gcagtgtagg tttcccaggg aagggggtg   2880
gggtaggtg ggctccacag gatggggag gagcatgtcc actgagtatc ttccttatgt   2940
tgctgtgata ttgatagctt ttatttttcta atttttaaaa aatggtcata ttatgagtca   3000
aagagtatca aatcagtgtt ggatggacca cccaagggtg aggagagggg ctggaagccc   3060
tgggcattag gagaagggag tgggtgctgg catggacatg actggataga atttctcag   3120
gagggagctt ggtggatttt gaaggtaaaa ctttctgggt ttatcatgtt ttaattttag   3180
agacagggag tgatgaatca tcaccggttg tcccctatc taactccata aaagtgggaa   3240
tttcaaaaga acacctcatc caaggagctg gggcagactt cattgattct agagagacct   3300
gtttcagtgc ctactcatcc ctgccctctg gtgccagcct ccttaccatc acggcttcac   3360
tgaggtgtag gtgggttttt cttaaacagg agacagtctc tcccctctta cctcaacttc   3420
ttggggtggg aatcagtgat actggagatg gctagttgct gtgttacggg tttgagttac   3480
atttggctat aaaacaatct tgttgggaaa aatgtgggg agaggacttc ttcctacacg   3540
cgcattgaga cagattccaa ctggttaatg atattgtttg taagaaagag attctgttgg   3600
ttgactgcct aaagagaaag gtgggatggc cttcagatta taccagctta gctagcatta   3660
ctaaccaact gttggaagct ctgaaaataa aagatcttga acccataaaa aaaaaaa      3717
```

```
<210> SEQ ID NO 16
<211> LENGTH: 21
<212> TYPE: RNA
<213> ORGANISM: Homo sapiens

<400> SEQUENCE: 16
ggacuugacu cucacaguau u                                              21

<210> SEQ ID NO 17
<211> LENGTH: 21
<212> TYPE: RNA
<213> ORGANISM: Homo sapiens

<400> SEQUENCE: 17
gcaacgauuu cuccaaugau u                                              21
```